US012605472B2

(12) United States Patent (10) Patent No.: US 12,605,472 B2
Ludwig et al. (45) Date of Patent: Apr. 21, 2026

(54) RADIOLABELING OF ANTI-CD45 IMMUNOGLOBULIN AND METHODS OF USE THEREOF

(71) Applicant: Actinium Pharmaceuticals, Inc., New York, NY (US)

(72) Inventors: Dale Ludwig, Rockaway, NJ (US); Sandesh Seth, New York, NY (US)

(73) Assignee: Actinium Pharmaceuticals, Inc., New York, NY (US)

( * ) Notice: Subject to any disclaimer, the term of this patent is extended or adjusted under 35 U.S.C. 154(b) by 1039 days.

(21) Appl. No.: 17/761,579

(22) PCT Filed: Sep. 17, 2020

(86) PCT No.: PCT/US2020/051324
§ 371 (c)(1),
(2) Date: Mar. 17, 2022

(87) PCT Pub. No.: WO2021/055638
PCT Pub. Date: Mar. 25, 2021

(65) Prior Publication Data
US 2022/0378955 A1 Dec. 1, 2022

Related U.S. Application Data

(60) Provisional application No. 62/901,290, filed on Sep. 17, 2019.

(51) Int. Cl.
| | |
|---|---|
| *A61K 51/10* | (2006.01) |
| *A61K 41/00* | (2020.01) |
| *A61P 7/00* | (2006.01) |
| *A61P 35/00* | (2006.01) |
| *A61P 37/04* | (2006.01) |
| *C07K 16/28* | (2006.01) |
| *A61K 39/00* | (2006.01) |

(52) U.S. Cl.
CPC ...... *A61K 51/1027* (2013.01); *A61K 41/0038* (2013.01); *A61P 7/00* (2018.01); *A61P 35/00* (2018.01); *A61P 37/04* (2018.01); *C07K 16/289* (2013.01); *A61K 2039/505* (2013.01)

(58) Field of Classification Search
CPC ............ A61K 51/1027; A61K 41/0038; A61K 2039/505; A61K 35/28; A61K 51/1093; A61K 51/1096; A61P 7/00; A61P 35/00; A61P 37/04; A61P 35/02; C07K 16/289; C07K 2317/90
See application file for complete search history.

(56) References Cited

U.S. PATENT DOCUMENTS

| | | |
|---|---|---|
| 10,420,851 B2 | 9/2019 | Dave et al. |
| 11,912,780 B2 | 2/2024 | Berger et al. |
| 2016/0361360 A1 | 12/2016 | Chang et al. |
| 2017/0326259 A1 | 11/2017 | Dave et al. |
| 2018/0296603 A1 | 10/2018 | Gori et al. |
| 2018/0296708 A1 | 10/2018 | Dave et al. |
| 2020/0255520 A1 | 8/2020 | Berger et al. |
| 2020/0283539 A1 | 9/2020 | Seth et al. |
| 2021/0198359 A1 | 7/2021 | Berger et al. |
| 2022/0202967 A1 | 6/2022 | Ludwig et al. |

FOREIGN PATENT DOCUMENTS

| | | |
|---|---|---|
| WO | 2016/187514 A1 | 11/2016 |
| WO | 2017/155937 A1 | 9/2017 |

OTHER PUBLICATIONS

Alzubi et al., Targeted genome editing restores T cell differentiation in a humanized X-SCID pluripotent stem cell disease model, Scientific Reports, 7:12475, (Sep. 2017), 1-11.
Chang et al., Modeling Human Severe Combined Immunodeficiency and Correction by CRISPR/Cas9-Enhanced Gene Targeting, Cell Reports 12, (Sep. 8, 2015) 1668-1677.
Chang et al., Initiation of T cell signaling by CD45 segregation at 'closecontacts', Nat Immunol. May 2016 ; 17(5): 574-582.
Desai et al., The catalytic activity of the CD45 membrane-proximal phosphatase domain is required for TCR signaling and regulation, The EMBO Journal, vol. 13, No. 17 (1994) 4002-4010.
D'Aloia et al., CAR-T cells: the long and winding road to solid tumors, Cell Death and Disease (2018)9:282.
Dever et al., CRISPR/Cas9 Beta-globin Gene Targeting in Human Hematopoietic Stem Cells, Nature, 539(7629), Nov. 2016, 384-389.
Eyquem et al., Targeting a CAR to the TRAC locus with CRISPR/Cas9 enhances tumour rejection, Nature. Mar. 2, 2017; 543(7643): 113-117.
Klebanoff et al., Sinks, suppressors and antigen presenters: how lymphodepletion enhances T cell-mediated tumor immunotherapy, Trends Immunol. Feb. 2005 ; 26(2): 111-117.
Louis et al., Enhancing the in vivo expansion of adoptively transferred EBV-specific CTL with lymphodepleting CD45 monoclonal antibodies in NPC patients, Blood, Mar. 12, 2009, vol. 113, No. 11:2442-2450.
Muranski et al., Increased intensity lymphodepletion and adoptive immunotherapy—how far can we go?, Nature Clinical Practice, Oncology, vol. 3, No. 12 (Dec. 2006) 668-672.
Ren et al., Multiplex Genome Editing to Generate Universal CAR T Cells Resistant to PD1 Inhibition, Clin Cancer Res, 23(9), May 2017, 2255-2266.
Streuli et al., Differential Usage of three exons generates at least five different mRNAs encoding human leukocyte common antigens, J. Exp. Med, vol. 166, (Nov. 1987) 1548-1566.
Sun et al., Seamless Correction of the Sickle Cell Disease Mutation of the HBB Gene in Human Induced Pluripotent Stem Cells Using TALENs, Biotechnology and Bioengineering, vol. 111, No. 5, May 2014, 1048-1053.

(Continued)

*Primary Examiner* — Robert S Cabral
(74) *Attorney, Agent, or Firm* — Michael E. Dukes; Dentons Cohen & Grigsby, P.C.

(57) ABSTRACT

Compositions and methods useful for the treatment of hemoglobinopathies and hematological diseases are disclosed herein. The compositions include an actinium-225 labeled anti-CD45 antibody (BC8) formulated as a single patient dose that is wholly deliverable to a patient in a single dose. The actinium-225 labeled anti-CD45 may be administered alone or in combination with additional therapeutic agents, such as other immunotherapeutics or a radiosensitizing agent, or additional therapeutic interventions, such as bone marrow transplant or adoptive cell therapies.

23 Claims, 29 Drawing Sheets

Specification includes a Sequence Listing.

(56)     References Cited

OTHER PUBLICATIONS

International Search Report and Written Opinion dated Feb. 9, 2021 for International Application No. PCT/US2020/051324.

Dadachova et al., 1999, Spectrophotometric method for determination of bifunctional macrocyclic ligands in macrocyclic ligand-protein conjugates, Nuclear Medicine & Biology, (1999) 26:977-982.

Hermiston et al., 2003, CD45: A critical regulator of signaling thresholds in immune cells, Ann. Rev. Immunol., 21:107-137.

Penninger et al., 2001, CD45: new jobs for an old acquaintance, Nat. Immunol., (May 2001) 2(5):389-396.

Maine et al., Making room for T cells, J. Clin, Invest, 2002, 110:157-159.

Perini et al., BCL-2 as therapeutic target for hematological malignancies, J. of Hematology & Oncology, vol. 11, No. 65 (May 2018), 1-15.

FIG. 2

| Variable Light Chain (VL) | DIALTQSPASLAVSLGQRATISCRASKSVSTSGYSYLHWYQQKPGQPPKLLIYLAS NLESGVPARFSGSGSGTDFTLNIHPVEEEDAATYYCQHSRELPFTFGSGTKLEIK<br><br>(Sequence ID No: 1) |
|---|---|
| Variable Heavy Chain (VH) | EVKLLESGGGLVQPGGSLKLSCAASGFDFSRYWMSWVRQAPGKGLEWIGEINPTSS TINFTPSLKDKVFISRDNAKNTLYLQMSKVRSEDTALYYCARGNYYRYGDAMDYWG QGTSVTVSSAK<br><br>(Sequence ID No: 2) |

FIG. 3

The Light Chain CDRs:

| | | |
|---|---|---|
| LC-CDR-1: | RASKSVSTSGYSYLH | (Sequence ID NO:3) |
| LC-CDR-2: | LASNLES | (Sequence ID NO:4) |
| LC-CDR-3: | QHSRELPFT | (Sequence ID NO:5) |

The Heavy Chain CDRs:

| | | |
|---|---|---|
| HC-CDR-1: | GFDFSRYWMS | (Sequence ID NO:6) |
| HC-CDR-2: | EINPTSSTINFTPSLKD | (Sequence ID NO:7) |
| HC-CDR-3: | GNYYRYGDAMDY | (Sequence ID NO:8) |

| | | |
|---|---|---|
| The Light Chain N-term: | DIALTQS | (Sequence ID NO:9) |

| | | |
|---|---|---|
| The Heavy Chain N-term: | EVKLLES | (Sequence ID NO:10) |

FIG. 4A

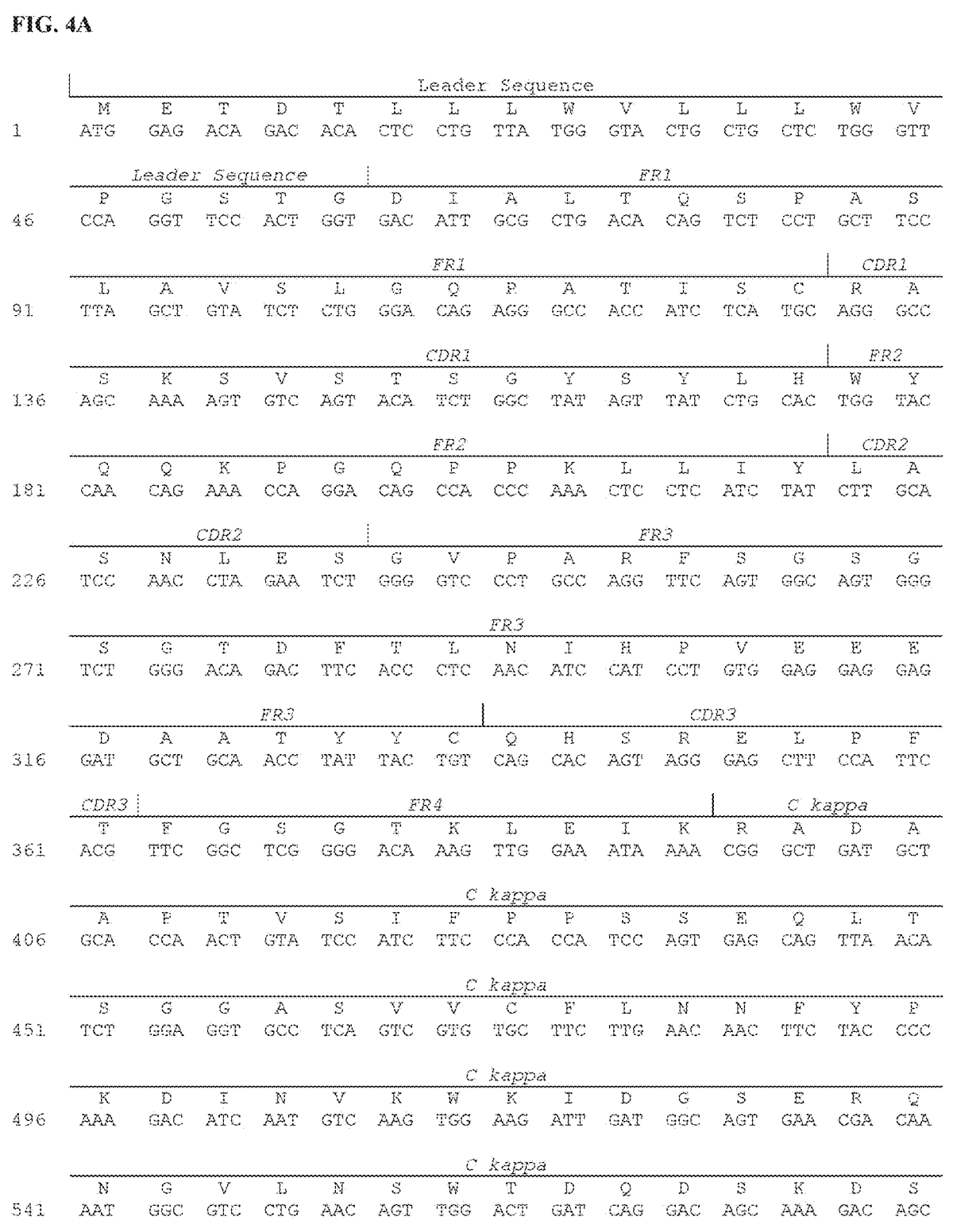

```
                              Leader Sequence
       M     E     T     D     T     L     L     L     W     V     L     L     L     W     V
1     ATG   GAG   ACA   GAC   ACA   CTC   CTG   TTA   TGG   GTA   CTG   CTG   CTC   TGG   GTT Leader Sequence              |                    FR1
       P     G     S     T     G     D     I     A     L     T     Q     S     P     A     S
46    CCA   GGT   TCC   ACT   GGT   GAC   ATT   GCG   CTG   ACA   CAG   TCT   CCT   GCT   TCC FR1                                        |        CDR1
       L     A     V     S     L     G     Q     P     A     T     I     S     C     R     A
91    TTA   GCT   GTA   TCT   CTG   GGA   CAG   AGG   GCC   ACC   ATC   TCA   TGC   AGG   GCC CDR1                                       |        FR2
       S     K     S     V     S     T     S     G     Y     S     Y     L     H     W     Y
136   AGC   AAA   AGT   GTC   AGT   ACA   TCT   GGC   TAT   AGT   TAT   CTG   CAC   TGG   TAC FR2                                        |        CDR2
       Q     Q     K     P     G     Q     P     P     K     L     L     I     Y     L     A
181   CAA   CAG   AAA   CCA   GGA   CAG   CCA   CCC   AAA   CTC   CTC   ATC   TAT   CTT   GCA CDR2             |                    FR3
       S     N     L     E     S     G     V     P     A     R     F     S     G     S     G
226   TCC   AAC   CTA   GAA   TCT   GGG   GTC   CCT   GCC   AGG   TTC   AGT   GGC   AGT   GGG FR3
       S     G     T     D     F     T     L     N     I     H     P     V     E     E     E
271   TCT   GGG   ACA   GAC   TTC   ACC   CTC   AAC   ATC   CAT   CCT   GTG   GAG   GAG   GAG FR3                      |                 CDR3
       D     A     A     T     Y     Y     C     Q     H     S     R     E     L     P     F
316   GAT   GCT   GCA   ACC   TAT   TAC   TGT   CAG   CAC   AGT   AGG   GAG   CTT   CCA   TTC CDR3 |                  FR4                    |          C kappa
       T     F     G     S     G     T     K     L     E     I     K     R     A     D     A
361   ACG   TTC   GGC   TCG   GGG   ACA   AAG   TTG   GAA   ATA   AAA   CGG   GCT   GAT   GCT C kappa
       A     P     T     V     S     I     F     P     P     S     S     E     Q     L     T
406   GCA   CCA   ACT   GTA   TCC   ATC   TTC   CCA   CCA   TCC   AGT   GAG   CAG   TTA   ACA C kappa
       S     G     G     A     S     V     V     C     F     L     N     N     F     Y     P
451   TCT   GGA   GGT   GCC   TCA   GTC   GTG   TGC   TTC   TTG   AAC   AAC   TTC   TAC   CCC C kappa
       K     D     I     N     V     K     W     K     I     D     G     S     E     R     Q
496   AAA   GAC   ATC   AAT   GTC   AAG   TGG   AAG   ATT   GAT   GGC   AGT   GAA   CGA   CAA C kappa
       N     G     V     L     N     S     W     T     D     Q     D     S     K     D     S
541   AAT   GGC   GTC   CTG   AAC   AGT   TGG   ACT   GAT   CAG   GAC   AGC   AAA   GAC   AGC
```

FIG. 4A (continued)

|  | | | | | | | *C kappa* | | | | | | |
|---|---|---|---|---|---|---|---|---|---|---|---|---|---|
| T | Y | S | M | S | S | T | L | T | L | T | K | D | E | Y |
| 586 ACC | TAC | AGC | ATG | AGC | AGC | ACC | CTC | ACG | TTG | ACC | AAG | GAC | GAG | TAT |

|  | | | | | | | *C kappa* | | | | | | |
|---|---|---|---|---|---|---|---|---|---|---|---|---|---|
| E | R | H | N | S | Y | T | C | E | A | T | H | K | T | S |
| 631 GAA | CGA | CAT | AAC | AGC | TAT | ACC | TGT | GAG | GCC | ACT | CAC | AAG | ACA | TCA |

|  | | | | | | | *C kappa* | | | | | | *Stop* |
|---|---|---|---|---|---|---|---|---|---|---|---|---|---|
| T | S | P | I | V | K | S | F | N | R | N | E | C | * |
| 676 ACT | TCA | CCC | ATT | GTC | AAG | AGC | TTC | AAC | AGG | AAT | GAG | TGT | TAG |

SEQ ID NO:11 Nucleotide Sequence

SEQ ID NO:12 Amino Acid Sequence

FIG. 4B

N-Terminal

Asp Ile Ala Leu Thr Gln Ser Pro Ala Ser Leu Ala Val Ser Leu Gly Gln Arg Ala Thr
1            5                   10                  15                  20

| CDR1
Ile Ser Cys Arg Ala Ser Lys Ser Val Ser Thr Ser Gly Tyr Ser Tyr Leu His Trp Tyr
21           25                  30                  35                  40

| CDR2                              |
Gln Gln Lys Pro Gly Gln Pro Pro Lys Leu Leu Ile Tyr Leu Ala Ser Asn Leu Glu Ser
41           45                  50                  55                  60

Gly Val Pro Ala Arg Phe Ser Gly Ser Gly Ser Gly Thr Asp Phe Thr Leu Asn Ile His
61           65                  70                  75                  80

| CDR3
Pro Val Glu Glu Glu Asp Ala Ala Thr Tyr Tyr Cys Gln His Ser Arg Glu Leu Pro Phe
81           85                  90                  95                  100

Thr Phe Gly Ser Gly Thr Lys Leu Glu Ile Lys Arg Ala Asp Ala Ala Pro Thr Val Ser
101          105                 110                 115                 120

Ile Phe Pro Pro Ser Ser Glu Gln Leu Thr Ser Gly Gly Ala Ser Val Val Cys Phe Leu
121          125                 130                 135                 140

Asn Asn Phe Tyr Pro Lys Asp Ile Asn Val Lys Trp Lys Ile Asp Gly Ser Glu Arg Gln
141          145                 150                 155                 160

Asn Gly Val Leu Asn Ser Trp Thr Asp Gln Asp Ser Lys Asp Ser Thr Tyr Ser Met Ser
161          165                 170                 175                 180

C-Terminal
Ser Thr Leu Thr Leu Thr Lys Asp Glu Tyr Glu Arg His Asn Ser Tyr Thr Cys Glu Ala
181          185                 190                 195                 200

Thr His Lys Thr Ser Thr Ser Pro Ile Val Lys Ser Phe Asn Arg Asn Glu Cys
201          205                 210                 215          218

SEQ ID NO:13 Amino Acid Sequence

FIG. 5A

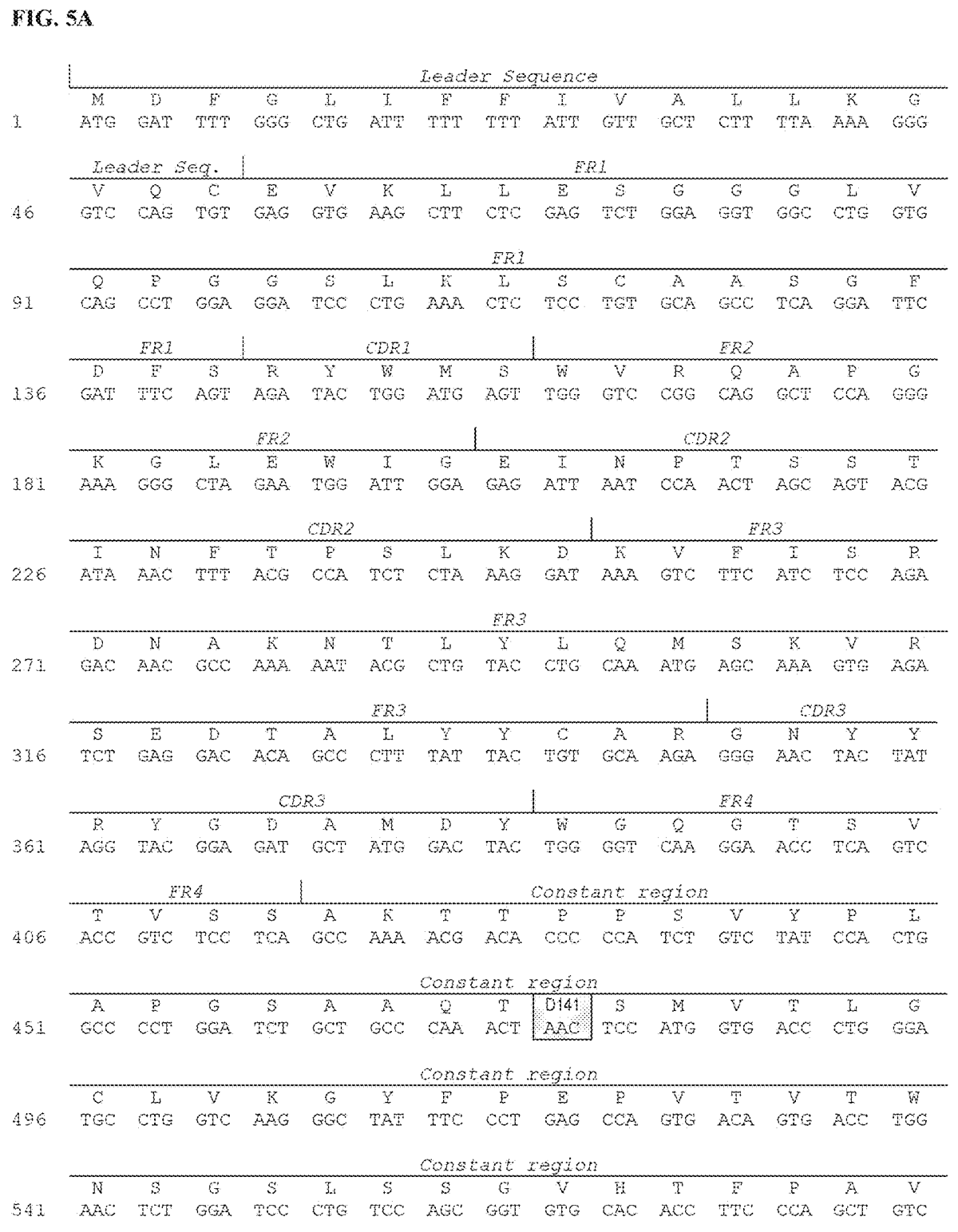

```
                                   Leader Sequence
       M     D     F     G     L     I     F     F     I     V     A     L     L     K     G
 1    ATG   GAT   TTT   GGG   CTG   ATT   TTT   TTT   ATT   GTT   GCT   CTT   TTA   AAA   GGG Leader Seq. |                              FR1
       V     Q     C     E     V     K     L     L     E     S     G     G     G     L     V
46    GTC   CAG   TGT   GAG   GTG   AAG   CTT   CTC   GAG   TCT   GGA   GGT   GGC   CTG   GTG FR1
       Q     P     G     G     S     L     K     L     S     C     A     A     S     G     F
91    CAG   CCT   GGA   GGA   TCC   CTG   AAA   CTC   TCC   TGT   GCA   GCC   TCA   GGA   TTC FR1          |            CDR1             |               FR2
       D     F     S     R     Y     W     M     S     W     V     R     Q     A     P     G
136   GAT   TTC   AGT   AGA   TAC   TGG   ATG   AGT   TGG   GTC   CGG   CAG   GCT   CCA   GGG FR2               |                 CDR2
       K     G     L     E     W     I     G     E     I     N     P     T     S     S     T
181   AAA   GGG   CTA   GAA   TGG   ATT   GGA   GAG   ATT   AAT   CCA   ACT   AGC   AGT   ACG CDR2                    |              FR3
       I     N     F     T     P     S     L     K     D     K     V     F     I     S     P
226   ATA   AAC   TTT   ACG   CCA   TCT   CTA   AAG   GAT   AAA   GTC   TTC   ATC   TCC   AGA FR3
       D     N     A     K     N     T     L     Y     L     Q     M     S     K     V     R
271   GAC   AAC   GCC   AAA   AAT   ACG   CTG   TAC   CTG   CAA   ATG   AGC   AAA   GTG   AGA FR3                           |          CDR3
       S     E     D     T     A     L     Y     Y     C     A     R     G     N     Y     Y
316   TCT   GAG   GAC   ACA   GCC   CTT   TAT   TAC   TGT   GCA   AGA   GGG   AAC   TAC   TAT CDR3                      |                FR4
       R     Y     G     D     A     M     D     Y     W     G     Q     G     T     S     V
361   AGG   TAC   GGA   GAT   GCT   ATG   GAC   TAC   TGG   GGT   CAA   GGA   ACC   TCA   GTC FR4          |                Constant region
       T     V     S     S     A     K     T     T     P     P     S     V     Y     P     L
406   ACC   GTC   TCC   TCA   GCC   AAA   ACG   ACA   CCC   CCA   TCT   GTC   TAT   CCA   CTG Constant region
       A     P     G     S     A     A     Q     T    D141   S     M     V     T     L     G
451   GCC   CCT   GGA   TCT   GCT   GCC   CAA   ACT   AAC   TCC   ATG   GTG   ACC   CTG   GGA Constant region
       C     L     V     K     G     Y     F     P     E     P     V     T     V     T     W
496   TGC   CTG   GTC   AAG   GGC   TAT   TTC   CCT   GAG   CCA   GTG   ACA   GTG   ACC   TGG Constant region
       N     S     G     S     L     S     S     G     V     H     T     F     P     A     V
541   AAC   TCT   GGA   TCC   CTG   TCC   AGC   GGT   GTG   CAC   ACC   TTC   CCA   GCT   GTC
```

FIG. 5A (continued)

*Constant region*

|  | L | Q | S | D | L | Y | T | L | S | S | S | V | T | V | P |
|---|---|---|---|---|---|---|---|---|---|---|---|---|---|---|---|
| 586 | CTG | CAG | TCT | GAC | CTC | TAC | ACT | CTG | AGC | AGC | TCA | GTG | ACT | GTC | CCC |

*Constant region*

|  | S | S | T | W | P | S | E | T | V | T | C | N | V | A | H |
|---|---|---|---|---|---|---|---|---|---|---|---|---|---|---|---|
| 631 | TCC | AGC | ACC | TGG | CCC | AGC | GAG | ACC | GTC | ACC | TGC | AAC | GTT | GCC | CAC |

*Constant region*

|  | P | A | S | S | T | K | V | D | K | K | I | V | P | R | D |
|---|---|---|---|---|---|---|---|---|---|---|---|---|---|---|---|
| 676 | CCG | GCC | AGC | AGC | ACC | AAG | GTG | GAC | AAG | AAA | ATT | GTG | CCC | AGG | GAT |

*Constant region*

|  | C | G | C | K | P | C | I | C | T | V | P | E | V | S | S |
|---|---|---|---|---|---|---|---|---|---|---|---|---|---|---|---|
| 721 | TGT | GGT | TGT | AAG | CCT | TGC | ATA | TGT | ACA | GTC | CCA | GAA | GTA | TCA | TCT |

*Constant region*

|  | V | F | I | F | P | P | K | P | K | D | V | L | T | I | T |
|---|---|---|---|---|---|---|---|---|---|---|---|---|---|---|---|
| 766 | GTC | TTC | ATC | TTC | CCC | CCA | AAG | CCC | AAG | GAT | GTG | CTC | ACC | ATT | ACT |

*Constant region*

|  | L | T | P | K | V | T | C | V | V | V | D | I | S | K | D |
|---|---|---|---|---|---|---|---|---|---|---|---|---|---|---|---|
| 811 | CTG | ACT | CCT | AAG | GTC | ACG | TGT | GTT | GTG | GTA | GAC | ATC | AGC | AAG | GAT |

*Constant region*

|  | D | P | E | V | Q | F | S | W | F | V | D | D | V | E | V |
|---|---|---|---|---|---|---|---|---|---|---|---|---|---|---|---|
| 856 | GAT | CCC | GAG | GTC | CAG | TTC | AGC | TGG | TTT | GTA | GAT | GAT | GTG | GAG | GTG |

*Constant region*

|  | H | T | A | Q | T | Q | P | R | E | E | Q | F | N | S | T |
|---|---|---|---|---|---|---|---|---|---|---|---|---|---|---|---|
| 901 | CAC | ACA | GCT | CAG | ACG | CAA | CCC | CGG | GAG | GAG | CAG | TTC | AAC | AGC | ACT |

*Constant region*

|  | F | R | S | V | S | E | L | P | I | M | H | Q | D | W | L |
|---|---|---|---|---|---|---|---|---|---|---|---|---|---|---|---|
| 946 | TTC | CGC | TCA | GTC | AGT | GAA | CTT | CCC | ATC | ATG | CAC | CAG | GAC | TGG | CTC |

*Constant region*

|  | N | G | K | E | F | K | C | R | V | N | S | A | A | F | P |
|---|---|---|---|---|---|---|---|---|---|---|---|---|---|---|---|
| 991 | AAT | GGC | AAG | GAG | TTC | AAA | TGC | AGG | GTC | AAC | AGT | GCA | GCT | TTC | CCT |

*Constant region*

|  | A | P | I | E | K | T | I | S | K | T | K | G | R | P | K |
|---|---|---|---|---|---|---|---|---|---|---|---|---|---|---|---|
| 1036 | GCC | CCC | ATC | GAG | AAA | ACC | ATC | TCC | AAA | ACC | AAA | GGC | AGA | CCG | AAG |

*Constant region*

|  | A | P | Q | V | Y | T | I | P | P | P | K | E | Q | M | A |
|---|---|---|---|---|---|---|---|---|---|---|---|---|---|---|---|
| 1081 | GCT | CCA | CAG | GTG | TAC | ACC | ATT | CCA | CCT | CCC | AAG | GAG | CAG | ATG | GCC |

*Constant region*

|  | K | D | K | V | S | L | T | C | M | I | T | D | F | F | P |
|---|---|---|---|---|---|---|---|---|---|---|---|---|---|---|---|
| 1126 | AAG | GAT | AAA | GTC | AGT | CTG | ACC | TGC | ATG | ATA | ACA | GAC | TTC | TTC | CCT |

FIG. 5A (continued)

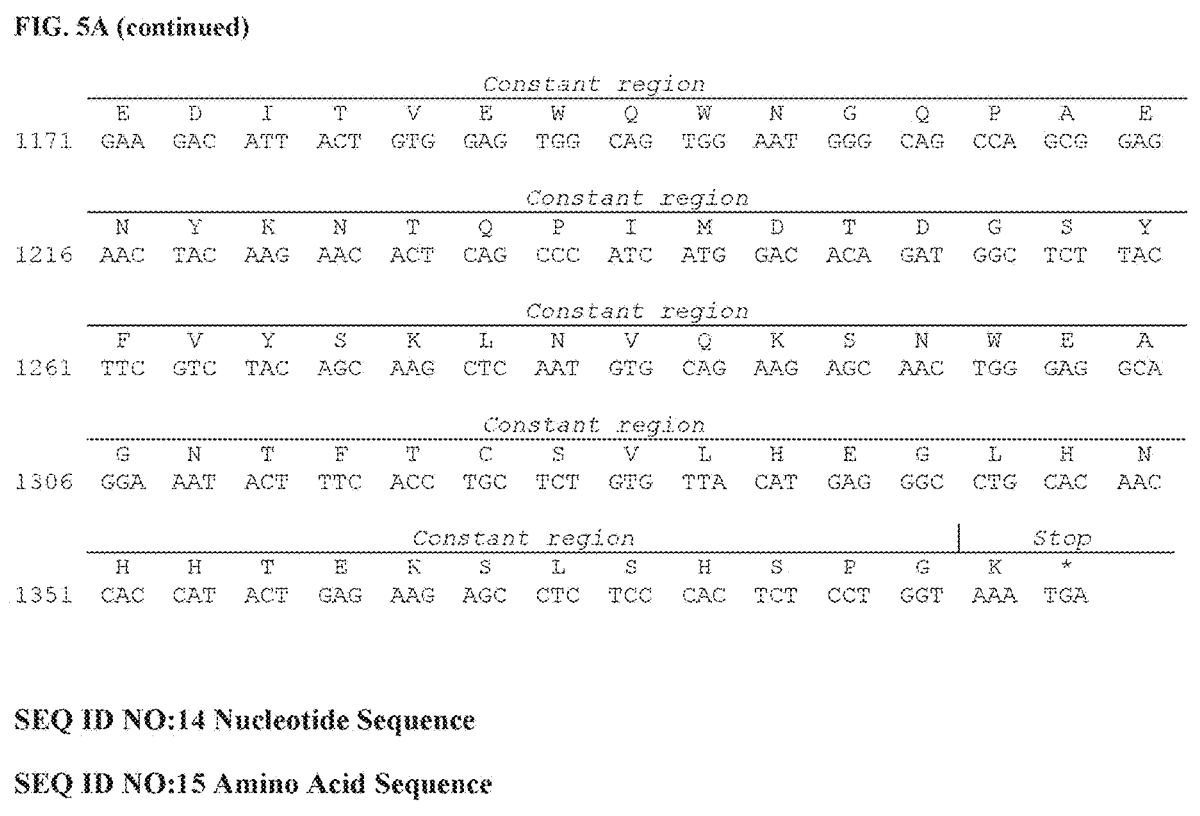

| | | | | | | | Constant region | | | | | | | |
|---|---|---|---|---|---|---|---|---|---|---|---|---|---|---|
| | E | D | I | T | V | E | W | Q | W | N | G | Q | P | A | E |
| 1171 | GAA | GAC | ATT | ACT | GTG | GAG | TGG | CAG | TGG | AAT | GGG | CAG | CCA | GCG | GAG |

| | | | | | | | Constant region | | | | | | | |
|---|---|---|---|---|---|---|---|---|---|---|---|---|---|---|
| | N | Y | K | N | T | Q | P | I | M | D | T | D | G | S | Y |
| 1216 | AAC | TAC | AAG | AAC | ACT | CAG | CCC | ATC | ATG | GAC | ACA | GAT | GGC | TCT | TAC |

| | | | | | | | Constant region | | | | | | | |
|---|---|---|---|---|---|---|---|---|---|---|---|---|---|---|
| | F | V | Y | S | K | L | N | V | Q | K | S | N | W | E | A |
| 1261 | TTC | GTC | TAC | AGC | AAG | CTC | AAT | GTG | CAG | AAG | AGC | AAC | TGG | GAG | GCA |

| | | | | | | | Constant region | | | | | | | |
|---|---|---|---|---|---|---|---|---|---|---|---|---|---|---|
| | G | N | T | F | T | C | S | V | L | H | E | G | L | H | N |
| 1306 | GGA | AAT | ACT | TTC | ACC | TGC | TCT | GTG | TTA | CAT | GAG | GGC | CTG | CAC | AAC |

| | | | | | | Constant region | | | | | | | Stop | |
|---|---|---|---|---|---|---|---|---|---|---|---|---|---|---|
| | H | H | T | E | K | S | L | S | H | S | P | G | K | * |
| 1351 | CAC | CAT | ACT | GAG | AAG | AGC | CTC | TCC | CAC | TCT | CCT | GGT | AAA | TGA |

SEQ ID NO:14 Nucleotide Sequence

SEQ ID NO:15 Amino Acid Sequence

FIG. 5B

N-Terminal
Glu Val Lys Leu Leu Glu Ser Gly Gly Gly Leu Val Gln Pro Gly Gly Ser Leu Lys Leu
1           5               10              15                  20

| CDR1
Ser Cys Ala Ala Ser Gly Phe Asp Phe Ser Arg Tyr Trp Met Ser Trp Val Arg Gln Ala
21          25              30              35                  40

| CDR2
Pro Gly Lys Gly Leu Glu Trp Ile Gly Glu Ile Asn Pro Thr Ser Ser Thr Ile Asn Phe
41          45              50              55                  60

Thr Pro Ser Leu Lys Asp Lys Val Phe Ile Ser Arg Asp Asn Ala Lys Asn Thr Leu Tyr
61          65              70              75                  80

| CDR3
Leu Gln Met Ser Lys Val Arg Ser Glu Asp Thr Ala Leu Tyr Tyr Cys Ala Arg Gly Asn
81          85              90              95                  100

Tyr Tyr Arg Tyr Gly Asp Ala Met Asp Tyr Trp Gly Gln Gly Thr Ser Val Thr Val Ser
101         105             110             115                 120

Ser Ala Lys Thr Thr Pro Pro Ser Val Tyr Pro Leu Ala Pro Gly Ser Ala Ala Gln Thr
121         125             130             135                 140

Asp Ser Met Val Thr Leu Gly Cys Leu Val Lys Gly Tyr Phe Pro Glu Pro Val Thr Val
141         145             150             155                 160

Thr Trp Asn Ser Gly Ser Leu Ser Ser Gly Val His Thr Phe Pro Ala Val Leu Gln Ser
161         165             170             175                 180

Asp Leu Tyr Thr Leu Ser Ser Ser Val Thr Val Pro Ser Ser Thr Trp Pro Ser Glu Thr
181         185             190             195                 200

Val Thr Cys Asn Val Ala His Pro Ala Ser Ser Thr Lys Val Asp Lys Lys Ile Val Pro
201         205             210             215                 220

Arg Asp Cys Gly Cys Lys Pro Cys Ile Cys Thr Val Pro Glu Val Ser Ser Val Phe Ile
221         225             230             235                 240

Phe Pro Pro Lys Pro Lys Asp Val Leu Thr Ile Thr Leu Thr Pro Lys Val Thr Cys Val
241         245             250             255                 260

FIG. 5B (continued)

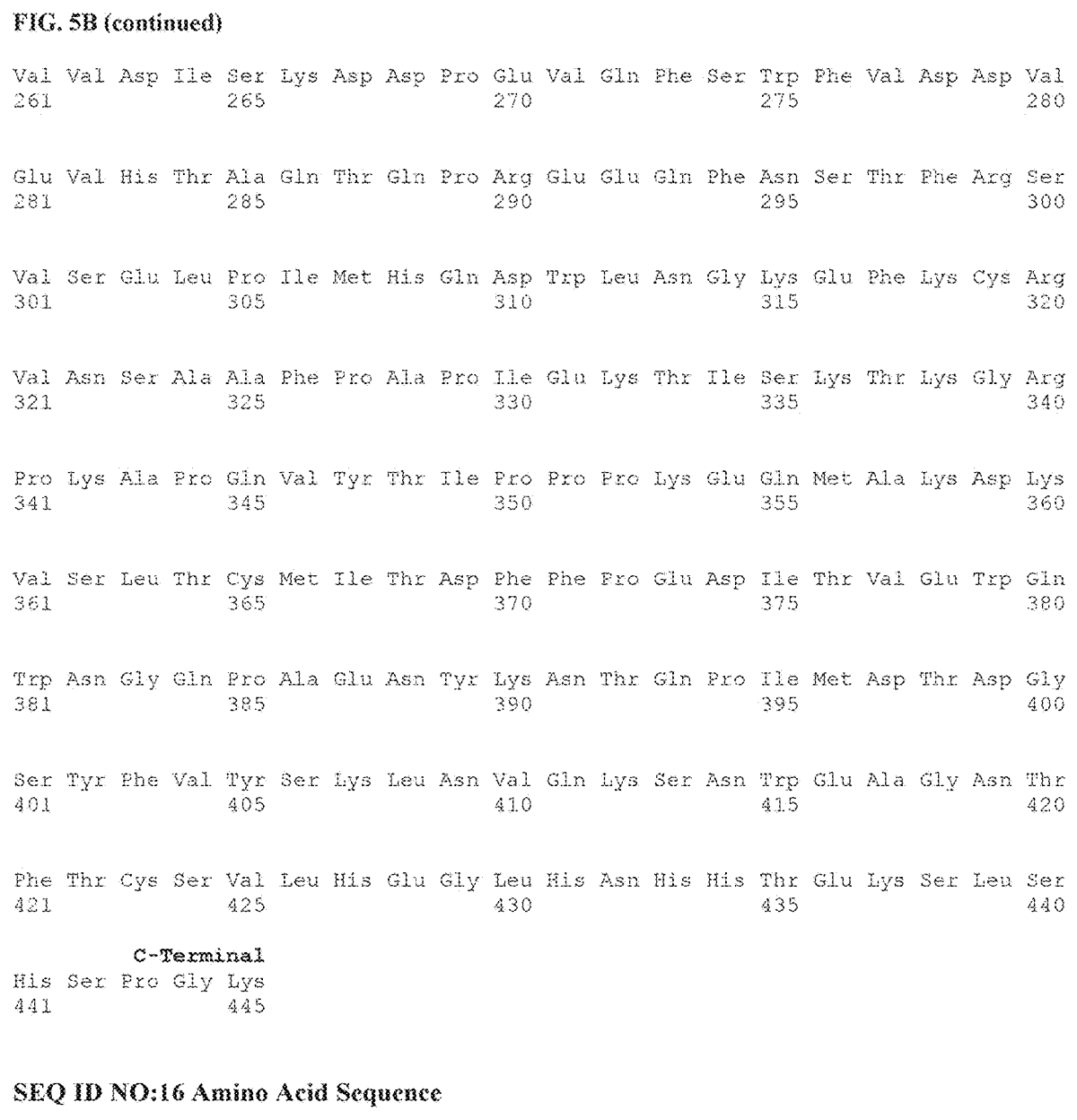

```
Val Val Asp Ile Ser Lys Asp Asp Pro Glu Val Gln Phe Ser Trp Phe Val Asp Asp Val
261             265             270             275             280

Glu Val His Thr Ala Gln Thr Gln Pro Arg Glu Glu Gln Phe Asn Ser Thr Phe Arg Ser
281             285             290             295             300

Val Ser Glu Leu Pro Ile Met His Gln Asp Trp Leu Asn Gly Lys Glu Phe Lys Cys Arg
301             305             310             315             320

Val Asn Ser Ala Ala Phe Pro Ala Pro Ile Glu Lys Thr Ile Ser Lys Thr Lys Gly Arg
321             325             330             335             340

Pro Lys Ala Pro Gln Val Tyr Thr Ile Pro Pro Pro Lys Glu Gln Met Ala Lys Asp Lys
341             345             350             355             360

Val Ser Leu Thr Cys Met Ile Thr Asp Phe Phe Pro Glu Asp Ile Thr Val Glu Trp Gln
361             365             370             375             380

Trp Asn Gly Gln Pro Ala Glu Asn Tyr Lys Asn Thr Gln Pro Ile Met Asp Thr Asp Gly
381             385             390             395             400

Ser Tyr Phe Val Tyr Ser Lys Leu Asn Val Gln Lys Ser Asn Trp Glu Ala Gly Asn Thr
401             405             410             415             420

Phe Thr Cys Ser Val Leu His Glu Gly Leu His Asn His His Thr Glu Lys Ser Leu Ser
421             425             430             435             440

C-Terminal
His Ser Pro Gly Lys
441             445
```

SEQ ID NO:16 Amino Acid Sequence

FIG. 6A

Human IgG1

Heavy Chain Constant Region

ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDE
LTKNQVSLTCLVKGFYPSDIAVEWESNGQPENNYKTTPPVLDSDGSFFLYSKLTVDKSRW
QQGNVFSCSVMHEALHNHYTQKSLSLSPGK (Sequence ID No: 17)

FIG. 6B

Human IgG2

Heavy Chain Constant Region

ASTKGPSVFPLAPCSRSTSESTAALGCLVKDYFPEPVTVSWNSGALTSGVHTFPAVLQSS
GLYSLSSVVTVPSSNFGTQTYTCNVDHKPSNTKVDKTVERKCCVECPPCPAPPVAGPSVF
LFPPKPKDTLMISRTPEVTCVVVDVSHEDPEVQFNWYVDGVEVHNAKTKPREEQFNSTFR
VVSVLTVVHQDWLNGKEYKCKVSNKGLPAPIEKTISKTKGQPREPQVYTLPPSREEMTKN
QVSLTCLVKGFYPSDISVEWESNGQPENNYKTTPPMLDSDGSFFLYSKLTVDKSRWQQGN
VFSCSVMHEALHNHYTQKSLSLSPGK (Sequence ID No: 18)

FIG. 6C

Human IgG4

Heavy Chain Constant Region

ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPSCPAPEFLGGPSV
FLFPPKPKDTLMISRTPEVTCVVVDVSQEDPEVQFNWYVDGVEVHNAKTKPREEQFNSTY
RVVSVLTVLHQDWLNGKEYKCKVSNKGLPSSIEKTISKAKGQPREPQVYTLPPSQEEMTK
NQVSLTCLVKGFYPSDIAVEWESNGQPENNYKTTPPVLDSDGSFFLYSRLTVDKSRWQEG
NVFSCSVMHEALHNHYTQKSLSLSLGK (Sequence ID No: 19)

FIG. 6D

Human IgG4 with S228P

Heavy Chain Constant Region

ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCP<u>P</u>CPAPEFLGGPSV
FLFPPKPKDTLMISRTPEVTCVVVDVSQEDPEVQFNWYVDGVEVHNAKTKPREEQFNSTY
RVVSVLTVLHQDWLNGKEYKCKVSNKGLPSSIEKTISKAKGQPREPQVYTLPPSQEEMTK
NQVSLTCLVKGFYPSDIAVEWESNGQPENNYKTTPPVLDSDGSFFLYSRLTVDKSRWQEG
NVFSCSVMHEALHNHYTQKSLSLSLGK (Sequence ID No: 20)

FIG. 6E

Human Kappa Light Chain Constant Region

RTVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC (Sequence ID No: 21)

Average % maximum values from two flow cytometry determinations of BC8 and BC8 DOTA binding to cytotrol cells Binding of 225Ac-BC8 and 225Ac-18B7 to cytotrol cells Binding of BC8-DOTA to H929 and U266 cells by Flow Cytometry Binding of Ac225 labeled antibodies to H929 and U266 cells Tumor volume, mm³

Days post treatment

- 0.3 µCi Ac-BC8
- untreated
- 0.3 µCi Ac-18B7
- cold BC8

Tumor volume, mm³

Days post treatment

- untreated
- 0.3 µCi Ac-BC8
- 0.3 µCi Ac-18B7
- cold BC8

SEQUENCE LISTING

<160> NUMBER OF SEQ ID NOS: 21

<210> SEQ ID NO 1
<211> LENGTH: 111
<212> TYPE: PRT
<213> ORGANISM: Murine

<400> SEQUENCE: 1

```
Asp Ile Ala Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Leu His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Glu Ile Lys
```

-continued

```
                100                 105                 110
```

<210> SEQ ID NO 2
<211> LENGTH: 123
<212> TYPE: PRT
<213> ORGANISM: Murine

<400> SEQUENCE: 2

```
Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Thr Ser Ser Thr Ile Asn Phe Thr Pro Ser Leu
    50                  55                  60

Lys Asp Lys Val Phe Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Gly Asn Tyr Tyr Arg Tyr Gly Asp Ala Met Asp Tyr Trp Gly
            100                 105                 110

Gln Gly Thr Ser Val Thr Val Ser Ser Ala Lys
        115                 120
```

<210> SEQ ID NO 3
<211> LENGTH: 15
<212> TYPE: PRT
<213> ORGANISM: Murine

<400> SEQUENCE: 3

```
Arg Ala Ser Lys Ser Val Ser Thr Ser Gly Tyr Ser Tyr Leu His
1               5                   10                  15
```

<210> SEQ ID NO 4
<211> LENGTH: 7
<212> TYPE: PRT
<213> ORGANISM: Murine

<400> SEQUENCE: 4

```
Leu Ala Ser Asn Leu Glu Ser
1               5
```

<210> SEQ ID NO 5
<211> LENGTH: 9
<212> TYPE: PRT
<213> ORGANISM: Murine

<400> SEQUENCE: 5

```
Gln His Ser Arg Glu Leu Pro Phe Thr
1               5
```

<210> SEQ ID NO 6
<211> LENGTH: 10
<212> TYPE: PRT
<213> ORGANISM: Murine

<400> SEQUENCE: 6

```
Gly Phe Asp Phe Ser Arg Tyr Trp Met Ser
1               5                   10
```

-continued

```
<210> SEQ ID NO 7
<211> LENGTH: 17
<212> TYPE: PRT
<213> ORGANISM: Murine

<400> SEQUENCE: 7

Glu Ile Asn Pro Thr Ser Ser Thr Ile Asn Phe Thr Pro Ser Leu Lys
1               5                   10                  15

Asp

<210> SEQ ID NO 8
<211> LENGTH: 12
<212> TYPE: PRT
<213> ORGANISM: Murine

<400> SEQUENCE: 8

Gly Asn Tyr Tyr Arg Tyr Gly Asp Ala Met Asp Tyr
1               5                   10

<210> SEQ ID NO 9
<211> LENGTH: 7
<212> TYPE: PRT
<213> ORGANISM: Murine

<400> SEQUENCE: 9

Asp Ile Ala Leu Thr Gln Ser
1               5

<210> SEQ ID NO 10
<211> LENGTH: 7
<212> TYPE: PRT
<213> ORGANISM: Murine

<400> SEQUENCE: 10

Glu Val Lys Leu Leu Glu Ser
1               5

<210> SEQ ID NO 11
<211> LENGTH: 717
<212> TYPE: DNA
<213> ORGANISM: Murine

<400> SEQUENCE: 11
atggagacag acacactcct gttatgggta ctgctgctct gggttccagg ttccactggt        60
gacattgcgc tgacacagtc tcctgcttcc ttagctgtat ctctgggaca gagggccacc       120
atctcatgca gggccagcaa aagtgtcagt acatctggct atagttatct gcactggtac       180
caacagaaac aggacagcc acccaaactc ctcatctatc ttgcatccaa cctagaatct       240
ggggtccctg ccaggttcag tggcagtggg tctgggacag acttcaccct caacatccat       300
cctgtggagg aggaggatgc tgcaacctat tactgtcagc acagtaggga gcttccattc       360
acgttcggct cggggacaaa gttggaaata aaacgggctg atgctgcacc aactgtatcc       420
atcttcccac catccagtga gcagttaaca tctggaggtg cctcagtcgt gtgcttcttg       480
aacaacttct accccaaaga catcaatgtc aagtggaaga ttgatggcag tgaacgacaa       540
aatggcgtcc tgaacagttg gactgatcag gacagcaaag acagcaccta cagcatgagc       600
agcaccctca cgttgaccaa ggacgagtat gaacgacata cagctatac ctgtgaggcc       660 actcacaaga tcaacttc acccattgtc aagagcttca acaggaatga gtgttag        717

<210> SEQ ID NO 12
```

```
<211> LENGTH: 238
<212> TYPE: PRT
<213> ORGANISM: Murine

<400> SEQUENCE: 12

Met Glu Thr Asp Thr Leu Leu Leu Trp Val Leu Leu Leu Trp Val Pro
1               5                   10                  15

Gly Ser Thr Gly Asp Ile Ala Leu Thr Gln Ser Pro Ala Ser Leu Ala
            20                  25                  30

Val Ser Leu Gly Gln Arg Ala Thr Ile Ser Cys Arg Ala Ser Lys Ser
        35                  40                  45

Val Ser Thr Ser Gly Tyr Ser Tyr Leu His Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln His Ser Arg Glu Leu Pro Phe Thr Phe Gly Ser Gly Thr Lys Leu
            115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
            195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 13
<211> LENGTH: 218
<212> TYPE: PRT
<213> ORGANISM: Murine

<400> SEQUENCE: 13

Asp Ile Ala Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Leu His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Glu Ile Lys Arg
            100                 105                 110
```

-continued

```
Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
        130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
                180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
        210                 215
```

```
<210> SEQ ID NO 14
<211> LENGTH: 1392
<212> TYPE: DNA
<213> ORGANISM: Murine

<400> SEQUENCE: 14
atggattttg ggctgatttt ttttattgtt gctcttttaa aaggggtcca gtgtgaggtg      60
aagcttctcg agtctggagg tggcctggtg cagcctggag gatccctgaa actctcctgt     120
gcagcctcag gattcgattt cagtagatac tggatgagtt gggtccggca ggctccaggg     180
aaagggctag aatggattgg agagattaat ccaactagca gtacgataaa ctttacgcca     240
tctctaaagg ataaagtctt catctccaga gacaacgcca aaaatacgct gtacctgcaa     300
atgagcaaag tgagatctga ggacacagcc ctttattact gtgcaagagg gaactactat     360
aggtacggag atgctatgga ctactggggt caaggaacct cagtcaccgt ctcctcagcc     420
aaaacgacac cccatctgt ctatccactg gcccctggat ctgctgccca aactaactcc      480
atggtgaccc tgggatgcct ggtcaagggc tatttccctg agccagtgac agtgacctgg     540
aactctggat ccctgtccag cggtgtgcac accttccag ctgtcctgca gtctgacctc      600
tacactctga gcagctcagt gactgtcccc tccagcacct ggcccagcga ccgtcacc       660 tgcaacgttg cccacccggc cagcagcacc aaggtggaca gaaaaattgt gcccagggat     720
tgtggttgta agccttgcat atgtacagtc ccagaagtat catctgtctt catcttcccc     780
ccaaagccca aggatgtgct caccattact ctgactccta aggtcacgtg tgttgtggta     840
gacatcagca aggatgatcc cgaggtccag ttcagctggt ttgtagatga tgtggaggtg     900
cacacagctc agacgcaacc ccgggaggag cagttcaaca gcactttccg ctcagtcagt     960
gaacttccca tcatgcacca ggactggctc aatggcaagg agttcaaatg cagggtcaac    1020
agtgcagctt ccctgccccc catcgagaaa accatctcca aaaccaaagg cagaccgaag    1080
gctccacagg tgtacaccat tccacctccc aaggagcaga tggccaagga taaagtcagt    1140
ctgacctgca tgataacaga cttcttccct gaagacatta ctgtggagtg gcagtggaat    1200
gggcagccag cggagaacta caagaacact cagcccatca tggacacaga tggctcttac    1260
ttcgtctaca gcaagctcaa tgtgcagaag agcaactggg aggcaggaaa tactttcacc    1320
tgctctgtgt acatgagggg cctgcacaac caccatactg agaagagcct ctcccactct    1380
cctggtaaat ga                                                        1392
```

-continued

```
<210> SEQ ID NO 15
<211> LENGTH: 463
<212> TYPE: PRT
<213> ORGANISM: Murine

<400> SEQUENCE: 15

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
            35                  40                  45

Arg Tyr Trp Met Ser Trp Val Arg Gln Ala Pro Gly Lys Gly Leu Glu
        50                  55                  60

Trp Ile Gly Glu Ile Asn Pro Thr Ser Ser Thr Ile Asn Phe Thr Pro
65                  70                  75                  80

Ser Leu Lys Asp Lys Val Phe Ile Ser Arg Asp Asn Ala Lys Asn Thr
                85                  90                  95

Leu Tyr Leu Gln Met Ser Lys Val Arg Ser Glu Asp Thr Ala Leu Tyr
            100                 105                 110

Tyr Cys Ala Arg Gly Asn Tyr Tyr Arg Tyr Gly Asp Ala Met Asp Tyr
            115                 120                 125

Trp Gly Gln Gly Thr Ser Val Thr Val Ser Thr Pro Ser Leu Lys Asp
        130                 135                 140

Lys Val Phe Ile Ser Arg Asp Asn Ala Lys Asn Thr Leu Tyr Leu Gln
145                 150                 155                 160

Met Ser Lys Val Arg Ser Glu Asp Thr Ala Leu Tyr Tyr Cys Ala Arg
                165                 170                 175

Gly Asn Tyr Tyr Arg Tyr Gly Asp Ala Met Asp Tyr Trp Gly Gln Gly
            180                 185                 190

Thr Ser Val Thr Val Ser Asp Leu Tyr Thr Leu Ser Ser Ser Val Thr
            195                 200                 205

Val Pro Ser Ser Thr Trp Pro Ser Glu Thr Val Thr Cys Asn Val Ala
        210                 215                 220

His Pro Ala Ser Ser Thr Lys Val Asp Lys Lys Ile Val Pro Arg Asp
225                 230                 235                 240

Cys Gly Cys Lys Pro Cys Ile Cys Thr Val Pro Glu Val Ser Ser Val
                245                 250                 255

Phe Ile Phe Pro Pro Lys Pro Lys Asp Val Leu Thr Ile Thr Leu Thr
            260                 265                 270

Pro Lys Val Thr Cys Val Val Val Asp Ile Ser Lys Asp Asp Pro Glu
            275                 280                 285

Val Gln Phe Ser Trp Phe Val Asp Asp Val Glu Val His Thr Ala Gln
        290                 295                 300

Thr Gln Pro Arg Glu Glu Gln Phe Asn Ser Thr Phe Arg Ser Val Ser
305                 310                 315                 320

Glu Leu Pro Ile Met His Gln Asp Trp Leu Asn Gly Lys Glu Phe Lys
                325                 330                 335

Cys Arg Val Asn Ser Ala Ala Phe Pro Ala Pro Ile Glu Lys Thr Ile
            340                 345                 350

Ser Lys Thr Lys Gly Arg Pro Lys Ala Pro Gln Val Tyr Thr Ile Pro
            355                 360                 365

Pro Pro Lys Glu Gln Met Ala Lys Asp Lys Val Ser Leu Thr Cys Met
        370                 375                 380
```

-continued

```
Ile Thr Asp Phe Phe Pro Glu Asp Ile Thr Val Glu Trp Gln Trp Asn
385                 390                 395                 400

Gly Gln Pro Ala Glu Asn Tyr Lys Asn Thr Gln Pro Ile Met Asp Thr
                405                 410                 415

Asp Gly Ser Tyr Phe Val Tyr Ser Lys Leu Asn Val Gln Lys Ser Asn
                420                 425                 430

Trp Glu Ala Gly Asn Thr Phe Thr Cys Ser Val Leu His Glu Gly Leu
            435                 440                 445

His Asn His His Thr Glu Lys Ser Leu Ser His Ser Pro Gly Lys
        450                 455                 460
```

<210> SEQ ID NO 16
<211> LENGTH: 445
<212> TYPE: PRT
<213> ORGANISM: Murine

<400> SEQUENCE: 16

```
Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Thr Ser Ser Thr Ile Asn Phe Thr Pro Ser Leu
    50                  55                  60

Lys Asp Lys Val Phe Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
            85                  90                  95

Ala Arg Gly Asn Tyr Tyr Arg Tyr Gly Asp Ala Met Asp Tyr Trp Gly
            100                 105                 110

Gln Gly Thr Ser Val Thr Val Ser Thr Pro Ser Leu Lys Asp Lys Val
            115                 120                 125

Phe Ile Ser Arg Asp Asn Ala Lys Asn Thr Leu Tyr Leu Gln Met Ser
    130                 135                 140

Lys Val Arg Ser Glu Asp Thr Ala Leu Tyr Tyr Cys Ala Arg Gly Asn
145                 150                 155                 160

Tyr Tyr Arg Tyr Gly Asp Ala Met Asp Tyr Trp Gly Gln Gly Thr Ser
            165                 170                 175

Val Thr Val Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300
```

```
Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
                340                 345                 350

Lys Glu Gln Met Ala Lys Asp Lys Val Ser Leu Thr Cys Met Ile Thr
                355                 360                 365

Asp Phe Phe Pro Glu Asp Ile Thr Val Glu Trp Gln Trp Asn Gly Gln
        370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
                420                 425                 430

His His Thr Glu Lys Ser Leu Ser His Ser Pro Gly Lys
                435                 440                 445

<210> SEQ ID NO 17
<211> LENGTH: 330
<212> TYPE: PRT
<213> ORGANISM: Human

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
```

-continued

```
             225                    230                    235                    240

Leu Thr Lys Asn Gln Val Ser Leu Thr Cys Leu Val Lys Gly Phe Tyr
                         245                    250                    255

Pro Ser Asp Ile Ala Val Glu Trp Glu Ser Asn Gly Gln Pro Glu Asn
                         260                    265                    270

Asn Tyr Lys Thr Thr Pro Pro Val Leu Asp Ser Asp Gly Ser Phe Phe
                         275                    280                    285

Leu Tyr Ser Lys Leu Thr Val Asp Lys Ser Arg Trp Gln Gln Gly Asn
             290                    295                    300

Val Phe Ser Cys Ser Val Met His Glu Ala Leu His Asn His Tyr Thr
305                      310                    315                    320

Gln Lys Ser Leu Ser Leu Ser Pro Gly Lys
                         325                    330

<210> SEQ ID NO 18
<211> LENGTH: 326
<212> TYPE: PRT
<213> ORGANISM: Human

<400> SEQUENCE: 18

Ala Ser Thr Lys Gly Pro Ser Val Phe Pro Leu Ala Pro Cys Ser Arg
1                   5                    10                     15

Ser Thr Ser Glu Ser Thr Ala Ala Leu Gly Cys Leu Val Lys Asp Tyr
                    20                   25                     30

Phe Pro Glu Pro Val Thr Val Ser Trp Asn Ser Gly Ala Leu Thr Ser
             35                     40                     45

Gly Val His Thr Phe Pro Ala Val Leu Gln Ser Ser Gly Leu Tyr Ser
         50                     55                     60

Leu Ser Ser Val Val Thr Val Pro Ser Ser Asn Phe Gly Thr Gln Thr
65                   70                     75                     80

Tyr Thr Cys Asn Val Asp His Lys Pro Ser Asn Thr Lys Val Asp Lys
                    85                     90                     95

Thr Val Glu Arg Lys Cys Cys Val Glu Cys Pro Pro Cys Pro Ala Pro
                    100                    105                    110

Pro Val Ala Gly Pro Ser Val Phe Leu Phe Pro Pro Lys Pro Lys Asp
             115                    120                    125

Thr Leu Met Ile Ser Arg Thr Pro Glu Val Thr Cys Val Val Val Asp
         130                    135                    140

Val Ser His Glu Asp Pro Glu Val Gln Phe Asn Trp Tyr Val Asp Gly
145                    150                    155                    160

Val Glu Val His Asn Ala Lys Thr Lys Pro Arg Glu Glu Gln Phe Asn
                    165                    170                    175

Ser Thr Phe Arg Val Val Ser Val Leu Thr Val Val His Gln Asp Trp
                    180                    185                    190

Leu Asn Gly Lys Glu Tyr Lys Cys Lys Val Ser Asn Lys Gly Leu Pro
             195                    200                    205

Ala Pro Ile Glu Lys Thr Ile Ser Lys Thr Lys Gly Gln Pro Arg Glu
             210                    215                    220

Pro Gln Val Tyr Thr Leu Pro Pro Ser Arg Glu Glu Met Thr Lys Asn
225                    230                    235                    240

Gln Val Ser Leu Thr Cys Leu Val Lys Gly Phe Tyr Pro Ser Asp Ile
                    245                    250                    255

Ser Val Glu Trp Glu Ser Asn Gly Gln Pro Glu Asn Asn Tyr Lys Thr
             260                    265                    270
```

-continued

```
Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 19
<211> LENGTH: 327
<212> TYPE: PRT
<213> ORGANISM: Human

<400> SEQUENCE: 19

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320
```

-continued

```
Leu Ser Leu Ser Leu Gly Lys
            325

<210> SEQ ID NO 20
<211> LENGTH: 327
<212> TYPE: PRT
<213> ORGANISM: Human

<400> SEQUENCE: 20

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 21
<211> LENGTH: 107
<212> TYPE: PRT
```

-continued

```
<213> ORGANISM: Human

<400> SEQUENCE: 21

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
            100                 105
```

RADIOLABELING OF ANTI-CD45 IMMUNOGLOBULIN AND METHODS OF USE THEREOF

CROSS-REFERENCE TO RELATED APPLICATIONS

This application is a U.S. national stage filing under 35 U.S.C. § 371 of International Application No. PCT/US2020/051324 filed on Sep. 17, 2020, which claims priority to U.S. Provisional Patent Application Ser. No. 62/901,290 filed Sep. 17, 2019, which are incorporated herein in its entirety.

REFERENCE TO A SEQUENCE LISTING

This application contains a sequence listing incorporated herein as a supplemental file submitted via EFS and presented in compliance with 37 CFR § 1.52(e)(5) and Rule 13ter.1(a), and which lists sequences identical to the sequences found within this specification.

TECHNICAL FIELD

The present disclosure relates to methods for radiolabeling monoclonal antibodies against CD45, compositions comprising the radiolabeled monoclonal antibodies against CD45, and methods for use of the radiolabeled anti-CD45 antibodies for the treatment of malignant and non-malignant hematological diseases.

BACKGROUND

CD45 is a type I transmembrane glycoprotein that is a member of the protein tyrosine phosphatase (PTP) family and plays a key role in T-cell and B-cell receptor signal transduction. CD45 controls activation of the Src family protein-tyrosine kinases Lck and Fyn. CD45 deficiency results in T- and B-lymphocyte dysfunction in the form of severe combined immune deficiency. It is also reported to play a significant role in autoimmune diseases and cancer as well as in infectious diseases including fungal infections (Penninger et al., 2001, *CD45: new jobs for an old acquaintance*, Nat. Immunol., 2(5):389-396), and metabolic disorders. The primary ligands described for CD45 include galectin-1, CD1, CD2, CD3, CD4, TCR, CD22 and Thy-1.

Also known as leukocyte common antigen (LCA), T200, or Ly-5, CD45 consists of two intracellular phosphatase domains, a transmembrane domain, and an extracellular domain. While both intracellular phosphatase domains are required for appropriate phosphate activity, only one has intrinsic kinase activity (Desai et al., 1994, *The catalytic activity of the CD45 membrane-proximal phosphatase domain is required for TCR signaling and regulation*, EMBO J. 13:4002-4010).

In general, all cells of hematopoietic origin, with the exception of mature erythrocytes and platelets, express at least one isoform of CD45. High expression of CD45 is seen with most acute lymphoid and myeloid leukemias. Since CD45 is not found on tissues of non-hematopoietic origin, its specific expression in leukemia has made it a good target for developing therapeutics, including immunotherapeutics. For example, CD45 is expressed at a density of approximately 200,000 to 300,000 sites per cell on circulating leukocytes and malignant B cells.

One particular anti-CD45 antibody, BC8, has been explored as a candidate immunotherapeutic agent alone and in combination with chemotherapy or total body irradiation in the treatment of leukemias. Anti-CD45 antibody-based lymphodepletion is also known (see, e.g., Louis, et al., 2009, Blood, 113:2442-2450). However, this approach had shortcomings. For example, in the Louis, et al. study, eight patients were lymphodepleted with anti-CD45 antibody and showed an increase in peripheral blood frequency of desired T-cells after infusion. However, only three patients had clinical benefits, and only one had a complete response.

CD45 exists as multiple isoforms due to alternative splicing of three of the 34 exons (exons 4, 5, and 6, designated A, B, and C; see FIG. 1) in the extracellular domain (Streuli et al., 1987 *Differential usage of three exons generates at least five different mRNAs encoding human leukocyte common antigens*, J. Exp. Med. 166:1548-1566; Chang et al., 2016, *Initiation of T cell signaling by CD45 segregation at 'close-contacts'*, Nat. Immunol. 17(5):574-582). These three exons encode multiple sites of O-linked glycosylation and are variably modified by sialic acid. As a result, the various isoforms differ substantially in size (391 to 552 amino acids; molecular weight ranging from 180-240 kDa), shape, and negative charge. The remaining membrane proximal extracellular domain is heavily N-glycosylated and contains a cysteine-rich spacer region followed by three fibronectin type III repeats.

While eight isoforms of CD45 are possible, only six are identified in humans: RO (absent all three exons), RA (exon A), RB (exon B), RAB (exons A and B), RBC (exons B and C), and RABC (exons A, B, and C). These different isoforms are differentially expressed on subpopulations of B- and T-cell lymphocytes and are specific to the activation and maturation state of the cell. For example, CD45-RA and CD45-RB are expressed on naïve T-cells, while CD45-RO is expressed on activated T-cells, some B-cell subsets, activated monocytes/macrophages, and granulocytes, and CD45-RABC is preferentially expressed on B-cells (Hermiston et al., 2003, *CD45: A critical regulator of signaling thresholds in immune cells*, Ann. Rev. Immunol., 21:107-137).

Antibodies that selectively recognize various isoforms of CD45 have been identified. In addition, monoclonal antibodies (mAbs) that bind an epitope common to all the different isoforms have also been identified. For example, the anti-CD45 murine antibody BC8 recognizes all human isoforms of the CD45 antigen.

While the use of BC8 labelled with Iodine-131 ($^{131}$I) for the treatment of subjects needing bone marrow transplant has been explored (see International Publication No. WO 2017/155937, incorporated herein by reference in its entirety), there is still a need for compositions and methods of their use for the treatment of malignant and non-malignant hematological diseases. Specifically, there is a need for a therapeutic composition and methods that (i) employ an agent that is more specific than a chemotherapeutic, (ii) is potent enough to be effective at a low dose, and (iii) spares at least some types of hematopoietic stem cells from significant depletion.

SUMMARY OF THE INVENTION

The present disclosure exploits the pan-specific nature of the BC8 monoclonal antibody to provide compositions and methods useful for depletion, reversible immunosuppression, and/or ablation of specific cell populations, and further, methods for treating certain malignant and non-malignant hematological diseases using these compositions and methods.

The present disclosure provides compositions and methods of their use for the treatment of various disorders of the hematopoietic system, as well as metabolic disorders, cancers, and autoimmune diseases, among others. The disclosure additionally features methods for conditioning a patient prior to receiving hematopoietic stem cell transplant therapy so as to promote the engraftment of hematopoietic stem cell grafts. The patient may be one that is suffering from one or more blood disorders, such as a hemoglobinopathy or other hematopoietic pathology. The patient may be one that is in need of hematopoietic stem cell transplantation.

As described herein, hematopoietic stem cells are capable of differentiating into a multitude of cell types in the hematopoietic lineage and can be administered to a patient in order to populate or re-populate a cell type that is deficient in the patient. The present disclosure features methods of treating a patient with a radiolabeled antibody, specifically an actinium-225 ($^{225}$Ac) or lutetium-177 ($^{177}$Lu) labelled anti-CD45-immunoglobulin, which is capable of targeting hematopoietic cells to (i) directly treat a disease such as a blood disorder, metabolic disease, cancer, or autoimmune disease, among others described herein, by selectively depleting, reversibly suppressing, or ablating a population of cells that express CD45, such as an aberrant blood cell, cancer cell, or autoimmune cell, and/or (ii) deplete, reversibly suppress, or ablate a population of endogenous hematopoietic stem cells within the patient.

The former activity enables the direct treatment of a wide range of disorders associated with a cell of the hematopoietic lineage, such as a leukemic cell or a lymphoma cell, of either B or T cell lineage, an autoimmune lymphocyte, such as a T-cell that expresses a T-cell receptor that cross-reacts with a self-antigen, among other cell types. The latter activity, the selective depletion, reversible suppression, or ablation of hematopoietic stem cells, in turn creates a vacancy that can subsequently be filled by transplantation of an exogenous (for instance, an autologous, allogeneic, or syngeneic) hematopoietic stem cell graft.

The present disclosure thus provides methods for treating a variety of non-cancerous hematopoietic conditions, such as hemoglobinopathies (e.g., sickle cell disease or SCD, and β-thalassemia), congenital immunodeficiencies (e.g., severe combined immunodeficiency or SCID, Fanconi's anemia, Wiskott-Aldrich syndrome, Diamond-Blackfan anemia, and Schwachman-Diamond syndrome, adenosine deaminase deficiency), and viral infections (e.g., HIV infection and acquired immune deficiency syndrome). The present disclosure further provides methods for treating a cancerous disorder, such as a hematological cancer or a solid tumor. Exemplary hematological cancers include acute myeloid leukemia, acute lymphoid leukemia, chronic myeloid leukemia, chronic lymphoid leukemia, multiple myeloma, diffuse large B-cell lymphoma, and non-Hodgkin's lymphoma.

Accordingly, the present disclosure relates to a stabilized composition comprising an isolated anti-CD45 immunoglobulin (e.g., BC8 mAb clone) in its actinium-225 ($^{225}$Ac) or lutetium-177 ($^{177}$Lu) radiolabeled form, and therapeutic uses thereof for the treatment of malignant and non-malignant hematological diseases and disorders. With its ability to bind all isoforms of the CD45 antigen in humans, the BC8 antibody is expected to accumulate a therapeutically high radiation dose specifically and preferentially on high-density CD45 antigen-bearing cells.

As such, this disclosure also relates to methods for radiolabeling an anti-CD45 immunoglobulin such as the BC8 antibody with radionuclide such as $^{225}$Ac or $^{177}$Lu. According to certain aspects, the BC8 antibody is conjugated to a chelator such as S-2-(4-Isothiocyanatobenzyl)-1, 4,7,10 tetraazacyclododecanetetraacetic acid (p-SCN-Bn-DOTA; referred to as DOTA) to form DOTA-BC8, and radiolabeled with a radionuclide such as $^{225}$Ac to form the $^{225}$Ac-DOTA-BC8 (i.e., $^{225}$Ac-BC8) or $^{177}$Lu to provide $^{177}$Lu-DOTA-BC8 (i.e., $^{177}$Lu-BC8).

The $^{225}$Ac-BC8 or $^{177}$Lu-BC8 may be provided as a stabilized formulation comprising one or more pharmaceutically acceptable carriers, salts, or excipients. Certain exemplary carriers or excipients include saline, phosphate buffered saline (e.g., 50 mM PBS buffer, pH 7), and/or 0.5% to 5.0% (w/v) of one or more of ascorbic acid, polyvinylpyrrolidone (PVP), human serum albumin (HSA), a water-soluble salt of HSA, and mixtures thereof.

The BC8 antibody may comprise a light chain variable domain having the amino acid sequence as set forth in SEQ ID NO:1, or a heavy chain variable domain having an N-terminal amino acid sequence as set forth in SEQ ID NO:9. The BC8 antibody may comprise a light chain variable domain having at least one complementarity determining region (CDR) with the amino acid sequence as set forth in SEQ ID NO:3, SEQ ID NO:4, and SEQ ID NO:5. The BC8 antibody may comprise a light chain having the amino acid sequence as set for the in SEQ ID NO:12 or SEQ ID NO:13.

The BC8 antibody may comprise a heavy chain variable domain having the amino acid sequence as set forth in SEQ ID NO:2, or a heavy chain variable domain having an N-terminal amino acid sequence as set forth in SEQ ID NO:10. The BC8 antibody may comprise a heavy chain variable domain having at least one complementarity determining region (CDR) with the amino acid sequence as set forth in SEQ ID NO:6, SEQ ID NO:7, and SEQ ID NO:8. The BC8 antibody may comprise a heavy chain having the amino acid sequence as set for the in SEQ ID NO:15 or SEQ ID NO:16.

According to certain aspects, the BC8 antibody comprises a heavy chain having the amino acid sequence set forth in SEQ ID NO:15 or 16, wherein the amino acid at position 141 (relative to the N-terminal amino acid) is either an ASP or an ASN. A ratio of ASP:ASN at position 141 in a population of BC8 proteins may be within the range 1:99 to 99:1, such as 10:90 to 90:10.

According to certain aspects, the BC8 antibody comprises a heavy chain variable domain having the amino acid sequence as set forth in SEQ ID NO:2, or a heavy chain variable domain having an N-terminal amino acid sequence as set forth in SEQ ID NO:10, wherein the amino acid at position 141 (relative to the N-terminal amino acid) of the heavy chain is either an ASP or an ASN, with a ratio of ASP:ASN in a population of BC8 proteins within the range 1:99 to 99:1, such as 10:90 to 90:10.

According to certain aspects, any of the BC8 antibodies indicated above, i.e., those including one or more of SEQ ID NOS:1-10 may be a chimeric or humanized antibody, i.e., BC8c. The BC8c antibody may comprise a human IgG1, IgG2, or IgG4 heavy chain constant region having the amino acid sequence as set forth in SEQ ID NOS:17-19, respectively, a human IgG4 heavy chain constant region having the amino acid sequence as set forth in SEQ ID NO:20 (includes the mutation S228P), and/or a human kappa light chain constant region having the amino acid sequence as set forth in SEQ ID NO:21.

This disclosure provides methods for directly treating a subject afflicted with a CD45 positive hematological malignancy comprising administering to the subject an effective amount of $^{225}$Ac-BC8 or $^{177}$Lu-BC8 as a low dose single therapy agent alone or in combination with other therapies.

This disclosure provides methods for directly treating a subject afflicted with a CD45 positive hematological malignancy comprising administering to the subject an effective amount of $^{225}$Ac-BC8 or $^{177}$Lu-BC8 as a low dose single therapy agent alone or in combination with other therapies with stem cell support.

The present disclosure relates to methods for depleting, reversibly suppressing, or ablating a subject's hematopoietic stem cells comprising administering to the subject an effective amount of $^{225}$Ac-BC8 or $^{177}$Lu-BC8.

The present disclosure provides methods for depleting or reversibly suppressing circulating tumor cells (e.g., as found in leukemia, lymphoma, myeloma, MDS) by administering to the subject an effective amount of $^{225}$Ac-BC8 or $^{177}$Lu-BC8 at a dose that does not myeloablate, and thus does not irreversibly deplete hematopoietic stem cells. Such cells may comprise any of, at least, regulatory T cells, myeloid derived suppressor cells, tumor associated macrophages, activated macrophages secreting IL-1 and/or IL-6, and combinations thereof.

This disclosure further provides methods for depleting, reversibly suppressing, or ablating a subject's lymphocytes comprising administering to the subject an effective amount of $^{225}$Ac-BC8 or $^{177}$Lu-BC8.

This disclosure also provides methods for treating a subject afflicted with a non-cancerous disorder comprising administering to the subject an amount of $^{225}$Ac-BC8 or $^{177}$Lu-BC8 effective to deplete, reversibly suppress, or ablate the subject's hematopoietic stem cells. According to certain aspects, the disorder is treatable via genetically edited cell therapy, and the method further comprises performing the therapy on the subject to treat the subject's disorder after administration of the $^{225}$Ac-BC8 or $^{177}$Lu-BC8. According to certain aspects, the disorder is SCD and the therapy is genetically edited β-globin hematopoietic stem cell therapy. According to certain aspects, the disorder is SCID and the therapy is genetically edited hematopoietic stem cell therapy, wherein the edited gene is the common gamma chain (γc) gene, the adenosine deaminase (ADA) gene and/or the Janus kinase 3 (JAK3) gene. The stem cell therapy can be allogenic or autologous, for example.

This disclosure also provides methods for treating a subject afflicted with a cancerous disorder treatable via genetically edited cell therapy comprising (i) administering to the subject an amount of $^{225}$Ac-BC8 or $^{177}$Lu-BC8 effective to deplete, reversibly suppress, or ablate the subject's hematopoietic stem cells, and (ii) after a suitable time period, performing the therapy on the subject to treat the subject's disorder. According to certain aspects, the therapy suitable to treat the subject's disorder may be a bone marrow transplant, or an adoptive cell therapy.

Finally, this disclosure provides an article of manufacture comprising (a) a radiolabeled anti-CD45 antibody such as $^{225}$Ac-BC8 or $^{177}$Lu-BC8, and (b) a label instructing the user to administer to a subject an amount of the antibody effective to deplete the subject's hematopoietic stem cells.

BRIEF DESCRIPTION OF THE DRAWINGS

FIG. 2 provides the protein sequence of the complementarity determining regions (CDRs), framework regions and variable domain sequences of the light chain (VL) and the heavy chain (VH) of the anti-CD45 mAb BC8. The CDRs are in bold and underlined (SEQ ID NOS: 1 and 2).

FIG. 3 provides the CDRs and the N-terminal protein sequences of the light chain and the heavy chain of the anti-CD45 mAb BC8 (SEQ ID NOS: 3-10).

FIG. 4A provides the entire nucleotide (SEQ ID NO:11) and amino acid (SEQ ID NO:12) sequence of the light chain of the anti-CD45 mAb BC8.

FIG. 4B provides the amino acid (SEQ ID NO:13) sequence of the light chain of the anti-CD45 mAb BC8 without the leader sequence.

FIG. 5A provides the entire nucleotide (SEQ ID NO:14) and amino acid (SEQ ID NO:15) sequence of the heavy chain of the anti-CD45 mAb BC8, wherein the asparagine at position 141 (from the n terminal of the protein sequence) is found to be deaminated to aspartic acid in at least a portion of the protein population.

FIG. 5B provides the amino acid (SEQ ID NO:16) sequence of the heavy chain of the anti-CD45 mAb BC8 without the leader sequence, wherein the asparagine at position 141 (from the n terminal of the protein sequence) is found to be deaminated to aspartic acid in at least a portion of the protein population.

FIGS. 6A-6C provide the amino acid sequences SEQ ID NOS.17-19 of the human heavy chain constant region, respectively.

FIG. 6D provides the amino acid sequence (SEQ ID NO: 20) of the human heavy chain constant region comprising the mutation S228P.

FIG. 6E provides the amino acid sequence (SEQ ID NO:21) of the human kappa light chain constant region.

Figure 1:
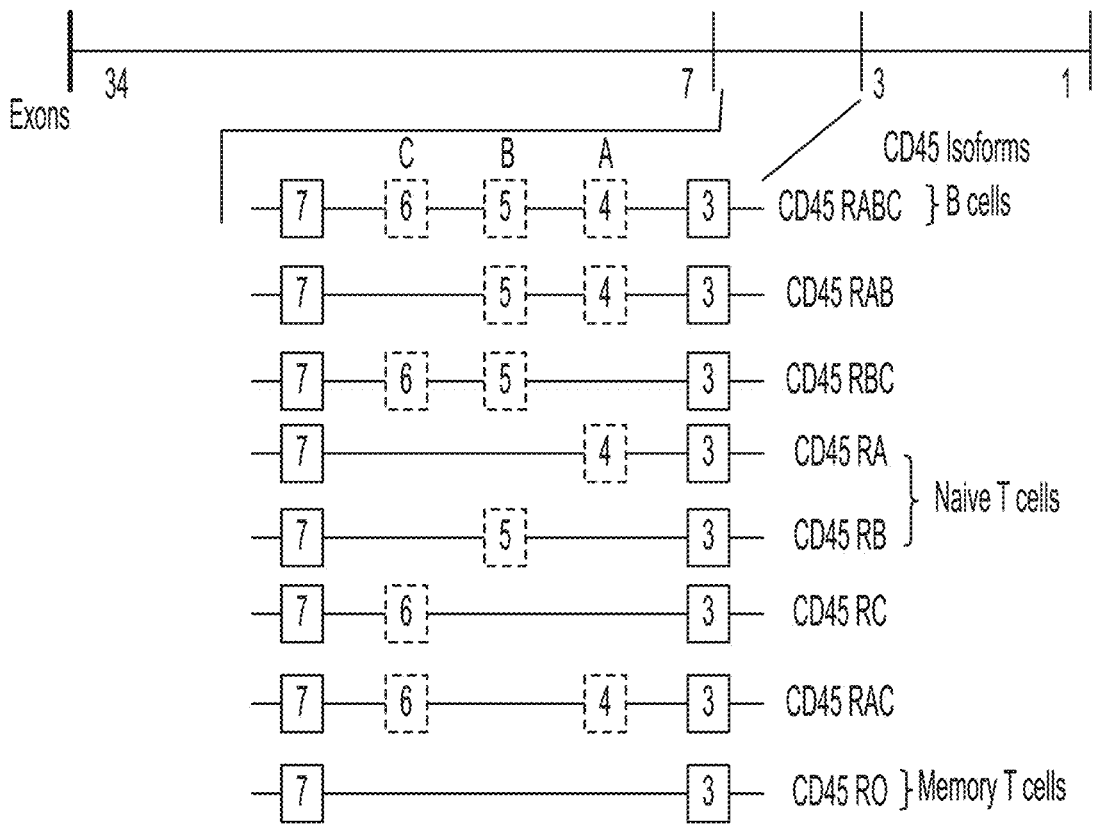
FIG. 1 shows a schematic diagram of exon usage in various isoforms of CD45 produced by differential splicing of the human CD45 gene.
Figure 7:
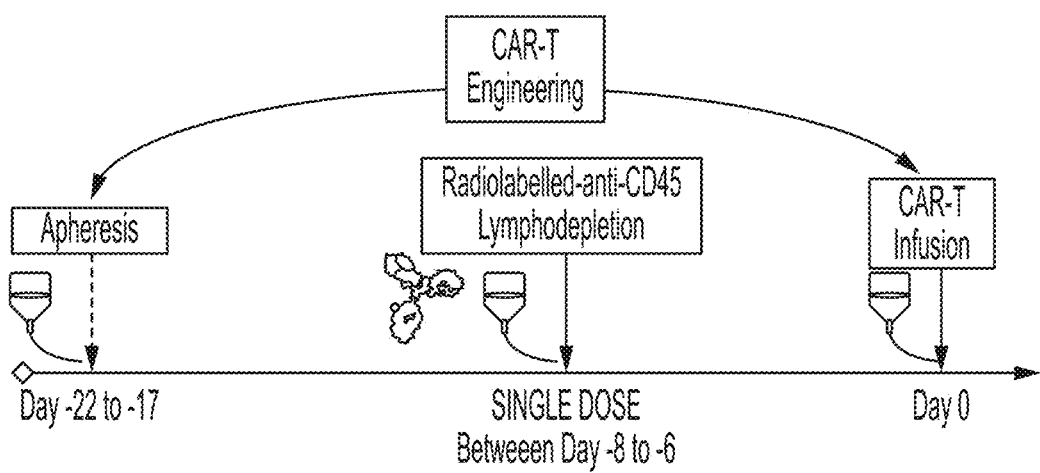

FIG. 7 depicts a method for lymphodepleting a subject prior to performing an adoptive cell therapy according to certain aspects of the present disclosure.

Figure 8:
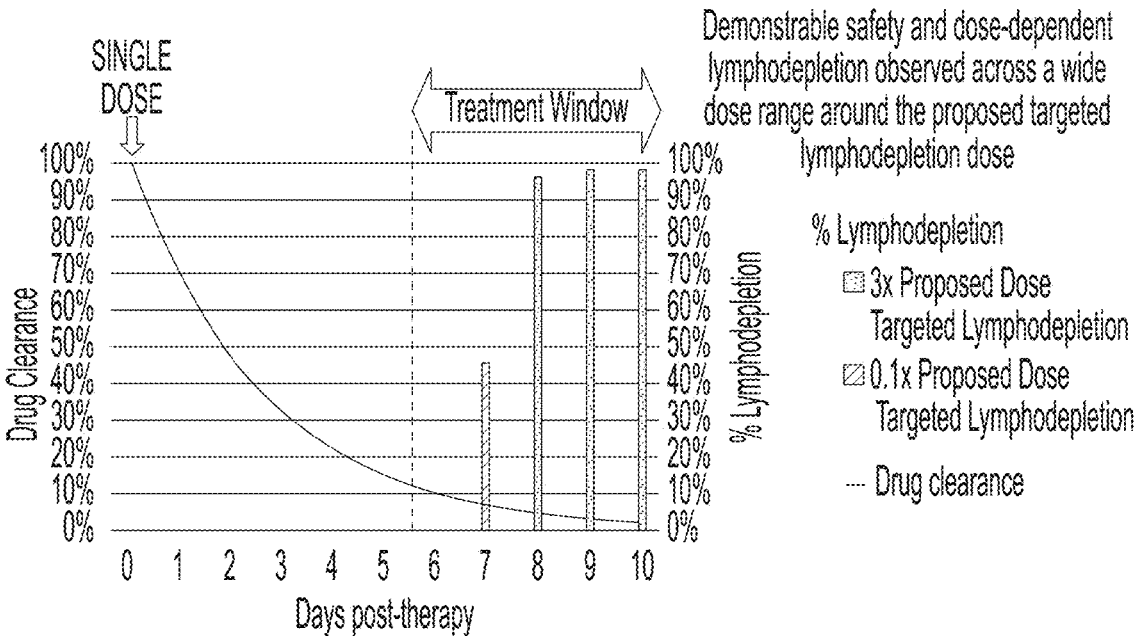

FIG. 8 depicts pharmo-kinetic data demonstrating exemplary clearance and dosing times for a lymphodepletion protocol according to the present disclosure.

Figures 9A, 9B:
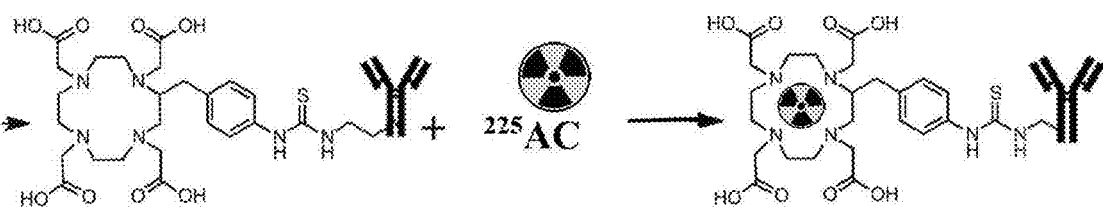

FIGS. 9A and 9B provide schematic diagrams of a method for radiolabeling the anti-CD45 mAb BC8 with actinium ($^{225}$Ac), wherein FIG. 9A illustrates attachment of the bifunctional chelator S-2-(4-Isothiocyanatobenzyl)-1,4,7,10 tetraazacyclo-dodecanetetraacetic acid (p-SCN-Bn-DOTA; referred to as DOTA in the figures) to the monoclonal antibody against CD45, and FIG. 9B illustrates radiolabeling of the DOTA-anti-CD45 conjugate with $^{225}$Ac to provide $^{225}$Ac-DOTA-anti-CD45.

Figure 10A:
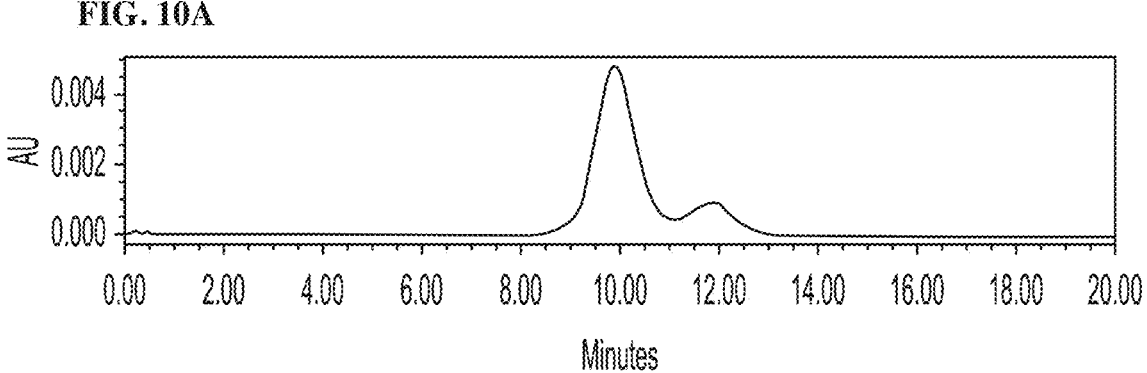
Figure 10B:
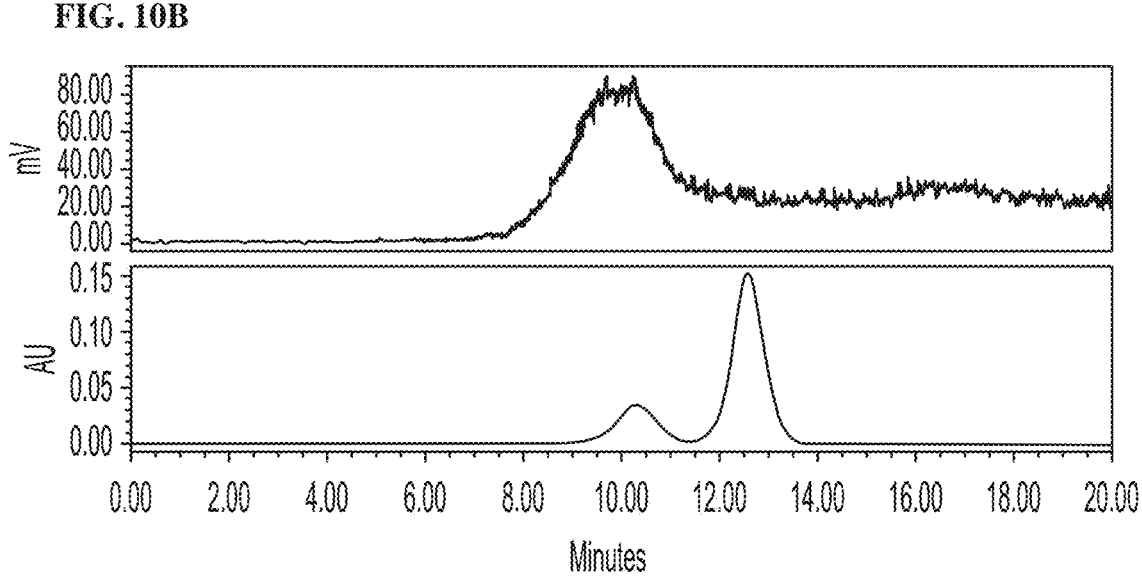

FIGS. 10A and 10B provide elution profiles for a BC8 standard and $^{225}$Ac-DOTA-BC8 from SEC-HPLC (size exclusion chromatography-high performance liquid chromatography), wherein FIG. 10A illustrates elution of the BC8 standard and FIG. 10B illustrates elution of the $^{225}$Ac-DOTA-BC8 (the peak at 13 minutes is the HSA added to stabilize the conjugated antibody).

Figure 11:
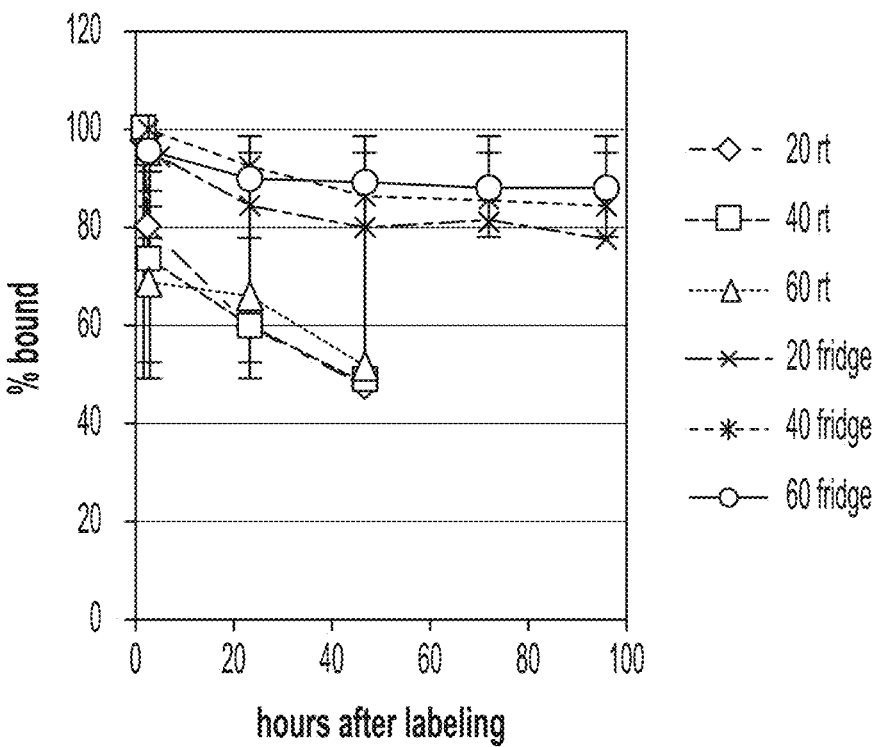

FIG. 11 provides a graph showing the stability of $^{225}$Ac-DOTA-BC8 at various storage dilutions and temperatures as a function of time.

Figure 12:
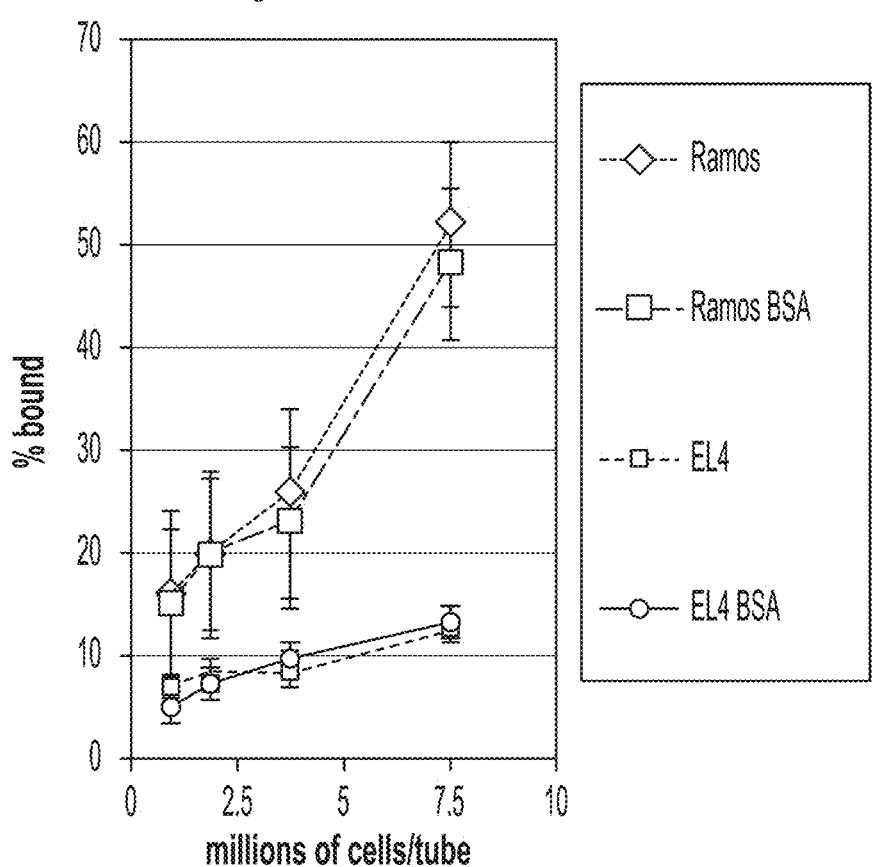

FIG. 12 provides a graph showing the $^{225}$Ac-DOTA-BC8 immunoreactivity against Ramos cells (CD45 positive cells) and EL4 cells (Cd45 negative cells).

Figure 13A:
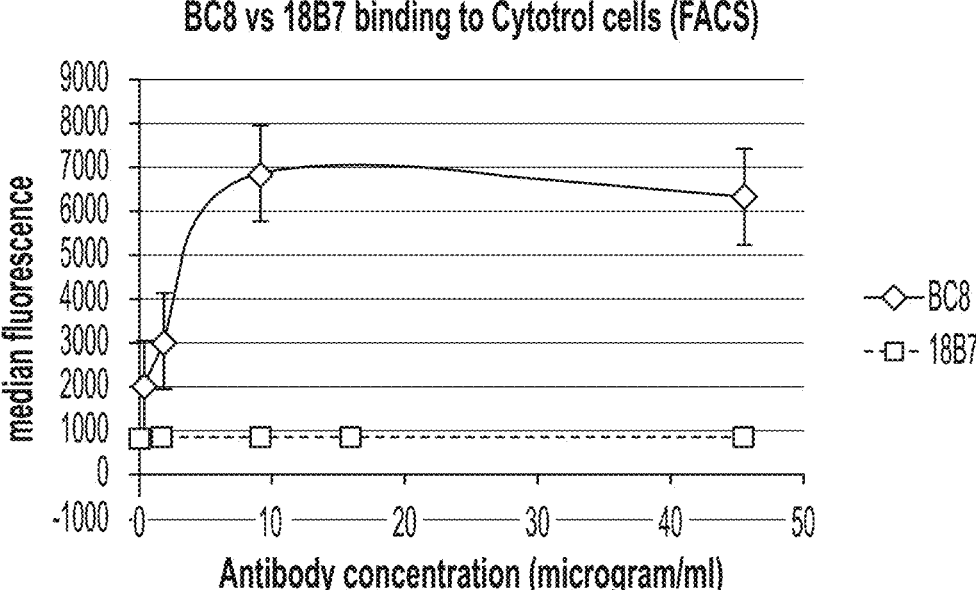
Figure 13B:
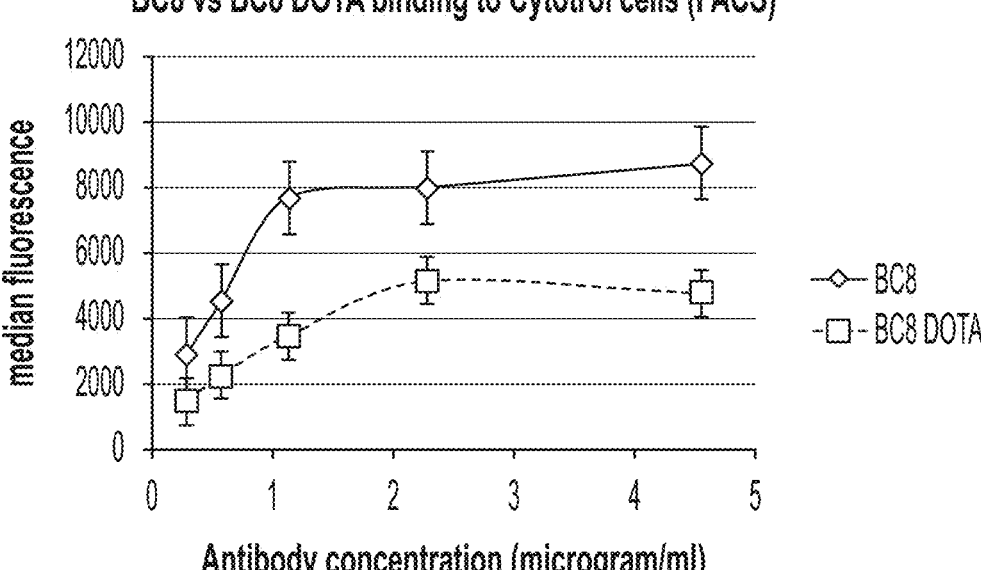

FIGS. 13A and 13B provide graphs showing the binding of various antibody samples to Cytotrol cells measured by flow cytometry, wherein FIG. 13A compares binding of the naïve BC8 and naïve 18B7 (control nonspecific) antibodies to the Cytotrol cells, and FIG. 13B compares binding of naïve BC8 and DOTA-BC8 antibodies to the Cytotrol cells.

7

Figure 14A:
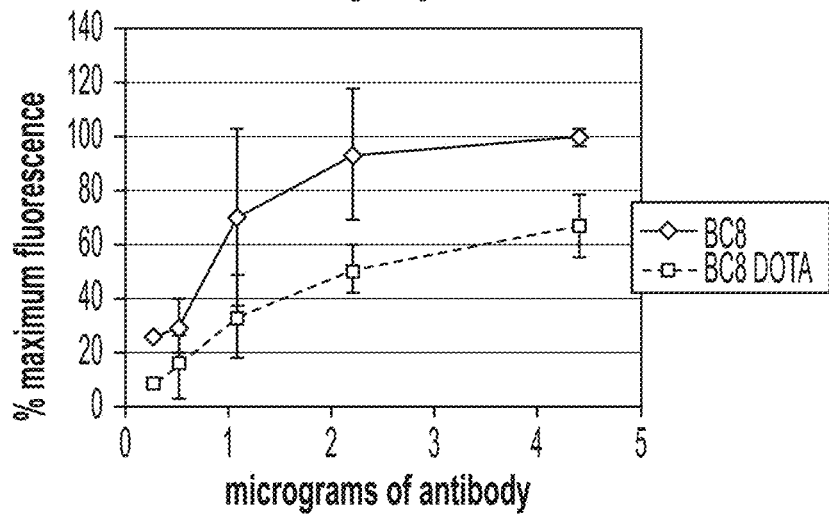

FIG. 14A provides a graph comparing the binding of naïve BC8 and DOTA-BC8 to Cytotrol cells measured by flow cytometry.

Figure 14B:
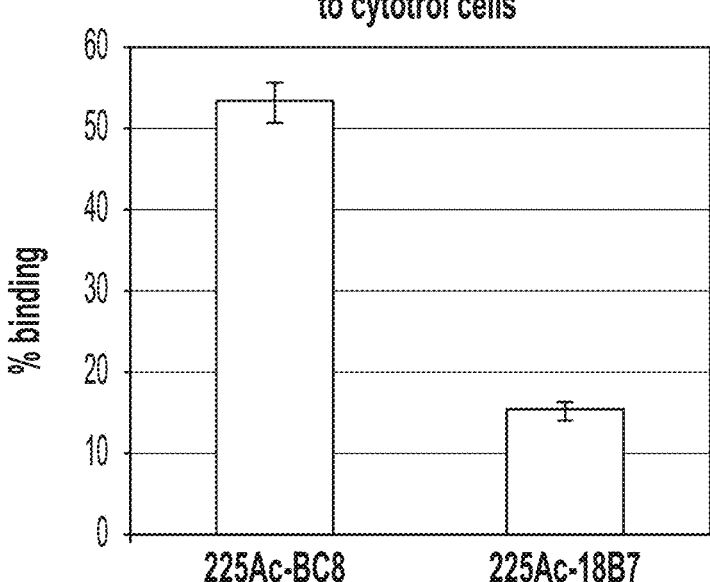

FIG. 14B provides a bar graph showing binding of the DOTA-BC8 sample from FIG. 14A immediately after labeling with $^{225}$Ac (i.e., $^{225}$Ac-DOTA-BC8) compared to the binding of $^{225}$Ac-18B7 (binding to Cytotrol cells) as measured by fraction radiation retained on the cells after washing.

Figure 15A:
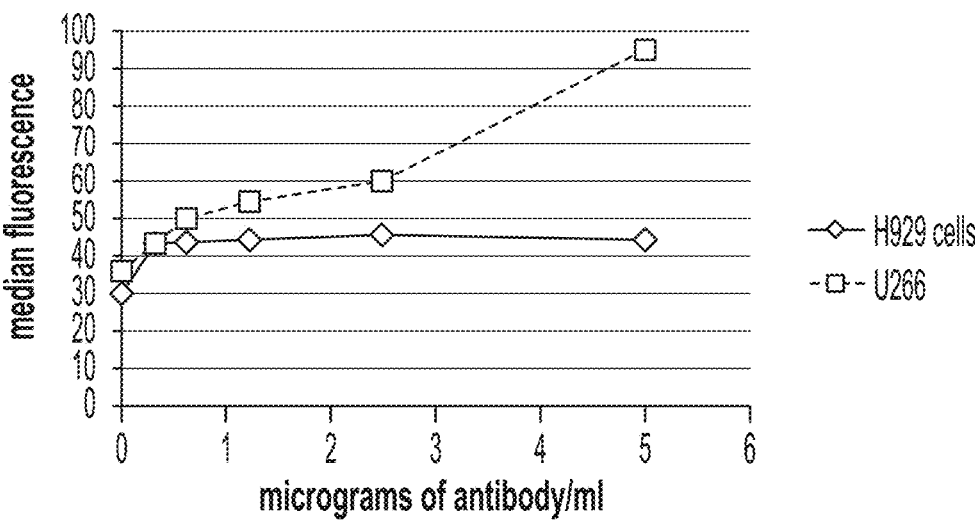
Figure 15B:
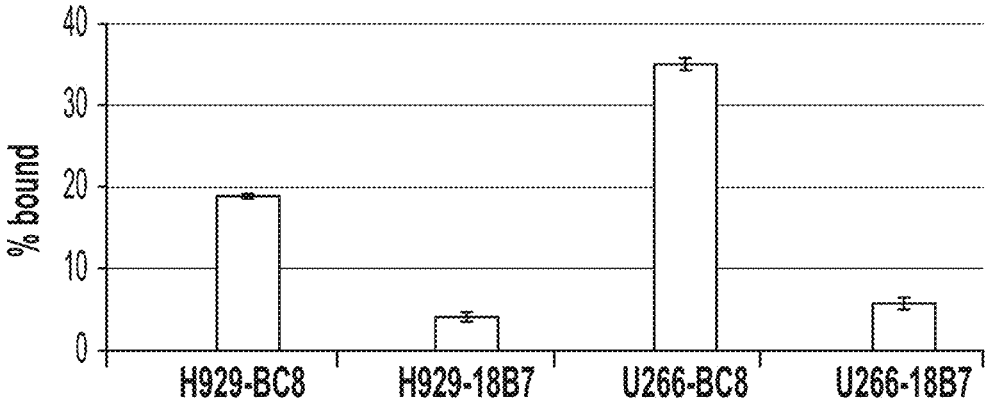

FIGS. 15A and 15B show graphs comparing the binding of DOTA-BC8 to different human multiple myeloma cell lines, i.e., H929 and U266, measure by flow cytometry (FIG. 15A) or after labeling with $^{225}$Ac (i.e., $^{225}$Ac-DOTA-BC8; FIG. 15B) as measured by fraction radiation retained on the cells after washing.

Figure 16A:
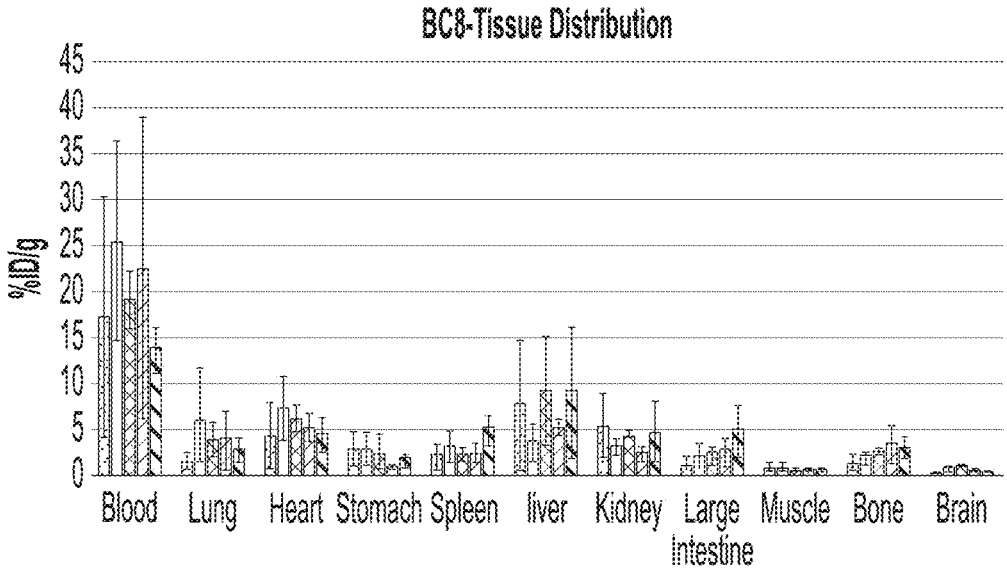
Figure 16B:
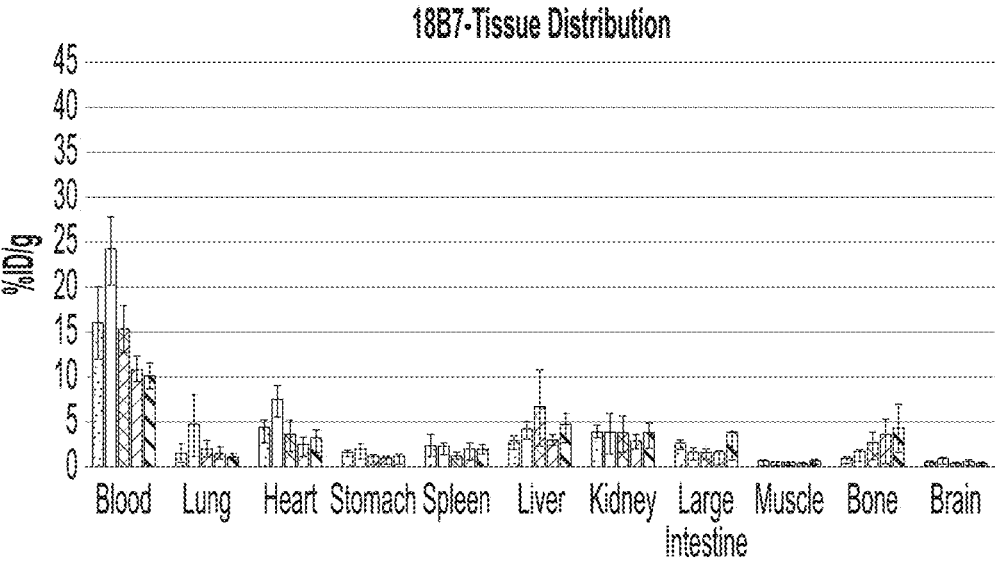

FIGS. 16A and 16B show bar graphs comparing the biodistribution of the $^{225}$Ac-DOTA-BC8 (FIG. 16A) and $^{225}$Ac-DOTA-18B7 (FIG. 16B) antibodies in control mice at 1 hour, 4 hours, 24 hours, 48 hours, and 96 hours.

Figures 17A, 17B:
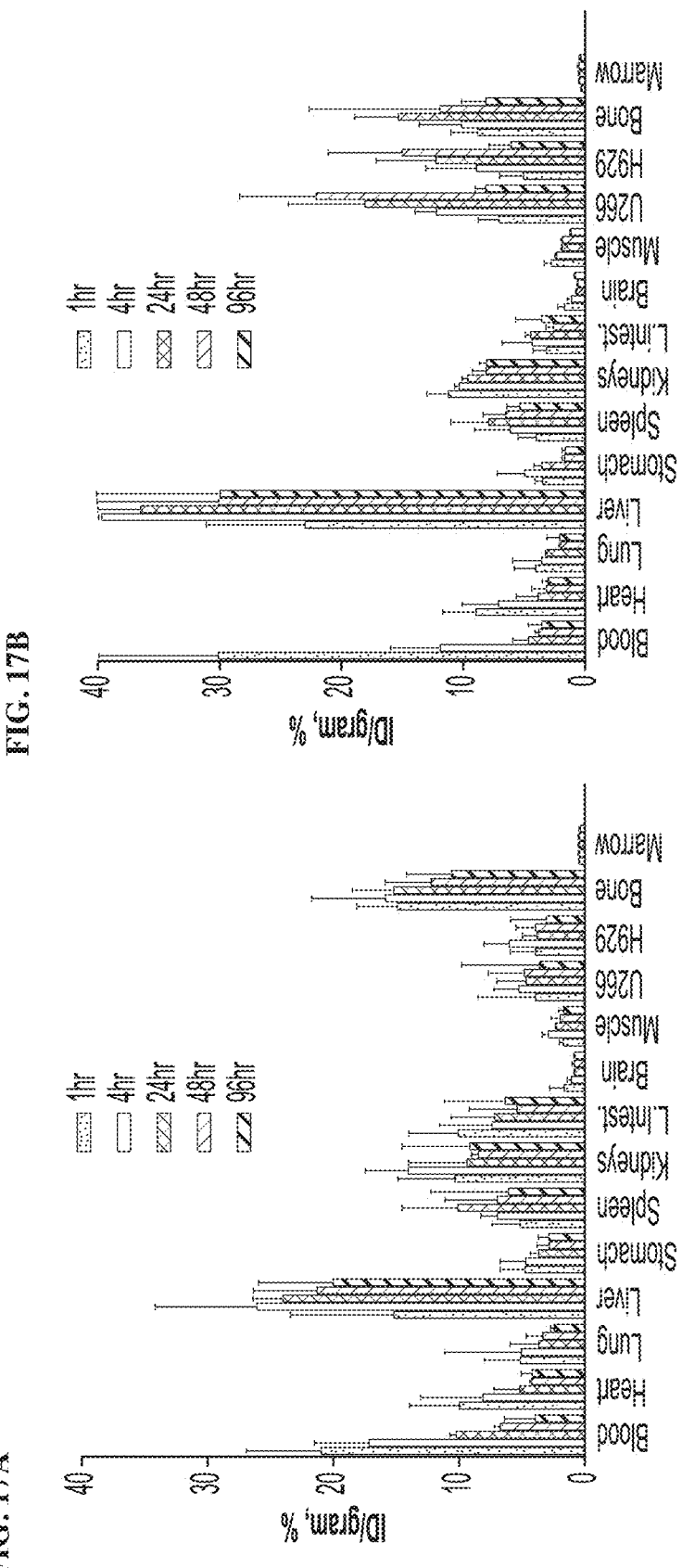

FIGS. 17A and 17B show bar graphs comparing the biodistribution of the $^{225}$Ac-DOTA-18B7 (control; FIG. 17A) and $^{225}$Ac-DOTA-BC8 (FIG. 17B) antibodies in U266 and H929 SCID-NOD tumor bearing mice at 1 hour, 4 hours, 24 hours, 48 hours, and 96 hours.

Figures 18A, 18B:
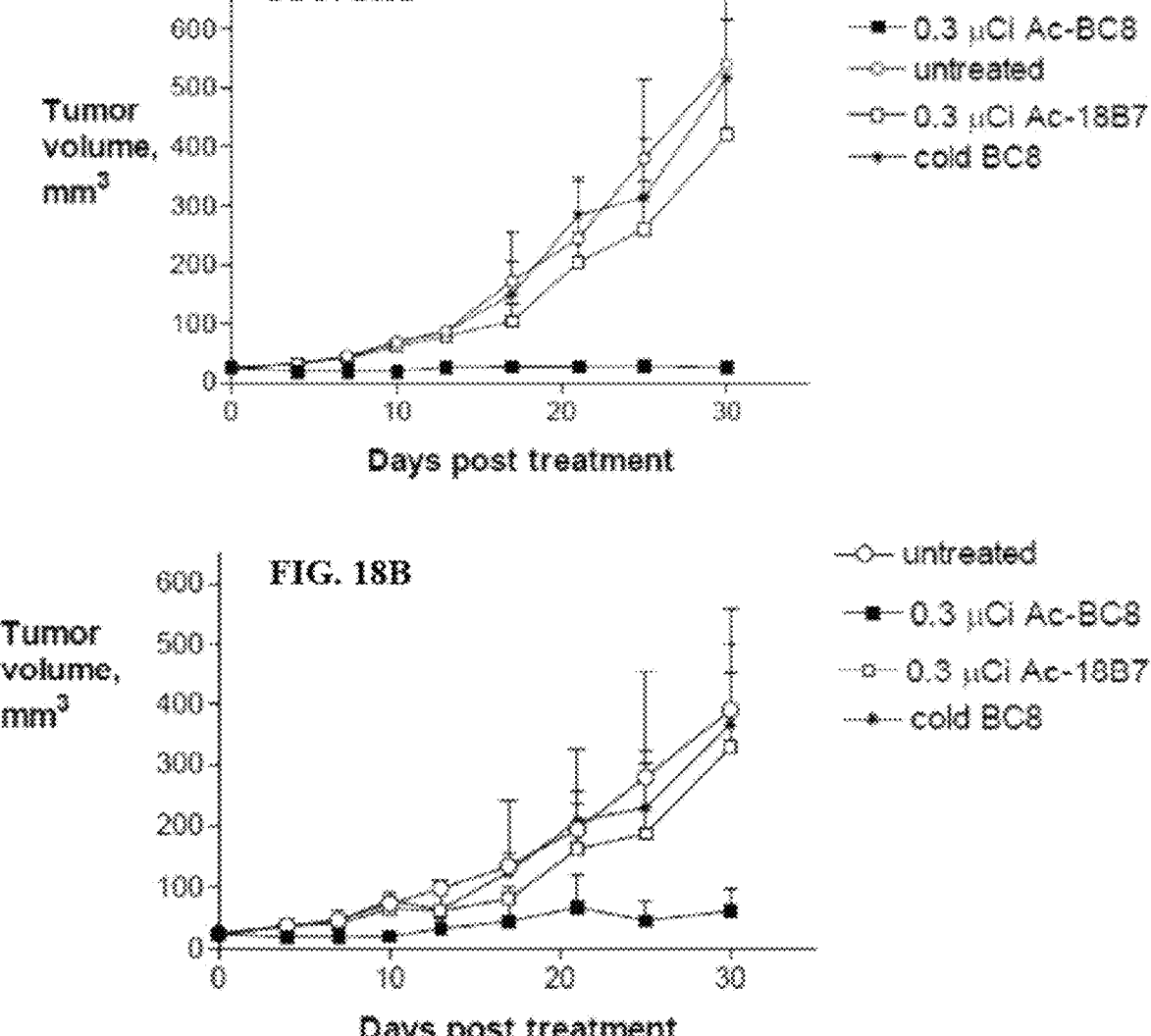

FIG. 18A shows a graph comparing the tumor volume of H929 multiple myeloma xenograph-bearing SCID-NOD mice after radioimmunotherapy treatment with $^{225}$Ac-DOTA-BC8 or $^{225}$Ac-DOTA-18B7 (control).

FIG. 18B shows a graph comparing the tumor volume of U266 multiple myeloma xenograph-bearing SCID-NOD mice after radioimmunotherapy treatment with $^{225}$Ac-DOTA-BC8 or $^{225}$Ac-DOTA-18B7 (control).

Figures 19A, 19B, 19C, 19D:
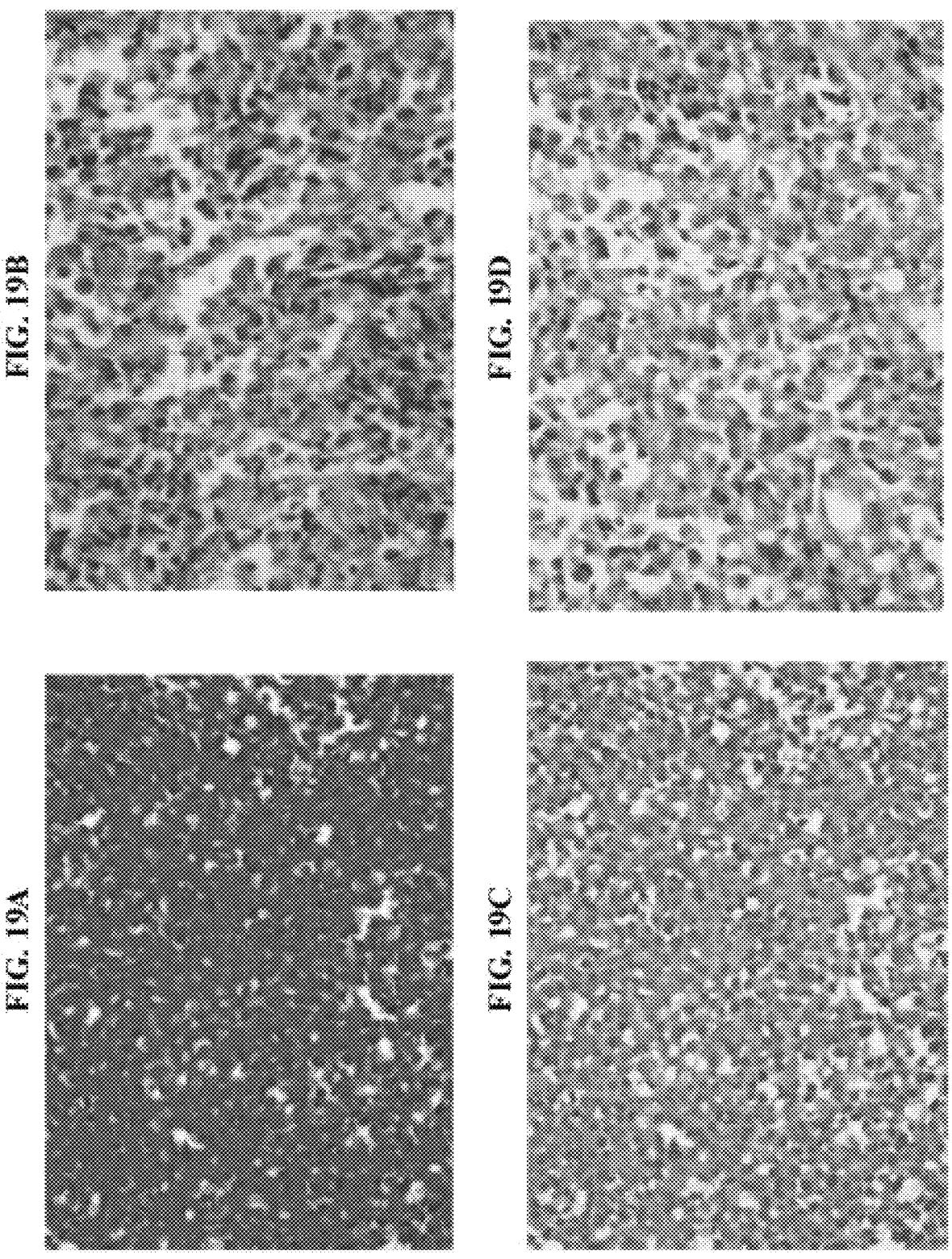

FIGS. 19A-19D show histological analysis of tumors excised from U266 and H929 multiple myeloma xenograph-bearing SCID-NOD mice, wherein FIG. 19A shows an untreated H929 tumor, FIG. 19B shows an $^{225}$Ac-DOTA-BC8 treated H929 tumor, FIG. 19C shows an untreated U266 tumor, and FIG. 19D shows an $^{225}$Ac-DOTA-BC8 treated U266 tumor.

Figure 20:
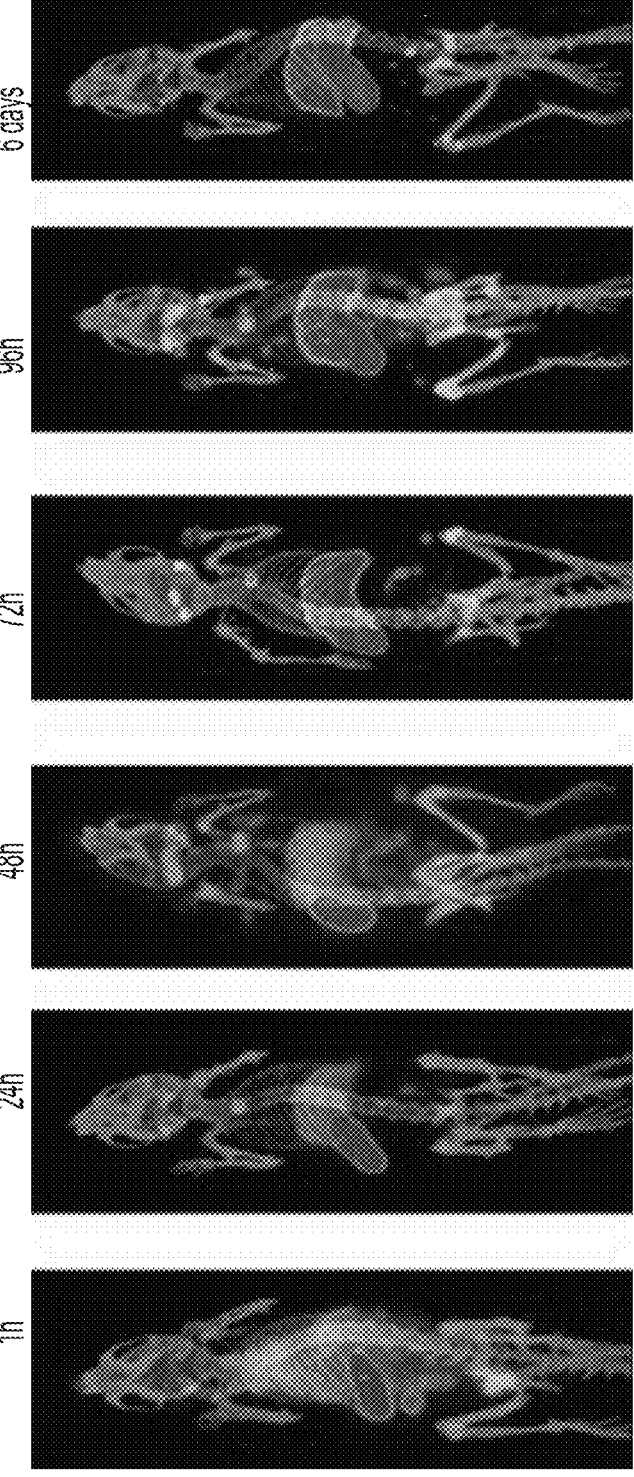

FIG. 20 shows microSPEC/CT scans of C57Bl/6 mice injected (i.p.) with $^{111}$Ln-anti-CD45 taken 1 hour, 24 hours, 48 hours, 72 hours, 96 hours, and 6 days after injection.

Figure 21A:
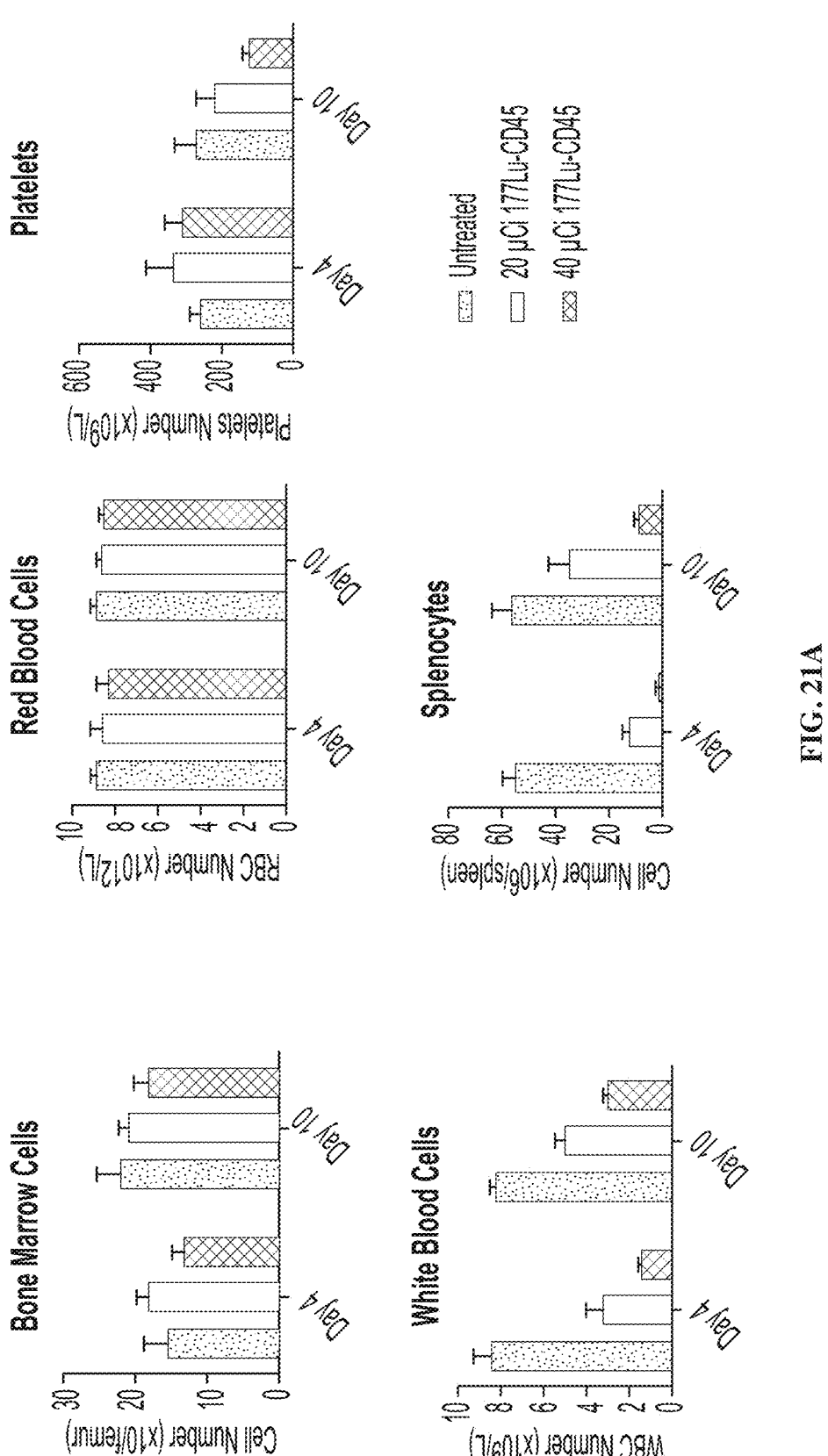
Figure 21B:
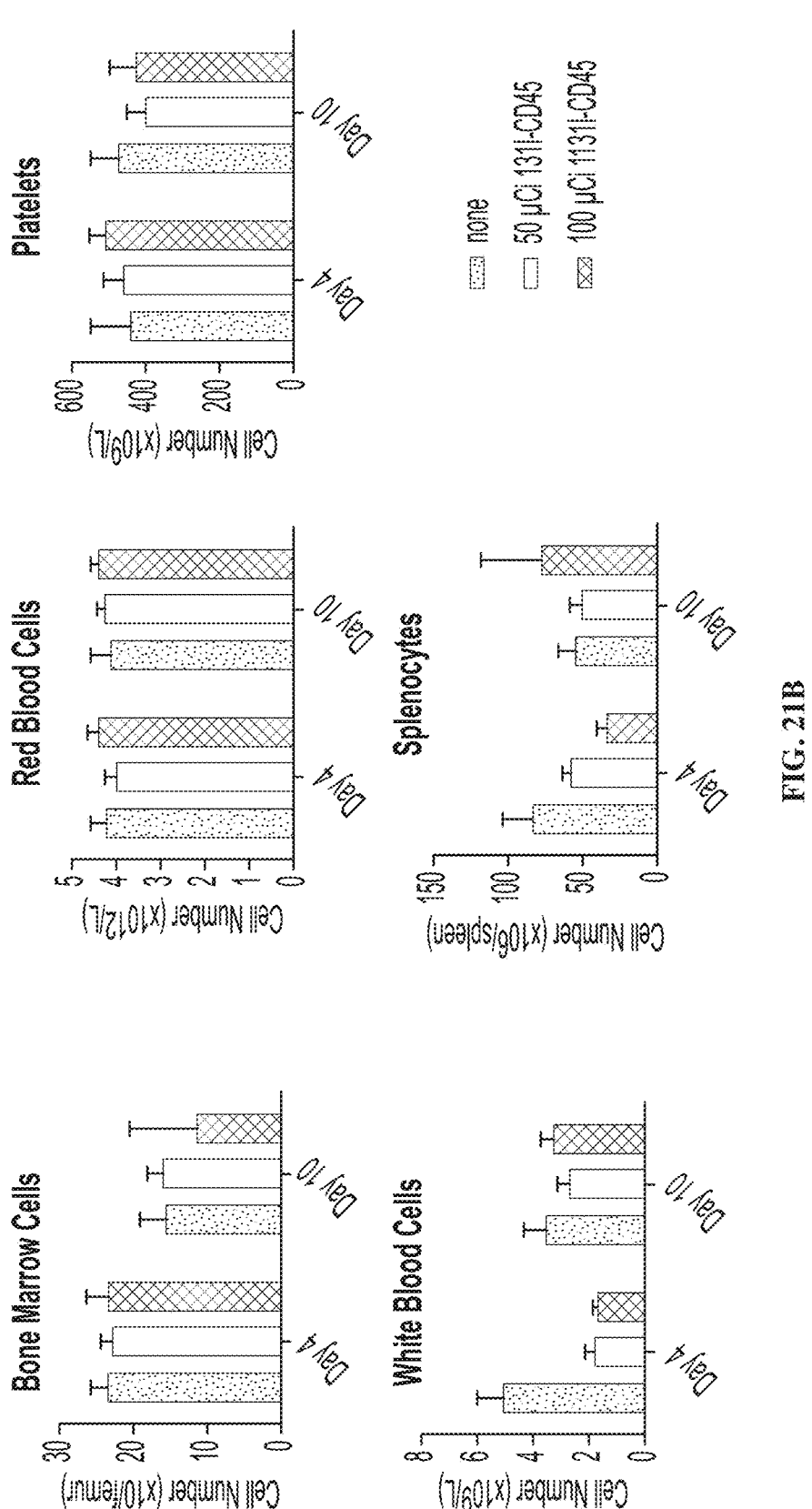

FIG. 21 shows bar graphs of the amounts of depletion of various immune cell subpopulations in non-tumor bearing C57Bl/6 mice after treatment with (A)$^{117}$Lu-anti-CD45 or (B)$^{131}$I-anti-CD45.

Figure 22:
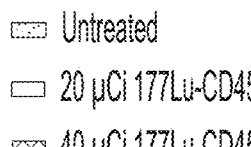

FIG. 22 shows bar graphs of the amounts of depletion of various immune cell populations in the spleens of non-tumor bearing C57Bl/6 mice after treatment with (A)$^{117}$Lu-anti-CD45 or (B)$^{131}$I-anti-CD45.

Figures 23A, 23B:
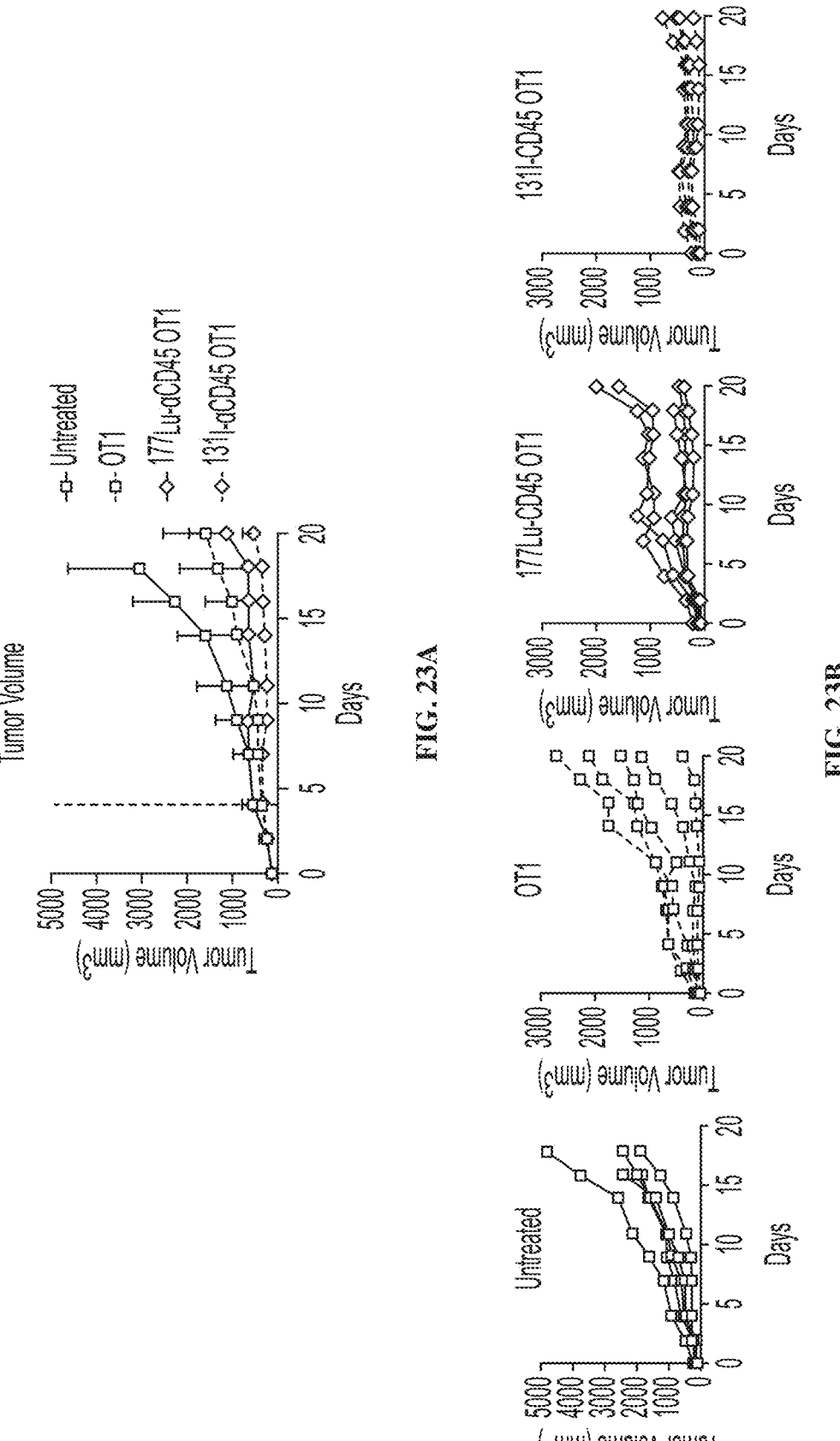
Figure 23C:
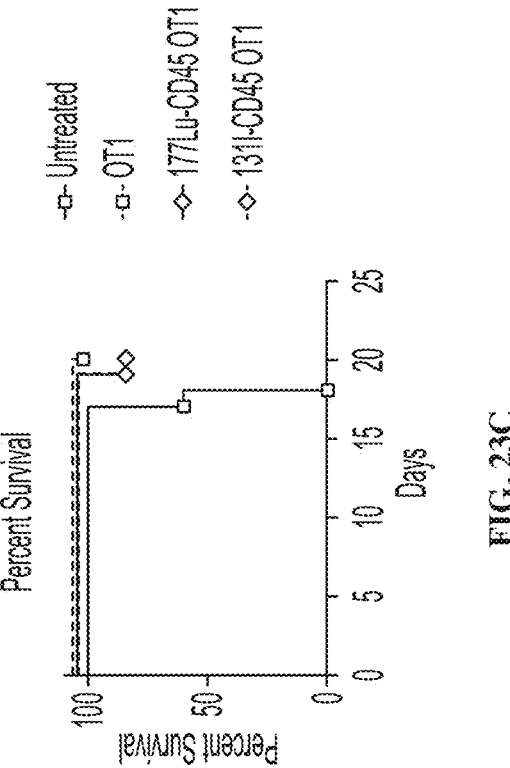

FIG. 23 shows graphs demonstrating that $^{117}$Lu-anti-CD45 and $^{131}$I-anti-CD45 lymphodepletion enable tumor control in an OT I adoptive cell therapy model, wherein (A) demonstrates $^{117}$Lu-anti-CD45 and $^{131}$I-anti-CD45-mediated targeted conditioning prior to adoptively transferred OT I T-cells enabled control of EG.7 tumor growth; (B) shows tumor size for individual mice in each group; and (C) shows survival of control mice that received no conditioning or OT I T-cells, and those conditioned with $^{117}$Lu-anti-CD45 and $^{131}$I-anti-CD45.

BRIEF DESCRIPTION OF THE SEQUENCES

SEQ ID NO:1 is the amino acid sequence of the variable domain of the light chain of anti-CD45 murine immunoglobulin BC8.

SEQ ID NO:2 is the amino acid sequence of the variable domain of the heavy chain of anti-CD45 murine immunoglobulin BC8.

SEQ ID NO:3 is the amino acid sequence of CDR1 of the light chain of anti-CD45 murine immunoglobulin BC8.

SEQ ID NO:4 is the amino acid sequence of CDR2 of the light chain of anti-CD45 murine immunoglobulin BC8.

SEQ ID NO:5 is the amino acid sequence of CDR3 of the light chain of anti-CD45 murine immunoglobulin BC8.

SEQ ID NO:6 is the amino acid sequence of CDR1 of the heavy chain of anti-CD45 murine immunoglobulin BC8.

SEQ ID NO:7 is the amino acid sequence of CDR2 of the heavy chain of anti-CD45 murine immunoglobulin BC8.

SEQ ID NO:8 is the amino acid sequence of CDR3 of the heavy chain of anti-CD45 murine immunoglobulin BC8.

SEQ ID NO:9 is the amino acid sequence of N-terminus of the light chain of anti-CD45 murine immunoglobulin BC8.

SEQ ID NO:10 is the amino acid sequence of N-terminus of the heavy chain of anti-CD45 murine immunoglobulin BC8.

SEQ ID NO:11 is the nucleotide sequence of the light chain of anti-CD45 murine immunoglobulin BC8.

SEQ ID NO:12 is the amino acid sequence of the light chain of anti-CD45 murine immunoglobulin BC8 including a leader sequence.

SEQ ID NO:13 is the amino acid sequence of the light chain of anti-CD45 murine immunoglobulin BC8 starting at the protein N-terminal (i.e., absent the leader sequence).

SEQ ID NO:14 is the nucleotide sequence of the heavy chain of anti-CD45 murine immunoglobulin BC8.

SEQ ID NO:15 is the amino acid sequence of the heavy chain of anti-CD45 murine immunoglobulin BC8 including a leader sequence.

SEQ ID NO:16 is the amino acid sequence of the heavy chain of anti-CD45 murine immunoglobulin BC8 starting at the protein N-terminal (i.e., absent the leader sequence).

SEQ ID NO:17 is the amino acid sequence of the human IgG1 heavy chain constant region.

SEQ ID NO:18 is the amino acid sequence of the human IgG2 heavy chain constant region.

SEQ ID NO:19 is the amino acid sequence of the human IgG4 heavy chain constant region.

SEQ ID NO:20 is the amino acid sequence of the human IgG4 heavy chain constant region comprising the mutation S228P.

SEQ ID NO:21 is the amino acid sequence of the human Kappa light chain constant region.

Definitions and Abbreviations

Throughout this application, various publications are cited. The disclosure of these publications is hereby incorporated by reference into this application to describe more fully the state of the art to which this disclosure pertains.

In this application, certain terms are used which shall have the meanings set forth as follows.

The singular forms "a," "an," "the" and the like include plural referents unless the context clearly dictates otherwise. Thus, for example, reference to "an" antibody includes both a single antibody and a plurality of different antibodies.

The term "about" when used before a numerical designation, e.g., temperature, time, amount, and concentration, including a range, indicates approximations which may vary by ±10%, ±5%, or ±1%.

As used herein, "administer", with respect to an antibody, means to deliver the antibody to a subject's body via any known method suitable for antibody delivery. Specific modes of administration include, without limitation, intravenous, transdermal, subcutaneous, intraperitoneal and intrathecal administration. Exemplary administration methods for antibodies may be as substantially described in International Publication No. WO 2016/187514, incorporated in its entirety herein by reference herein.

In addition, according to aspects of the present disclosure, antibodies can be formulated using one or more routinely used pharmaceutically acceptable carriers. Such carriers are well known to those skilled in the art. For example, injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's).

As used herein, the term "antibody" includes, without limitation, (a) an immunoglobulin molecule comprising two heavy chains and two light chains, which recognizes an antigen; (b) polyclonal and monoclonal immunoglobulin molecules; (c) monovalent and divalent fragments thereof (e.g., di-Fab); and (d) bi-specific forms thereof. Immunoglobulin molecules may derive from any of the commonly known classes, including but not limited to IgA, secretory IgA, IgG and IgM. IgG subclasses are also well known to those in the art and include, but are not limited to, human IgG1, IgG2, IgG3 and IgG4. Antibodies can be both naturally occurring and non-naturally occurring (e.g., IgG-Fc-silent). Furthermore, antibodies include chimeric antibodies, wholly synthetic antibodies, single chain antibodies, and fragments thereof. Antibodies may be human, humanized or nonhuman.

A "humanized" antibody refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

As used herein, "non-cancerous disorders" or "non-malignant disorders" include, without limitation, hemoglobinopathies (e.g., SCD), congenital immunodeficiencies (e.g., SCID), autoimmune disorders (e.g., multiple sclerosis, rheumatoid arthritis, scleroderma, systemic lupus, Type 1 diabetes, myathenia gravis, sjogen's disease, polymyositis, etc.), and viral infections (e.g., an HIV infection). Non-cancerous disorders exclude, for example, solid cancers (e.g., tumors) and hematologic malignancies.

As used herein, "cancer" or "malignant disorder" includes, without limitation, a solid cancer (e.g., a tumor) and a hematologic malignancy. A "hematologic malignancy", also known as a blood cancer, is a cancer that originates in blood-forming tissue, such as the bone marrow or other cells of the immune system. Hematologic malignancies include, without limitation, leukemias (such as acute myeloid leukemia (AML), acute promyelocytic leukemia, acute lymphoblastic leukemia (ALL), acute mixed lineage leukemia, chronic myeloid leukemia, chronic lymphocytic leukemia (CLL), hairy cell leukemia and large granular lymphocytic leukemia), myelodysplastic syndrome (MDS), myeloproliferative disorders (polycythemia vera, essential thrombocytosis, primary myelofibrosis and chronic myeloid leukemia), lymphomas, multiple myeloma, MGUS and similar disorders, Hodgkin's lymphoma, non-Hodgkin lymphoma (NHL), primary mediastinal large B-cell lymphoma, diffuse large B-cell lymphoma, follicular lymphoma, transformed follicular lymphoma, splenic marginal zone lymphoma, lymphocytic lymphoma, T-cell lymphoma, and other B-cell malignancies.

"Solid cancers" include, without limitation, bone cancer, pancreatic cancer, skin cancer, cancer of the head or neck, cutaneous or intraocular malignant melanoma, uterine cancer, ovarian cancer, prostate cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, pediatric tumors, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally-induced cancers including those induced by asbestos.

As used herein, the term "burden", when used in connection with a cancerous cell, means quantity. So, a cancerous cell "burden" means the quantity of cancerous cells. Cancerous cells have a burden with respect to their tissue of origin (i.e., the primary site of disease), such as the "bone marrow blast burden" in the case of AML. Cancerous cells also have a burden with respect to one or more tissues other than those of origin, such as the blast burden in blood, liver and spleen in the case of AML. The term "peripheral burden" relates to such cells. The peripheral burden of cancerous cells, such as blasts in the case of AML, can be measured in different ways with different outcomes. For example, in the case of AML, the "peripheral blast burden" can be measured as the total blast population outside of the bone marrow, or the total blast population of the blood, spleen and liver combined, or simply the blast population of the blood as measured in cells per unit volume. As used herein in connection with AML and other cancers originating in the bone marrow, and unless stated otherwise, the term "peripheral cancerous cell burden" (e.g., peripheral blast burden) refers to the cancerous cell population of the blood as measured in cells per unit volume (e.g., cells/µl). This blood-based measurement is a useful proxy for the more cumbersome measurements of spleen and liver burdens, for example.

Herein, a peripheral cancerous cell burden in a subject is "high" if, when the subject is administered an agent, e.g., a radiolabeled anti-CD45 antibody of the present disclosure, that targets a hematologic malignancy-associated antigen at the maximum safe dose, the agent does not reach the primary site of disease in a sufficient amount to bind to more than 90% of its target antigens at that site. Conversely, a peripheral cancerous cell burden in a subject is "low" if, when the subject is administered the agent at the maximum safe dose, the agent reaches the primary site of disease in a sufficient amount to bind to more than 90% of its target antigens at that site. In the case of AML, examples of low peripheral blast burden are those yielding blood blast burdens at or below 1,000 blast cells/µl, at or below 500 blast cells/µl, at or below 400 blast cells/µl, at or below 300 blast cells/µl, at or below 200 blast cells/µl, at or below 100 blast cells/µl, and at or below 50 blast cells/µl.

As used herein, a "low dose" of radiolabeled anti-CD45 antibody of the present disclosure is one that is sub-saturating, and as such introduces into the subject's body fewer target antigen-binding sites (i.e., CD45-binding sites on the administered antibody) than there are target antigens (i.e., CD45 molecules). According to certain aspects, a low dose of the radiolabeled anti-CD45 antibody is one where the ratio of CD45-binding sites to CD45 molecules is less than or equal to 9:10, such as less than or equal to 1:2, or less than or equal to 1:5, or less than or equal to 1:10, or less than or equal to 1:20, or less than or equal to 1:100.

As used herein, the term "subject" or "patient" are interchangeable and include, without limitation, a mammal such as a human, a non-human primate, a dog, a cat, a horse, a sheep, a goat, a cow, a rabbit, a pig, a rat and a mouse. Where the subject is human, the subject can be of any age. According to certain aspects, the subject is an infant. According to further aspects, the subject is one, two, three, four, five, six, seven, eight, nine or 10. According to yet further aspects, the subject is from 10 to 15, or from 15 to 20. According to yet further aspects, the subject is 20 or older, 25 or older, 30 or older, 35 or older, 40 or older, 45 or older, 50 or older, 55 or older, 60 or older, 65 or older, 70 or older, 75 or older, 80 or older, 85 or older, or 90 or older.

As used herein, "treating" a subject afflicted with a disorder shall include, without limitation, (i) slowing, stopping or reversing the disorder's progression, (ii) slowing, stopping or reversing the progression of the disorder's symptoms, (iii) reducing, and ideally eliminating, the likelihood of the disorder's recurrence, and/or (iv) reducing, and ideally eliminating, the likelihood that the disorder's symptoms will recur. According to certain preferred aspects, treating a subject afflicted with a disorder means (i) reversing the disorder's progression, ideally to the point of eliminating the disorder, and/or (ii) reversing the progression of the disorder's symptoms, ideally to the point of eliminating the symptoms, and/or (iii) reducing or eliminating the likelihood of relapse. Ideally, treating a subject afflicted with a disorder means curing the disorder by removing or otherwise disabling its genetic cause.

As used herein, "depleting" with respect to a specific cell type of the subject means reducing that cell population within the subject by at least 10%, 20%, 30%, 40%, 50%, 60%, 70%, 80%, 90%, or 95%. As used herein, "ablating" with respect to a specific cell type of the subject means reducing that cell population within the subject by greater than 95%, such as by at least 96%, or 97%, or 98%, or 99%, or even 100%.

The specific cell types depleted using the compositions and methods of the present disclosure include at least hematopoietic stem cells (i.e., multipotential hematopoietic stem cells, also referred to as hemocytoblasts), and lymphocytes, such as peripheral blood lymphocytes or bone marrow lymphocytes. Hematopoietic stem cells ("HSCs") are multipotent, self-renewing progenitor cells from which all differentiated blood cell types arise during the process of hematopoiesis. HSCs are thought to differentiate into two lineage-restricted, lymphoid and myelo-erythroid, oligopotent progenitor cells, although an alternative "myeloid-based" model for blood lineage development describes a novel intermediary myelo-lymphoid progenitor cell, which has the capacity to generate progeny from both lineages.

As used herein, the term "hematopoietic stem cells" ("HSCs") refers to immature blood cells having the capacity to self-renew and to differentiate into mature blood cells containing diverse lineages including but not limited to granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). Such cells may include CD34+ cells. CD34+ cells are immature cells that express the CD34 cell surface marker.

Methods for measuring HSC populations are routine. They include, for example, the use of flow cytometry to detect human HSCs in a bone marrow sample and staining for various cell surface markers (such as Lin, CD34, CD38, CD43, CD45RO, CD45RA, CD59, CD90, CD109, CD117, CD133, CD166, and HLA DR). Reduction of a patient's immune cells may also be detected in peripheral blood. Methods for measuring peripheral blood lymphocyte populations are routine. They include, for example, flow cytometry on whole blood samples to determine lymphocyte counts based on labeling with a fluorescent antibody directed against a specific a cell surface marker such as CD45, CD3, CD4 or CD8. Methods for measuring peripheral blood neutrophil populations are also routine. They include, for example, flow cytometry on whole blood samples to determine neutrophil counts based on labeling with a fluorescent antibody directed against a specific a cell surface marker such as Ly6G.

According to certain aspects of the disclosure, a subject's lymphocyte decrease is determined by measuring the subject's peripheral blood lymphocyte level. As used herein, a subject's "peripheral blood lymphocytes" shall mean the mature lymphocytes circulating in the subject's blood. Examples of peripheral blood lymphocytes include, without limitation, peripheral blood T-cells, peripheral blood NK cells and peripheral blood B cells. As such, and by way of example, a subject's lymphocyte population is depleted if the population of at least one type of the subject's peripheral blood lymphocytes is lowered by no more than 95%. For example, a subject's lymphocytes are depleted if the subject's peripheral blood T-cell level is lowered by 50%, the subject's peripheral blood NK cell level is lowered by 40%, and/or the subject's peripheral blood B cell level is lowered by 30%. In this example, the subject's lymphocytes are depleted even if the level of another immune cell type, such as neutrophils, is not lowered. According to certain aspects, depleting a subject's lymphocytes is reflected by a peripheral blood lymphocyte population reduction of at least 10%, 20%, 30%, 40%, 50%, 60%, 70%, 80%, 90% or 95%.

As used herein, patients that are "in need of" a hematopoietic stem cell transplant include patients that exhibit a defect or deficiency in one or more blood cell types, as well as patients having a stem cell disorder, autoimmune disease, cancer, or other pathology described herein. Hematopoietic stem cells generally exhibit 1) multi-potency, and can thus differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells), 2) self-renewal, and can thus give rise to daughter cells that have equivalent potential as the mother cell, and 3) the ability to be reintroduced into a transplant recipient whereupon they home to the hematopoietic stem cell niche and re-establish productive and sustained hematopoiesis.

Additionally or alternatively, a patient "in need of" a hematopoietic stem cell transplant may one that is or is not suffering from a pathology, but nonetheless exhibits a reduced level (e.g., as compared to that of an otherwise healthy subject) of one or more endogenous cell types within the hematopoietic lineage, such as megakaryocytes, thrombocytes, platelets, erythrocytes, mast cells, myeoblasts, basophils, neutrophils, eosinophils, microglia, granulocytes, monocytes, osteoclasts, antigen-presenting cells, macrophages, dendritic cells, natural killer cells, T-lymphocytes, and B-lymphocytes.

The Anti-CD45 Antibody

As used herein, an "anti-CD45 antibody" or "anti-CD45-immunoglobulin" is an antibody that binds to an epitope of CD45. According to certain aspects, the anti-CD45 antibody may bind to the epitope recognized by the monoclonal antibody "BC8." BC8 is known, as are methods of making it. These methods are described, for example, in International Publication No. WO 2017/155937, incorporated by reference herein in its entirety, and in the examples provided herein.

The BC8 monoclonal antibody may comprise a light chain having the amino acid sequence set forth in SEQ ID NO:12, which includes the leader sequence (FIG. 4A), or SEQ ID NO:13, which excludes the leader sequence (FIG. 4B). The BC8 monoclonal antibody may comprise a light chain variable region having the amino acid sequence set forth in SEQ ID NO:1 (FIG. 2). The BC8 monoclonal antibody may comprise a light chain having the N-terminal amino acid sequence set forth in SEQ ID NO:9 (FIG. 3). According to certain aspects, the light chain comprises at least one complementarity determining region having the amino acid sequence as set forth in SEQ ID NO:3, SEQ ID NO:4, or SEQ ID NO:5 (FIG. 3). According to certain aspects, the light chain comprises the N-terminal amino acid sequence set forth in SEQ ID NO:9 and at least one complementarity determining region having the amino acid sequence as set forth in SEQ ID NO:3, SEQ ID NO:4, or SEQ ID NO:5 (FIG. 3).

The BC8 monoclonal antibody may comprise a heavy chain having the amino acid sequence set forth in SEQ ID NO:15, which includes the leader sequence (FIG. 5A), or SEQ ID NO:16, which excludes the leader sequence (FIG. 5B). The BC8 monoclonal antibody may comprise a heavy chain variable region having the amino acid sequence set forth in SEQ ID NO:2 (FIG. 2). The BC8 monoclonal antibody may comprise a heavy chain having the N-terminal amino acid sequence set forth in SEQ ID NO:10 (FIG. 3). According to certain aspects, the heavy chain comprises at least one complementarity determining region having the amino acid sequence as set forth in SEQ ID NO:6, SEQ ID NO:7, or SEQ ID NO:8 (FIG. 3). According to certain aspects, the heavy chain comprises a heavy chain having the N-terminal amino acid sequence set forth in SEQ ID NO: 10 and at least one complementarity determining region having the amino acid sequence as set forth in SEQ ID NO:6, SEQ ID NO:7, or SEQ ID NO:8 (FIG. 3).

According to certain aspects, the BC8 monoclonal antibody comprises a heavy chain having the amino acid sequence set forth in SEQ ID NO:15 or 16, wherein the amino acid at position 141 (relative to the N-terminal amino acid) is either an ASP or an ASN. A ratio of ASP:ASN at position 141 in a population of BC8 proteins may be within the range 1:99 to 99:1, such as 10:90 to 90:10.

According to certain aspects, the BC8 monoclonal antibody comprises a heavy chain variable region having the amino acid sequence set forth in SEQ ID NO:2, wherein the amino acid at position 141 in the constant region (relative to the N-terminal amino acid) is either an ASP or an ASN. A ratio of ASP:ASN at position 141 in a population of BC8 proteins may be within the range 1:99 to 99:1, such as 10:90 to 90:10.

According to certain aspects, the antibody against CD45 (anti-CD45 antibody) may be a chimeric or humanized antibody. For example, the BC8 monoclonal antibody may comprise a humanized or chimeric BC8 antibody (referred to as "BC8c" herein). For example, a humanized BC8c monoclonal antibody may comprise the parent murine variable (V) regions grafted on to human IgG1, IgG2, or IgG4 constant regions for the heavy chain or a human kappa region for the light chain. IgG4 antibodies are capable of exchanging Fab arms by swapping a heavy chain and attached light chain (half molecule) with a heavy-light chain pair from another molecule, resulting in bispecific antibodies. This process, termed "Fab-arm exchange" herein, has been shown to occur under reducing conditions in vitro and in vivo in mice. The ability of IgG4 antibodies to undergo Fab-arm exchange has been accredited to the instable core-hinge sequence in combination with sequence determinants in the IgG4 CH3 domain. Replacement of core-hinge residue Ser228 by Pro (S228P) results in a partial stabilization of an IgG4 molecule in vitro and in vivo. As such, according to certain aspects, the IgG4 can comprise either S or P at position 228, wherein the mutation S228P may help stabilize the Ab and prevent Fab arm exchange.

Such chimerism, i.e., humanizing BC8 to produce BC8c, may be achieved by methods known in the art, such as by cloning DNA encoding the BC8 murine heavy and light chain V regions and endogenous murine signal sequences in frame into mammalian expression vectors for the heavy and light chains that already contain human heavy chain constant regions (IgG1, IgG2, or IgG4) or human C kappa.

Thus, according to certain aspects, the BC8 monoclonal antibody may be chimeric BC8, i.e., BC8c, and may comprise a human IgG1 heavy chain constant region having the amino acid sequence as set forth in SEQ ID NO:17, or a human IgG2 heavy chain constant region having the amino acid sequence as set forth in SEQ ID NO: 18, or a human IgG4 heavy chain constant region having the amino acid sequence as set forth in SEQ ID NO: 19, or a human IgG4 heavy chain constant region having the amino acid sequence as set forth in SEQ ID NO:20, or a human kappa light chain constant region having the amino acid sequence as set forth in SEQ ID NO:21 (FIG. 6A-6E).

According to certain aspects, the BC8 monoclonal antibody may be chimeric (BC8c) comprising a human IgG1, IgG2, or IgG4 heavy chain constant region having the amino acid sequence as set forth in any one of SEQ ID NOS:17-20, and a human kappa light chain constant region having the amino acid sequence as set forth in SEQ ID NO:21 (FIG. 6A-6E).

According to certain aspects, the chimeric BC8c monoclonal antibody may comprise a light chain variable region having the amino acid sequence set forth in SEQ ID NO:1 (FIG. 2). The BC8c monoclonal antibody may comprise a light chain having the N-terminal amino acid sequence set forth in SEQ ID NO:9 (FIG. 3). The BC8c monoclonal antibody may comprise a light chain having at least one complementarity determining region having the amino acid sequence as set forth in SEQ ID NO:3, SEQ ID NO:4, or SEQ ID NO:5 (FIG. 3).

According to certain aspects, the chimeric BC8c monoclonal antibody may comprise a heavy chain variable region having the amino acid sequence set forth in SEQ ID NO:2 (FIG. 2). The BC8c monoclonal antibody may comprise a heavy chain having the N-terminal amino acid sequence set forth in SEQ ID NO:10 (FIG. 3). The BC8c monoclonal antibody may comprise a heavy chain having at least one complementarity determining region having the amino acid sequence as set forth in SEQ ID NO:6, SEQ ID NO:7, or SEQ ID NO:8 (FIG. 3).

According to certain aspects, the heavy chain of the BC8 or BC8c monoclonal antibody comprises a C-terminal lysine, a C-terminal glycine (G) having lost the C-terminal lysine (K), or is lacking both GK. When referring to antibodies comprising a modified heavy chain constant region described herein, the antibody may comprise a provided sequence having the C-terminal GK or K, or alternatively, lacking GK or K.

Patient Specific Composition

As used herein, a composition comprising $^{225}$Ac-labelled BC8 includes both actinium-225 labeled antibody and non-labeled antibody, with the minority being the actinium-225 labeled antibody. Likewise, for $^{177}$Lu-labelled BC8, the composition will include both labelled and unlabeled antibody populations. The ratio of labeled to non-labeled antibody can be adjusted using known methods. Thus, accordingly to certain aspects of the present disclosure, the anti-CD45 antibody may be provided in a total protein amount of up to 100 mg, such as up to 60 mg, such as 5 mg to 45 mg, or a total protein amount of from 0.001 mg/kg patient weight to 3.0 mg/kg patient weight, such as from 0.005 mg/kg patient weight to 2.0 mg/kg patient weight, or from 0.01 mg/kg patient weight to 1 mg/kg patient weight, or from 0.1 mg/kg patient weight to 0.6 mg/kg patient weight, or 0.3 mg/kg patient weight, or 0.4 mg/kg patient weight, or 0.5 mg/kg patient weight, or 0.6 mg/kg patient weight.

According to certain aspects of the present disclosure, the radiolabeled anti-CD45 antibody (i.e., $^{225}$Ac-labelled BC8 or $^{177}$Lu-labelled BC8) may comprise a labeled fraction and an unlabeled fraction, wherein the ratio of labeled:unlabeled may be from about 0.01:10 to 1:10, such as 0.01:5 to 0.1:5, or 0.01:3 to 0.1:3, or 0.01:1 to 0.1:1 labeled:unlabeled. Moreover, the radiolabeled anti-CD45 antibody may be provided as a single dose composition tailored to a specific patient, wherein the amount of labeled and unlabeled anti-CD45 antibody in the composition may depend on at least a patient weight, age, gender, and/or disease state or health status. See for example administration methods disclosed in International Publication No. WO 2016/187514, incorporated herein by reference herein in its entirety. According to certain aspects, the radiolabeled anti-CD45 antibody may be provided in multiple doses, wherein each dose in the regime may comprise a composition tailored to a specific patient, wherein the amount of labeled and unlabeled anti-CD45 antibody in the composition may depend on at least a patient weight, age, gender, and/or disease state or health status.

This inventive combination of a labeled fraction and an unlabeled fraction of the anti-CD45 antibody allows the composition to be tailored to a specific patient, wherein each of the radiation dose and the protein dose of the monoclonal antibody are personalized to that patient based on at least one patient specific parameter. As such, each vial of the composition may be made for a specific patient, where the entire content of the vial is delivered to that patient in a single dose. When a treatment regime calls for multiple doses, each dose may be formulated as a patient specific dose in a vial to be administered to the patient as a "single dose" (i.e., full contents of the vial administered at one time). The subsequent dose may be formulated in a similar manner, such that each dose in the regime provides a patient specific dose in a single dose container. One of the advantages of the disclosed composition is that there will be no left-over radiation that would need to be discarded or handled by the medical personnel, e.g., no dilution, or other manipulation to obtain a dose for the patient. When provided in a single dose container, the container is simply placed in-line in an infusion tubing set for infusion to the patient. Moreover, the volume can be standardized so that there is a greatly reduced possibility of medical error (i.e., delivery of an incorrect dose, as the entire volume of the composition is to be administered in one infusion).

Treatment of Hematological Diseases

The majority of malignancies of hematologic origin, whether myeloid or lymphoid-derived, express CD45 on the surface of tumor cells to varying degrees. This includes leukemias (such as acute myeloid leukemia (AML), acute promyelocytic leukemia, acute lymphoblastic leukemia (ALL), acute mixed lineage leukemia, chronic myeloid leukemia, chronic lymphocytic leukemia (CLL), hairy cell leukemia and large granular lymphocytic leukemia), myelodysplastic syndrome (MDS), myeloproliferative disorders (polycythemia vera, essential thrombocytosis, primary myelofibrosis and chronic myeloid leukemia), lymphomas, multiple myeloma, MGUS and similar disorders, Hodgkin's lymphoma, non-Hodgkin lymphoma (NHL), primary mediastinal large B-cell lymphoma, diffuse large B-cell lymphoma, follicular lymphoma, transformed follicular lymphoma, splenic marginal zone lymphoma, lymphocytic lymphoma, T-cell lymphoma, and other B-cell malignancies. As such, an amount of a radiolabeled anti-CD45 antibody, when administered to a patient, will be effective as a direct anti-tumor therapy to reduce tumor blast count in the periphery and in the immune cell compartments, such as bone marrow, spleen and lymph nodes.

Direct therapy with a radiolabeled anti-CD45 antibody may be as a low-dose single agent necessary to reduce tumor blast count, but reversibly spare hematopoietic stem cells, or in combination with other therapeutic agents such as chemotherapy agents or targeted therapy agents (e.g., but not limited to: HDAC inhibitors, BCL2 inhibitors, monoclonal antibodies, or tyrosine kinase receptor inhibitors—TKIs).

Doses of an $^{225}$Ac radiolabeled anti-CD45 antibody effective at controlling tumor growth and reducing blast count without irreversibly depleting hematopoietic stem cells would deliver a radiation exposure to bone marrow below a threshold level. A dose of 2 Gy is considered to be a non-myeloablative dose of radiation. An ideal dose would deliver a dose of at least 2 Gy but high enough to eliminate leukemic or lymphoma tumor cells and provide transient but reversible myelosuppression. Dose levels above 2 Gy, but less than a myeloablative dose are anticipated to be effective at controlling tumor burden in lymphoma and leukemia. Further, combining single low-dose radiolabeled anti-CD45 antibody treatment with another targeted agent, potent anti-tumor activity may be achieved using lower doses of the antibody radioconjugate further sparing depletion of hematopoietic stem cells.

An exemplary low dose may be a dose of $^{225}$Ac-BC8 that is less than 150 µCi, such as from 10 µCi to 100 µCi, or a dose of less than 2 µCi/kg, such as from 0.01 µCi/kg to 1.5 µCi/kg or 0.1 µCi/kg to 1.0 µCi/kg.

Depletion of Circulating Tumor and Bone Marrow Blast Cells

Hematologic malignancies, including without limitation leukemias such as acute myeloid leukemia, acute lympho-cytic leukemia, multiple myeloma, etc., pose a unique set of problems for effective therapy. If killed too quickly, the high burden of circulating tumor cells often associated with leukemias can be toxic to the patient. Cytoreductive therapy is the process by which the number of circulating blast cells are reduced.

According to certain aspects, a cytoreductive therapy may be used to treat a hematological malignancy, and generally includes administration of a low dose of the radiolabeled anti-CD45, such as a dose that depletes the circulating tumor cells (e.g. leukemia, lymphoma, myeloma, MDS) but is not myeloablative and therefore does not irreversibly deplete HSCs. An exemplary low dose may be a dose of $^{225}$Ac-BC8 that is less than 150 μCi, such as from 10 μCi to 100 μCi, or a dose of less than 2 μCi/kg, such as from 0.01 μCi/kg to 1.5 μCi/kg or 0.1 μCi/kg to 1.0 μCi/kg.

Hematopoietic Stem Cell Therapy

The hematopoietic stem cell therapy includes administra-tion of hematopoietic stem cells, such as a bone marrow transplant (BMT). The hematopoietic stem cells may be administered to a patient defective or deficient in one or more cell types of the hematopoietic lineage in order to re-constitute the defective or deficient population of cells in vivo. For example, the patient may be suffering from cancer or from a hemoglobinopathy (e.g., a non-malignant hemo-globinopathy), such as sickle cell anemia, thalassemia, Fan-coni anemia, aplastic anemia, and Wiskott-Aldrich syn-drome. The subject may be one that is suffering from adenosine deaminase severe combined immunodeficiency (ADA SCID), HIV/AIDS, metachromatic leukodystrophy, Diamond-Blackfan anemia, and Schwachman-Diamond syndrome. The subject may have or be affected by an inherited blood disorder (e.g., sickle cell anemia) or an autoimmune disorder, such as scleroderma, multiple sclero-sis, ulcerative colitis, Crohn's disease, Type 1 diabetes, or another autoimmune pathology.

The cancer may be a neuroblastoma or a hematologic cancer. For instance, the subject may have a leukemia, lymphoma, or myeloma. In some embodiments, the subject has acute myeloid leukemia, acute lymphoid leukemia, chronic myeloid leukemia, chronic lymphoid leukemia, multiple myeloma, diffuse large B-cell lymphoma, or non-Hodgkin's lymphoma. The subject may have myelodysplas-tic syndrome (MDS).

Gene Editing

Gene editing technologies have advanced substantially with the advent of site-specific editing methods such as TALEN, CRISPR/cas9 and zinc finger nuclease (ZFN) methods. These methods have therapeutic potential for patients afflicted with malignant and non-malignant heredi-tary diseases.

Gene editing precisely and permanently alters a sequence of genomic DNA that remains under endogenous genetic regulation and control for proper and appropriate expression of the modified genetic element. There are presently four major classes of nucleases for human genome gene editing: zinc finger nucleases (ZFNs); transcription activator-like effector nucleases (TALENs); meganucleases (MNs); and clustered regularly interspaced short palindromic repeats (CRISPR/Cas9). Each of these can recognize and bind a specific target sequence of DNA. Depending on the approach, the target DNA can be cleaved on one or both strands. To correct a mutation, a correction template is used for homology-directed repair of the introduced break at the site of the targeted lesion. This technology can also be exploited to silence or ablate a particular gene by incorpo-rating a mutational insertion or deletion. Further, gene-editing technology can also be utilized to functionally replace one gene with another, such as within the T-cell receptor alpha constant locus (TRAC), and thereby change the specificity of the T-cells (Eyquem, et. al., 2017, Nature. 543:113-117).

Adoptive Cell Therapy ("ACT")

The adoptive cell therapy may include administration of cells expressing a chimeric antigen receptor (CAR), or a T-cell receptor (TCR), or may include tumor-infiltrating lymphocytes (TIL). The population of cells expressing the CAR/TCR may comprise a population of activated T-cells or natural killer (NK) cells or dendritic cells expressing the CAR/TCR which recognize an antigen. Dendritic cells are capable of antigen presentation, as well as direct killing of tumors. The population of cells expressing the CAR/TCR may comprise a population of gene-edited cells.

As used herein, the term "gene-edited" CAR T-cell is synonymous with the terms "genetically engineered" CAR T-cell and "engineered" CAR T-cell. A gene-edited CAR T-cell that "fails to properly express" a checkpoint receptor (e.g., PD1, Lag3 or TIM3) does not express the full-length, functional checkpoint receptor. For example, a gene-edited CAR T-cell that fails to properly express PD1 may fail to do so because, without limitation, (i) the cell's PD1 gene has been ablated, or (ii) the cell's PD1 gene has been otherwise altered so as not to yield a fully or even partially functional PD1 product. In other words, according to certain aspects, a gene-edited CAR T-cell that fails to properly express PD1 may fail to do so because the cell's PD1 gene has been altered to diminish PD1 expression. Similarly, a gene-edited CAR T-cell that "fails to properly express" a T-cell receptor does not express the full-length, functional T-cell receptor.

According to certain aspects, the functional endogenous T-cell receptor is replaced through editing by a "knock-in" to the native TCR locus of an exogenously transduced CAR or recombinant TCR. The gene-edited CAR T-cells may include, without limitation, the following: (i) allogenic gene-edited CAR T-cells that fail to properly express PD1 but do properly express all other checkpoint receptors and T-cell receptors; (ii) allogenic gene-edited CAR T-cells that fail to properly express a particular T-cell receptor but do properly express all checkpoint receptors and all other T-cell recep-tors; and (iii) allogenic gene-edited CAR T-cells that fail to properly express PD1 and fail to properly express a particu-lar T-cell receptor, but do properly express all other check-point receptors and all other T-cell receptors.

Examples of T-cell gene editing to generate allogeneic, universal CAR T-cells include the work of Eyquem and colleagues (Eyquem, et. al., 2017, Nature. 543:113-117). In that study, the endogenous T-cell receptor alpha constant locus (TRAC) was effectively replaced by a recombinant CAR gene construct. By this method, the recombinant CAR was placed effectively under the control of the cell's native TCR regulatory signals. By this same strategy, CARs or recombinant TCRs may be effectively inserted by knock-in into the T-cell receptor beta constant gene locus (TRBC) or into the beta-2 microglobulin (B2M) MHC-I-related gene locus, known to be expressed in all T-cells. Another example includes the work of Ren and colleagues (Ren, et. al., 2017, Clin. Cancer Res 23:2255-2266). Recognizing that check-point receptors are immune-suppressive and may blunt the stimulation of exogenous autologous or allogeneic CAR T-cells, this group exploited CRISPR/cas9 technology to ablate the endogenous TCR α and β loci (TRAC and TRBC) and the B2M gene, while also silencing the endogenous PD1 gene. With this approach, the engineered cells did not elicit graft-versus-host disease but did resist immune checkpoint receptor suppression.

Lymphodepletion and Myeloablation

Before administering a dose of HSTs (e.g., bone marrow transplant) or engineered immune cells to a patient, it is common to lymphodeplete the patient. The lymphodepletion process is considered important, indeed essential, to the success of BMT and adoptive cell therapy (ACT) methods. The process creates sufficient space in the immune microenvironment (e.g., bone marrow) to allow the transferred cells to engraft. It also creates a favorable immune homeostatic environment for the successful engraftment, proliferation, and persistence of the transferred cells by eliciting a favorable cytokine profile. It elicits this cytokine profile particularly in the peripheral immune niches (e.g., bone marrow, spleen and lymph nodes) for the establishment and proliferation of the engineered cells. (see, e.g., Maine, et al., 2002, J. Clin. Invest., 110:157-159; Muranski, et al., 2006, Nat. Clin. Pract. Oncol., 3(12):668-681; Klebanoff, et al., 2005, Trends Immunol., 26(2): 111-117).

As indicated hereinabove, myeloid and lymphoid-derived cell express CD45. Doses of an $^{225}$Ac radiolabeled anti-CD45 antibody effective at reducing blast count without irreversibly depleting hematopoietic stem cells would deliver a radiation exposure to bone marrow below a threshold level. A dose of 2 Gy is considered to be a non-myeloablative dose of radiation. A dose of at least 2 Gy may provide transient but reversible myelosuppression. Myeloablative doses are variable, such as in the range of 8-18 Gy, but typically include doses delivering more than 10-12 Gy to the bone marrow. Thus, a therapeutic low-dose range that may provide reversible immunosuppression (with or without stem cell support) would be 2 Gy or greater, but below a myeloablative dose, such as at or below 8 Gy. For higher doses, stem cell support may be necessary.

As used herein, an amount of a radiolabeled anti-CD45 antibody, when administered, is "effective" to deplete a specific targeted cell type if the cell population is reduced by at least 10%, 20%, 30%, 40%, 50%, 60%, 70%, 80%, 90% or 95%. For example, an amount of radiolabeled anti-CD45 antibody, when administered, is "effective" to deplete the subject's peripheral blood lymphocytes if the peripheral blood lymphocytes are depleted without depletion of the subject's neutrophils, or with less than 10% or 20% reduction in the subject's neutrophils. An "effective" amount of radiolabeled anti-CD45 antibody can also be related to an amount that will deplete the subject's regulatory T cells, myeloid derived suppressor cells, tumor associated macrophages, activated macrophages secreting IL-1 and/or IL-6, and combinations thereof, such as by at least 20%, or 30%, 40%, 50%, 60%, 70%, 80%, 90%, or 95%.

As used herein, an amount of a radiolabeled anti-CD45 antibody, when administered, is "effective" to reversibly suppress a targeted cell type if the cell population, such as the subject's HSC level or lymphocyte level, is reduced by greater than 95%, such as by at least 96%, or 97%, or 98%, or even 99%. "Reversible immunosuppression" generally comprises use of a low dose therapeutic or combination thereof, such as the actinium-225 labelled BC8 disclosed herein, to deplete the targeted cells to a greater extent than standard lymphodepletion without ablating the target cells, i.e., at a dose that is less than a myeloablation dose (non-myeloablative dose). Moreover, reversible immunosuppression may indicate that the targeted immune population (immune privileged cell population or tissues) is only transiently depleted, while other non-targeted populations are not affected.

As disclosed hereinbelow, reversible immunosuppression of the present disclosure generally may comprise administration of the actinium-225 labelled BC8 and another agent such as, for example, another immunotherapeutic agent or a radio-sensitizing agent.

As used herein, an amount of a radiolabeled anti-CD45 antibody, when administered, is "effective" to ablate a targeted cell type if the cell population, such as the subject's HSC level or lymphocyte level, is reduced by 100% (also referred to as myeloablation).

According to certain aspects of the present disclosure, the radiolabeled anti-CD45 antibody is actinium-225 labelled BC8 ($^{225}$Ac-labelled BC8), and the effective amount of $^{225}$Ac-labelled BC8 is below, for example, 5.0 μCi/kg (i.e., where the amount of $^{225}$Ac-BC8 administered to the subject delivers a radiation dose of below 5.0 μCi per kilogram of subject's body weight).

According to aspects of the present disclosure, the effective amount of the $^{225}$Ac-labelled BC8 is below 4.5 μCi/kg, 4.0 μCi/kg, 3.5 μCi/kg, 3.0 μCi/kg, 2.5 μCi/kg, 2.0 μCi/kg, 1.5 μCi/kg, 1.0 μCi/kg, 0.9 μCi/kg, 0.8 μCi/kg, 0.7 μCi/kg, 0.6 μCi/kg, 0.5 μCi/kg, 0.4 μCi/kg, 0.3 μCi/kg, 0.2 μCi/kg, 0.1 μCi/kg, 0.05 μCi/kg, or 0.01 μCi/kg. According to certain aspects, the effective amount of the $^{225}$Ac-labelled BC8 is at least 0.01 μCi/kg, or 0.05 μCi/kg, 0.1 μCi/kg, 0.2 μCi/kg, 0.3 μCi/kg, 0.4 μCi/kg, 0.5 μCi/kg, 0.6 μCi/kg, 0.7 μCi/kg, 0.8 μCi/kg, 0.9 μCi/kg, 1 μCi/kg, 1.5 μCi/kg, 2 μCi/kg, 2.5 μCi/kg, 3 μCi/kg, 3.5 μCi/kg, 4 μCi/kg, or 4.5 μCi/kg. According to certain aspects, the $^{225}$Ac-labeled BC8 may be administered at a dose that includes any combination of upper and lower limits as described herein, such as from at least 0.1 μCi/kg to below 5 μCi/kg, or from at least 0.5 μCi/kg to below 3 μCi/kg.

According to certain aspects, the effective amount of the $^{225}$Ac-labelled BC8 is below 1.0 mCi, such as below 0.5 mCi (i.e., wherein the $^{225}$Ac is administered to the subject in a non-weight-based dosage). According to certain aspects, the effective dose of the $^{225}$Ac-labelled BC8 may be below 1.0 mCi, such as below 0.9 mCi, 0.8 mCi, 0.7 mCi, 0.6 mCi, 0.5 mCi, 0.45 mCi, 0.4 mCi, 0.35 mCi, 0.3 mCi, 0.25 mCi, 0.2 mCi, 0.1 mCi, 90 μCi, 80 μCi, 70 μCi, 60 μCi, 50 μCi, 40 μCi, 30 μCi, 20 μCi, 10 μCi, or 5 μCi. The effective amount of $^{225}$Ac-labelled BC8 may be at least 2 μCi, such as at least 5 μCi, 10 μCi, 20 μCi, 30 μCi, 40 μCi, 50 μCi, 60 μCi, 70 μCi, 80 μCi, 90 μCi, 100 μCi, 120 μCi, 140 μCi, 160 μCi, 180 μCi, 200 μCi, 300 μCi, 400 μCi, 500 μCi, 600 μCi, 700 μCi, 800 μCi, or 900 μCi. According to certain aspects, the $^{225}$Ac-labelled BC8 may be administered at a dose that includes any combination of upper and lower limits as described herein, such as from at least 15 μCi to below 120 μCi, or from at least 20 μCi to below 100 μCi, or from 80 μCi to below 500 μCi. According to certain aspects, the $^{225}$Ac-labelled BC8 may be administered at a low dose. An exemplary low dose may be a dose of $^{225}$Ac-BC8 that is less than 150 μCi, such as from 10 μCi to 100 μCi, or a dose of less than 2 μCi/kg, such as from 0.01 μCi/kg to 1.5 μCi/kg or 0.1 μCi/kg to 1.0 μCi/kg.

According to certain aspects of the present disclosure, the radiolabeled anti-CD45 antibody is lutetium-177 labelled BC8 ($^{177}$Lu-labelled BC8), and the effective amount of $^{177}$Lu-labelled BC8 is below, for example, 500 μCi/kg (i.e., where the amount of $^{177}$Lu-BC8 administered to the subject delivers a radiation dose of below 500 μCi per kilogram of subject's body weight).

According to aspects of the present disclosure, the effective amount of the $^{177}$Lu-labelled BC8 is below 450 μCi/kg, 400 μCi/kg, 350 μCi/kg, 300 μCi/kg, 250 μCi/kg, 200 μCi/kg, 150 μCi/kg, 100 μCi/kg, 90 μCi/kg, 80 μCi/kg, 70 μCi/kg, 60 μCi/kg, 50 μCi/kg, 40 μCi/kg, 30 μCi/kg, 20 μCi/kg, 10 μCi/kg, 5 μCi/kg, or 1 μCi/kg. According to certain aspects, the effective amount of the $^{177}$Lu-labelled BC8 is at least 1 μCi/kg, 2.5 μCi/kg, 5 μCi/kg, 10 μCi/kg, 20 μCi/kg, 30 μCi/kg, 40 μCi/kg, 50 μCi/kg, 60 μCi/kg, 70 μCi/kg, 80 μCi/kg, 90 μCi/kg, 100 μCi/kg, 150 μCi/kg, 200 μCi/kg, 250 μCi/kg, 300 μCi/kg, 350 μCi/kg, 400 μCi/kg or 450 μCi/kg. According to certain aspects, an $^{177}$Lu-labeled BC8 may be administered at a dose that includes any combination of upper and lower limits as described herein, such as from at least 5 Ci/kg to below 50 μCi/kg, or from at least 50 Ci/kg to below 500 μCi/kg.

According to certain aspects, the effective amount of the $^{177}$Lu-labelled BC8 is below 20 mCi, such as below 15 mCi, 10 mCi, 9 mCi, 8 mCi, 7 mCi, 6 mCi, 5 mCi, 3 mCi, 2 mCi, 1 mCi, 800 μCi, 600 μCi, 400 μCi, 200 μCi, 100 μCi, or 50 μCi. The effective amount of $^{177}$Lu-labeled BC8 may be at least 10 μCi, such as at least 25 μCi, 50 μCi, 100 μCi, 200 μCi, 300 μCi, 400 μCi, 500 μCi, 600 μCi, 700 μCi, 800 μCi, 900 μCi, 1 mCi, 2 mCi, 3 mCi, 4 mCi, 5 mCi, 10 mCi, or 15 mCi. According to certain aspects, an $^{177}$Lu-labeled BC8 may be administered at a dose that includes any combination of upper and lower limits as described herein, such as from at least 10 Ci to below 20 mCi, or from at least 100 μCi to below 3 mCi, or from 3 mCi to below 20 mCi.

As used herein, a "suitable time period" after administering a radiolabeled anti-CD45 antibody to a subject and before performing an additional therapy on the subject is a time period sufficient to permit the administered antibody to deplete, reversibly suppress, or ablate the targeted cells of the subject, such as the subject's HSCs and/or lymphocytes. According to certain aspects, the suitable time period is fewer than 15 days, fewer than 14 days, fewer than 13 days, fewer than 12 days, fewer than 11 days, fewer than 10 days, fewer than 9 days, fewer than 8 days, fewer than 7 days, fewer than 6 days, fewer than 5 days, fewer than 4 days, or fewer than 3 days. According to certain aspects, the suitable time period is 1 day, 2 days, 3 days, 4 days, 5 days, 6 days, 7 days, 8 days, 9 days, 10 days, 11 days, 12 days, 13 days, 14 days, 15 days, or more than 15 days.

According to certain aspects, the suitable time period after administering the radiolabeled anti-CD45 antibody that an ACT procedure may be performed is 3 days, 4 days, 5 days, 6 days, 7 days, 8 days or 9 days, such as preferably 6, 7 or 8 days.

Throughout this application, various publications are cited. The disclosure of these publications is hereby incorporated by reference into this application to describe more fully the state of the art to which this disclosure pertains. Unless otherwise defined, all technical and scientific terms used herein have the same meaning as commonly understood by one of ordinary skill in the art to which the present disclosure belongs. Although methods and materials similar or equivalent to those described herein can be used in the practice or testing described herein, suitable methods and materials are described below.

DETAILED DESCRIPTION OF THE INVENTION

This disclosure solves an unmet need in the art by providing an unexpectedly superior way to deplete, reversibly immunosuppress, or ablate specific cells in a subject, such as the subject's hematopoietic stem cells or lymphocytes. Reversible immunosuppression of these cells may be useful in the treatment of a CD45 positive hematological malignancy, and may be achieved using low-dose therapeutics, such as administration of an anti-CD45 antibody at sub-saturating radiation doses.

Radiolabeled anti-CD45 antibodies have shown clinical potential for targeted myeloablative conditioning prior to bone marrow transplant. CD45 is an attractive target for conditioning as it is highly expressed in all nucleated immune cells including hematopoietic stem cells, lymphoid and myeloid cells. The potent alpha-emitter 225-Actinium ($^{225}$Ac) is a promising radionuclide for targeted conditioning, with high linear energy transfer (80-100 keV/μm) over a short path length, and a long 9.9-day half-life.

Moreover, depletion or ablation of these cells using a high dose therapeutic, i.e., higher radiation doses, may be a precursor to a cell-based therapy like a bone marrow transplant and/or an adoptive cell therapy (e.g., chimeric antigen receptor therapy, CAR T-cell therapy or TCR-cell therapy) or a gene-edited cell-based therapy (e.g., genetically edited β-globin hematopoietic stem cell therapy for sickle cell disease, SCD).

Accordingly, this disclosure employs a radiolabeled anti-CD45 antibody such as $^{225}$Ac-BC8 to deplete, reversibly immunosuppress, or ablate specific cells in a subject. The antibody can safely and effectively deplete or ablate the subject's hematopoietic stem cells or lymphocytes via targeted conditioning. This approach avoids certain adverse effects caused by less specific agents like chemotherapeutics or external beam radiation.

The present disclosure provides methods of treating a variety of disorders, such as diseases of a cell type in the hematopoietic lineage, cancers, autoimmune diseases, metabolic disorders, and stem cell disorders, among others. The compositions and methods described herein may (i) directly deplete or ablate a population of cells that give rise to a pathology, such as a population of cancer cells (e.g., leukemia cells) and autoimmune cells (e.g., autoreactive T-cells), and/or (ii) deplete or ablate a population of endogenous hematopoietic stem cells so as to promote the engraftment of transplanted hematopoietic stem cells by providing a niche to which the transplanted cells may home.

The foregoing activities can be achieved by administration of a composition comprising $^{225}$Ac-BC8 or $^{177}$Lu-BC8. In the case of direct treatment of a disease, this administration can cause a reduction in the quantity of the cells that give rise to the pathology of interest. In the case of preparing a patient for hematopoietic stem cell transplant therapy, this administration can cause the selective depletion, reversible suppression, or ablation of a population of endogenous hematopoietic stem cells, thereby creating a vacancy in the hematopoietic tissue, such as the bone marrow or lymphocytes, that can subsequently be filled by transplanted, exogenous hematopoietic stem cells, i.e. bone marrow transplant or adoptive cell transfer.

Radiolabeled Immunotherapeutic

According to aspects of the present disclosure, the anti-CD45 immunoglobulin BC8 may comprise $^{225}$Ac or $^{177}$Lu. According to certain preferred aspects, the anti-CD45 immunoglobulin BC8 may be radiolabeled with the alpha-emitting radionuclide Actinium-225 ($^{225}$Ac). The $^{225}$Ac payload conjugated to the monoclonal antibody BC8 delivers high energy alpha particles directly to the targeted cell(s), generating lethal double strand DNA breaks. Due to its short path length, the range of its high energy alpha particle emission is only a few cell diameters thick, thereby limiting damage to nearby non-malignant or normal tissues. As such, [225]Ac-BC8 may provide a therapeutically effective dose at lower radiation amounts than [117]Lu-BC8.

Furthermore, [225]Ac-antibody conjugates offer a crucial advantage over antibody-drug conjugates of the prior art as they are found to be effective even in patients with low target antigen expressing tumors. This is because of the large cytotoxic effects of the [225]Ac, which is in striking contrast to antibody-drug conjugates where hundreds of antibody molecules are needed to bind to their respective antigens to exert an effect on a targeted cell or tissue.

Other advantages of the radioactive payload over drugs or toxins include: 1) the antibody that delivers the radiation does not need to be internalized to kill the cell; 2) not every cell in the targeted tissue or tumor needs to be targeted by the antibody; and 3) In contrast to antibody-drug conjugates, the radioisotope linked to the antibody is unlikely to elicit significant immune responses that would limit subsequent use. Moreover, studies reported herein demonstrate the stability of the [225]Ac labelled antibodies, and their highly targeted cytotoxicity.

According to certain aspects of the present disclosure, the [225]Ac may be attached or chelated by a chelating agent that is conjugated to the monoclonal antibody. As detailed in Example 3 below, the anti-CD45-immunoglobulin may be prepared by first forming a chelator conjugated anti-CD45 ("conjugated anti-CD45"), and then chelating the radionuclide with the conjugated anti-CD45 to form the radiolabeled anti-CD45 (i.e., [225]Ac-BC8).

According to the methods of forming the radiolabeled anti-CD45 described herein, the monoclonal antibody against CD45 may be dissolved in a buffered solution comprising a chelant. The pH may be selected to optimize conditions for conjugation of the chelant with the antibody in a conjugation reaction mixture. The conjugation reaction mixture may comprise a bicarbonate buffer or a phosphate buffer. The conjugation reaction mixture may have a pH of about 8.0 to about 9.2. For example, the conjugation reaction mixture may have a pH of about 8.0, about 8.1, about 8.3, about 8.4, about 8.5, about 8.6, about 8.7, about 8.8, about 8.9, about 9.0, about 9.1, or about 9.2. The temperature of the conjugation reaction mixture may be adjusted to promote conjugation of the chelant with the targeting moiety. For example, the conjugation reaction mixture can be incubated at a temperature of about room temperature, or about 37° C. The conjugation reaction mixture may be incubated for any amount of time sufficient to provide conjugation such as, for example, about 1.5 hours.

The conjugated anti-CD45 may be dissolved in a buffered solution comprising a radionuclide. The pH may be selected to optimize conditions for chelation of the radionuclide with the conjugated anti-CD45 in a chelation reaction mixture. The chelation reaction mixture may have a pH of about 5.5 to about 7.0. For example, the chelation reaction mixture may have a pH of about 5.5, about 5.6, about 5.7, about 5.8, about 5.9, about 6.0, about 6.1, about 6.2, about 6.3, about 6.4, about 6.5, about 6.6, about 6.7, about 6.8, about 6.9 or about 7.0.

The temperature of the chelation reaction mixture may be adjusted to promote chelation of the radionuclide with the conjugated anti-CD45-immunoglobulin. For example, the chelation reaction mixture may be incubated at a temperature of about 37° C. The chelation reaction mixture may be incubated for about 1.5 hours. After a period of time, the solution may be quenched by the addition of a quenching chelate (e.g. diethylenetriaminepentaacetic acid (DTPA)) and the reaction mixture may be purified. The chelation reaction mixture may be further incubated after addition of the quenching chelate, such as for about 30 minutes at about 37° C. after addition of the quenching chelate.

The chelators useful in the present disclosure are compounds which have the dual functionality of sequestering metal ions plus the ability to covalently bind a biological carrier such as an antibody. Numerous chelators are known in the art. Exemplary chelators suitable for use in the present disclosure include, but are not limited to chelators such as S-2-(4-Isothiocyanatobenzyl)-1,4,7,10 tetraazacyclododecanetetraacetic acid (p-SCN-Bn-DOTA), diethylene triamine pentaacetic acid (DTPA); ethylene diamine tetraacetic acid (EDTA); 1,4,7,10-tetraazacyclododecane-N,N',N'',N'''-tetraacetic acid (DOTA); p-isothiocyanato-benzyl-1,4,7,10-tetraazacyclododecane-1,4,7,10-te-traacetic acid (p-SCN-Bz-DOTA); 1,4,7,10-tetraazacyclododecane-N,N',N''-triacetic acid (DO3A); 1,4,7,10-tetraazacyclo-dodecane-1,4,7,10-tetrakis(2-propionic acid) (DOTMA); 3,6,9-triaza-12-oxa-3,6,9-tricarboxymethylene-10-carboxy-13-phenyl-tridecanoic acid ("B-19036"); 1,4,7-triazacyclononane-N,N',N''-triacetic acid (NOTA); 1,4,8,11-tetraazacyclotetradecane-N,N',N'',N'''-tetraacetic acid (TETA); triethylene tetraamine hexaacetic acid (TTHA); trans-1,2-diaminohexane tetraacetic acid (CYDTA); 1,4,7,10-tetraazacyclododecane-1-(2-hydroxypropyl)-4,7,10-triacetic acid (HP-DO3A); trans-cyclohexane-diamine tetraacetic acid (CDTA); trans(1,2)-cyclohexane dietylene triamine pentaacetic acid (CDTPA); 1-oxa-4,7,10-triazacyclododecane-N,N',N''-triacetic acid (OTTA); 1,4,7,10-tetraazacyclododecane-1,4,7,10-tetrakis{3-(4-carboxyl)-butanoic acid}; 1,4,7,10-tetraazacyclododecane-1,4,7,10-tetrakis(acetic acid-methyl amide); 1,4,7,10-tetraazacyclododecane-1,4,7,10-tetrakis (methylene phosphonic acid); and derivatives thereof.

One or more steps may be used to separate the conjugated CD45 from other constituents of the conjugation reaction mixture or the radiolabeled anti-CD45 from other constituents of the chelation reaction mixture. For example, the reaction mixture can be transferred to a filtering device (e.g., a Millipore centrifugal device) having a particular molecular weight cut off such that filtration of the reaction mixture through the filtration device can separate the conjugated anti-CD45 or the radiolabeled anti-CD45 from other constituents of the respective reaction mixture. Filtration can be used to obtain a conjugated anti-CD45 or the radiolabeled anti-CD45 having at least about 60%, at least about 65%, at least about 70%, at least about 75%, at least about 80%, at least about 85%, at least about 90%, %, at least about 95%, at least about 97%, at least about 98%, at least about 99%, or at least about 99.5% purity.

According to certain aspects of the present disclosure, the yield of the conjugated anti-CD45-immunoglobulin or the radiolabeled anti-CD45-immunoglobulin from the separation (e.g., purification) is at least about 70%, at least about 75%, at least about 80%, at least about 85%, or at least about 90%, at least 95%, at least 96%, at least 97%, at least 98%, or at least 99% of the final product.

According to one aspect of the present disclosure, the monoclonal antibody may be first conjugated with a p-SCN-Bn-DOTA or DOTA chelating agent to form the conjugated anti-CD45-immunoglobulin, followed by chelation of [225]Ac by the p-SCN-Bn-DOTA or DOTA on the conjugated anti-CD45-immunoglobulin to form the radiolabeled anti-CD45-immunoglobulin. Thus, according to aspects of the present disclosure, only a single step involving [225]Ac is needed to label the anti-CD45-immunoglobulin.

According to certain aspects of the present disclosure, the radiolabeled anti-CD45-immunoglobulin $^{225}$Ac-BC8 is relatively stable. For example, greater than 85% of the $^{225}$Ac-BC8 may remain intact after storage for 24 hours at 4° C. (see FIG. 11). Moreover, the $^{225}$Ac-BC8 shows specificity toward CD45 expressing cells (see FIG. 12, 15A, 15B) and tissues (see FIG. 16A). The labeling efficiency, stability, and immunoreactivity of the $^{225}$Ac-BC8 combine to provide an effective therapeutic agent.

Radiolabeling with lutetium-177 ($^{177}$Lu) to provide $^{177}$Lu-DOTA-BC8 is also possible and within the scope of the present disclosure. Moreover, reference to $^{225}$Ac-BC8 or $^{177}$Lu-BC8 may include reference to either of $^{225}$Ac-DOTA-BC8 or $^{177}$Lu-DOTA-BC8, respectively, unless specifically indicated otherwise.

Methods for Depleting or Ablating Targeted Cells

This disclosure provides a method for depleting, reversibly suppressing, or ablating a subject's hematopoietic stem cells comprising administering to the subject an effective amount of a radiolabeled anti-CD45-immunoglobulin such as $^{225}$Ac-BC8. This disclosure provides a method for depleting a subject's lymphocytes comprising administering to the subject an effective amount of a radiolabeled anti-CD45-immunoglobulin such as $^{225}$Ac-BC8. This disclosure provides a method for depleting, reducing or eliminating a subject's hematopoietic cancer blasts comprising administering to the subject an effective amount of a radiolabeled anti-CD45-immunoglobulin such as $^{225}$Ac-BC8 alone as a single agent therapy or in combination with other therapies.

According to certain aspects of this method, the effective amount of $^{225}$Ac-BC8 is from 0.05 μCi/kg to 5.0 μCi/kg of subject's body weight. Examples of effective amounts include, without limitation, from 0.05 μCi/kg to 5.0 μCi/kg, such as from 0.1 μCi/kg to 0.2 μCi/kg, from 0.2 μCi/kg to 0.3 μCi/kg, from 0.3 μCi/kg to 0.4 μCi/kg, from 0.4 μCi/kg to 0.5 μCi/kg, from 0.5 μCi/kg to 0.6 μCi/kg, from 0.6 μCi/kg to 0.7 μCi/kg, from 0.7 μCi/kg to 0.8 μCi/kg, from 0.8 μCi/kg to 0.9 μCi/kg, from 0.9 μCi/kg to 1.0 μCi/kg, from 1.0 μCi/kg to 1.5 μCi/kg, from 1.5 μCi/kg to 2.0 μCi/kg, from 2.0 μCi/kg to 2.5 μCi/kg, from 2.5 μCi/kg to 3.0 μCi/kg, from 3.0 μCi/kg to 3.5 μCi/kg, from 3.5 μCi/kg to 4.0 μCi/kg, from 4.0 μCi/kg to 4.5 μCi/kg, or from 4.5 μCi/kg to 5.0 μCi/kg.

According to certain aspects of this method, the effective amount of $^{225}$Ac-BC8 is less than 1 mCi, such as less than 500 μCi. Examples of effective amounts include, without limitation, from 1 μCi to 500 μCi, such as from 10 μCi to 400 μCi, or 10 μCi to 300 μCi, 10 μCi to 200 μCi, 10 μCi to 100 μCi, 15 μCi to 75 μCi, 20 μCi to 75 μCi, 10 μCi to 50 μCi, 50 μCi to 100 μCi, 100 μCi to 150 μCi, 150 μCi to 200 μCi, 200 μCi to 250 μCi, 250 μCi to 300 μCi, 300 μCi to 350 μCi, 350 μCi to 400 μCi, 400 μCi to 450 μCi, or 450 μCi to 500 μCi.

An exemplary low dose may be a low dose of $^{225}$Ac-BC8 is less than 120 μCi, such as from 10 μCi to 100 μCi, or a dose of less than 2 μCi/kg, such as from 0.01 μCi/kg to 1.5 μCi/kg or 0.1 μCi/kg to 1.0 μCi/kg.

An exemplary high dose of $^{225}$Ac-BC8 may be a moderate to high dose of at least 120 μCi, such as from 120 μCi to 500 μCi, or a dose of at least 2 μCi/kg, such as from 2 μCi/kg to 5 μCi/kg, or 3 μCi/kg to 5 μCi/kg.

According to certain aspects of this method, the effective amount of $^{225}$Ac-BC8 is an amount effective to deplete a subject's hematopoietic stem cells or lymphocytes, such as an amount affective to deplete at least 25% of hematopoietic stem cells of the subject, or at least 50% of hematopoietic stem cells of the subject, or at least 70% of hematopoietic stem cells of the subject, or at least 80% of hematopoietic stem cells of the subject, or up to 90% of hematopoietic stem cells of the subject.

According to certain aspects of this method, the effective amount of $^{225}$Ac-BC8 is an amount effective to reversibly immunosuppress a subject's hematopoietic stem cells or lymphocytes, such as at least 90% of hematopoietic stem cells of the subject, or at least 92%, or at least 94%, or at least 96%, or up to 98% of hematopoietic stem cells of the subject without completely ablating the hematopoietic stem cells or lymphocytes of the subject.

According to certain aspects of this method, the effective amount of $^{225}$Ac-BC8 is an amount effective to deplete a subject's circulating tumor cells, such as hematopoietic stem cells or lymphocytes, such as an amount affective to deplete at least 25% of the hematopoietic stem cells or lymphocytes of the subject, or at least 50% of hematopoietic stem cells or lymphocytes of the subject, or at least 70% of hematopoietic stem cells or lymphocytes of the subject, or at least 80% of hematopoietic stem cells or lymphocytes of the subject, or up to 90% of hematopoietic stem cells or lymphocytes of the subject, without myeloablation. According to certain aspects, this amount may be a low dose of the $^{225}$Ac-BC8, such as less than 150 μCi or 120 μCi, such as from 10 μCi to 100 μCi, or a dose of less than 2 μCi/kg, such as from 0.01 μCi/kg to 1.5 μCi/kg or 0.1 μCi/kg to 1.0 μCi/kg. this dose may be administered alone or with further additional therapeutics, as disclosed hereinbelow.

According to certain aspects of this method, the effective amount of $^{225}$Ac-BC8 is an amount effective to deplete, reduce or eliminate a patient's hematopoietic cancer blasts by 25%, 50%, or 100% as a single agent or in combination with other therapies. A dose that is effective at depleting, reducing or eliminating a patient's cancer blasts may require stem cell support depending on the dose administered.

Stem cell support may be offered to the patient when such cells have been depleted or reversibly suppressed, or after complete ablation thereof. For example, treatment of a patient with a high cancer cell burden may require higher doses of the radiolabeled anti-CD45 antibody, and as such may result in depletion or suppression of a significant percent of the hematopoietic stem cells of the patient. In such a case, stem cell support may be needed to effect repopulation of those cells. According to certain aspects, stem cell support may not be needed, and a sufficient quantity of hematopoietic stem cells may be present and capable of repopulating.

According to certain aspects of this method, the effective amount of $^{225}$Ac-BC8 is an amount effective to ablate 100% of the hematopoietic stem cells of the subject (also referred to as myeloablation). Exemplary doses include at least those indicated herein as high doses.

The method generally comprises administering to the subject an effective amount of the $^{225}$Ac-BC8 in a single dose, such as a single patient specific dose. The amount of reduction of the lymphocytes or hematopoietic stem cells may be determined by any of the methods disclosed herein above. The dose of $^{225}$Ac-BC8 may depend on the amount of depletion or immunosuppression desired. For example, depletion of the hematopoietic stem cells may be achieved at low doses, such as less than 2 Gy of the $^{225}$Ac-BC8. Reversible immunosuppression of the hematopoietic stem cells may be achieved at doses of less than 8 Gy of the $^{225}$Ac-BC8, such as doses of 2 Gy to 8 Gy, and ablation may be achieved at high doses such as 8 Gy or greater of the $^{225}$Ac-BC8, such as about 10-12 Gy.

The method may further comprise administering to the subject an effective amount of the $^{225}$Ac-BC8 in a fractionated dose, such as multiple administrations of portions of a single patient specific dose, or administration of multiple single patient specific doses. When administered with a second agent, the dose of $^{225}$Ac-BC8 may depend on the amount of depletion or immunosuppression desired.

Methods for Treating Non-Malignant Hematological Disorders

This depletion method (also referred to herein as a conditioning method) may be useful, for example, for improving the outcome of a subsequent gene-edited cell-based therapy where the depletion of hematopoietic stem cells is desirable. According to certain aspects of this method, the subject is afflicted with a non-cancerous disorder treatable via genetically edited cell therapy and is about to undergo such therapy to treat the disorder. The present disclosure also provides a method for treating a subject afflicted with a non-cancerous disorder treatable via genetically edited cell therapy comprising (i) administering to the subject an amount of a radiolabeled anti-CD45 antibody effective to deplete the subject's hematopoietic stem cells, and (ii) after a suitable time period, performing the therapy on the subject to treat the subject's disorder.

Examples of non-cancerous disorders include, without limitation, hemoglobinopathies (e.g., SCD and β-thalassemia), congenital immunodeficiencies (e.g., SCID and Fanconi's anemia) and viral infections (e.g., HIV infection). According to certain aspects, the disorder is SCD and the therapy is genetically edited β-globin hematopoietic stem cell therapy. The stem cell therapy can be allogenic or autologous, for example. According to certain aspects, the disorder is SCID and the therapy is genetically edited hematopoietic stem cell therapy, wherein the edited gene is the common gamma chain (γc) gene, the adenosine deaminase (ADA) gene and/or the Janus kinase 3 (JAK3) gene. The stem cell therapy can be allogenic or autologous, for example.

According to certain preferred aspects of the subject method, the radiolabeled anti-CD45 antibody is radiolabeled BC8, such as $^{225}$Ac-BC8. The effective amount of the $^{225}$Ac-BC8 is an amount effective too deplete, reversibly suppress, or ablate the hematopoietic stem cells of the subject, and can be, for example, from 0.01 μCi/kg to 1.0 μCi/kg, from 1.0 μCi/kg to 3.0 μCi/kg, from 3.0 μCi/kg to 5.0 μCi/kg, or from 0.1 μCi/kg to 5.0 μCi/kg of the subject's weight. According to certain aspects, the method comprises (i) administering to the subject from 0.1 μCi/kg to 5.0 μCi/kg of $^{225}$Ac-BC8, and (ii) after 6, 7 or 8 days, performing the therapy on the subject to treat the subject's disorder. According to certain other aspects, the method comprises (i) administering to the subject from 0.1 μCi/kg to 1.0 μCi/kg of $^{225}$Ac-BC8, and (ii) after 6, 7 or 8 days, performing the therapy on the subject to treat the subject's disorder. According to yet further aspects, the method comprises (i) administering to the subject from 1.0 μCi/kg to 3.0 μCi/kg of $^{225}$Ac-BC8, and (ii) after 6, 7 or 8 days, performing the therapy on the subject to treat the subject's disorder. According to yet further aspects, the method comprises (i) administering to the subject from 3.0 μCi/kg to 5.0 μCi/kg of $^{225}$Ac-BC8, and (ii) after 6, 7 or 8 days, performing the therapy on the subject to treat the subject's disorder.

Methods for Treating Malignant Hematological Disorders

The present disclosure also provides a method for treating a subject afflicted with a malignant disease or disorder such as a cancer. The method may generally comprise administering to the subject an amount of a radiolabeled anti-CD45 antibody effective to deplete, reversibly suppress, or ablate the subject's HSC or lymphocytes or hematopoietic cancer blasts. According to at least one exemplary method, a low dose of a radiolabeled anti-CD45 antibody is administered to reduce or deplete the number of hematopoietic stem cells or lymphocytes, and/or circulating tumor cells, without myeloablation. The dose may be a low dose as defined herein.

According to certain aspects, the method may further comprise administering stem cell support. According to certain aspects, the method may further comprise performing a conditioning therapy after a suitable time period. The conditioning therapy may be a hematopoietic stem cell transplant, such as a bone marrow transplant, or an adoptive cell therapy on the subject to treat the subject's cancer.

According to certain aspects of this method, the subject is afflicted with cancer and is about to undergo adoptive cell therapy to treat the cancer. Adoptive cell therapy is known, and includes, for example, CAR T-cell therapy (e.g., autologous cell therapy and allogeneic cell therapy). Adoptive cell therapies provide a method of promoting regression of a cancer in a subject, and generally comprise (i) collecting autologous T-cells (leukapheresis); (ii) expanding the T-cells (culturing); (iii) administering to the subject nonmyeloablative lymphodepleting chemotherapy; and (iv) after administering nonmyeloablative lymphodepleting chemotherapy, administering to the subject the expanded T-cells. The methods of the present disclosure include using a radiolabeled anti-CD45 antibody in lieu of the lymphodepleting chemotherapy, and/or after administration of the expanded cells (e.g., T-cell, NK-cells, dendritic cells, etc.). This later administration of the anti-CD45 antibody (i.e., after administration of the expanded cells) may be used in preparation for transplantation of autologous stem cells (HSCT), or administration of a second effective amount or number of expanded cells.

Accordingly, the present disclosure provides methods for the treatment of a proliferative disease, such as a hematological malignancy, which include administration of a radiolabeled anti-CD45 antibody and an adoptive cell therapy. The adoptive cell therapy may generally include apheresis of autologous cells which may be gene edited prior to reinfusion (adoptive cell therapy such as CAR T-cell therapy) after lymphodepletion by the radiolabeled anti-CD45 antibody. Alternatively, allogeneic cells may be reinfused after lymphodepletion to provide the adoptive cell therapy. According to methods of the present disclosure, the radiolabeled anti-CD45 antibody may be provided as a single dose 3 to 9 days, such as 6 to 8 days, prior to the adoptive cell therapy.

According to certain aspects of this method, the radiolabeled anti-CD45 antibody is radiolabeled BC8 as described hereinabove, provided at the doses as described hereinabove, wherein the dose generally depends on the specific radionuclide label (e.g., $^{225}$Ac-BC8). According to certain aspects of this method, the suitable time period after administering the radiolabeled anti-CD45 antibody is 3 days, 4 days, 5 days, 6 days, 7 days, 8 days or 9 days, such as preferably 6, 7 or 8 days.

According to certain aspects, the method for treating a subject afflicted with cancer consists of (i) administering to the subject a single dose of a radiolabeled anti-CD45 antibody effective to deplete the subject's lymphocytes, and (ii) after a suitable time period (e.g., 6, 7 or 8 days), performing adoptive cell therapy on the subject to treat the subject's cancer. According to certain aspects, the method for treating a subject afflicted with cancer consists of (i) administering to the subject a single dose of a radiolabeled anti-CD45 antibody effective to deplete the subject's lymphocytes, and (ii) after a suitable time period (e.g., 6, 7 or 8 days), performing adoptive cell therapy on the subject to treat the subject's cancer.

According to certain aspects of this method, the effective amount of $^{225}$Ac-BC8 is from 0.01 µCi/kg to 5.0 µCi/kg of subject's body weight.

According to certain aspects, the method for treating a subject afflicted with cancer consists of (i) administering to the subject a single dose of a radiolabeled anti-CD45 anti-body effective to myelosuppress the subject, and (ii) after a suitable time period (e.g., 4, 5, 6, 7 or 8 days), performing a bone marrow transplant on the subject to treat the subject's cancer. According to certain aspects, the method for treating a subject afflicted with cancer consists of (i) administering to the subject a single dose of a radiolabeled anti-CD45 anti-body effective to deplete the subject's myelocytes, and (ii) after a suitable time period (e.g., 4, 5, 6, 7 or 8 days), performing a bone marrow transplant on the subject to treat the subject's cancer.

According to certain aspects of this method, the effective amount of $^{225}$Ac-BC8 is a low dose, such as a dose of less than 120 µCi, such as from 10 µCi to 100 µCi, or a dose of less than 2 µCi/kg, such as from 0.01 µCi/kg to 1.5 µCi/kg or 0.1 µCi/kg to 1.0 µCi/kg.

Additional Therapeutic Agents

The presently disclosed compositions and methods may be used in combination with certain additional therapeutic agents. For example, additional immunotherapeutic agents may be administered in combination with the anti-CD45 antibody compositions disclosed herein. Exemplary additional immunotherapeutic agents include at least antibodies against CD33 and/or CD38 (see for example International Publication No. WO 2019/094931, incorporated herein by reference herein in its entirety), and/or antibodies against CD34, CD117, and/or CD135 (see for example U.S. Provisional Patent application Nos. 62/838,646 and 62/838,589. Incorporated herein by reference in their entirety).

The presently disclosed compositions and methods may be used in combination with a radiosensitizer, which may enhance the efficacy of the disclosed radioimmunotherapy (e.g., $^{225}$Ac-BC8). For example, Bcl-2 inhibitors may be active against a number of cancer cell lines in combination with radiation, such as provided by the $^{225}$Ac-BC8. Additionally, small molecule inhibitors of Bcl-2 proteins display synergy with other anticancer agents, including, but not limited to etoposide, doxorubicin, cisplatin, paclitaxel, and radiation.

Inhibiting apoptosis is widely accepted as a necessary step in the transition from normal to cancer cells, and several cancer therapies exert their effects by reversing this process. Commitment to apoptosis is caused by permeabilization of the outer mitochondrial membrane—a process regulated by the binding between different members of the Bcl-2 family. Furthermore, Bcl-2 family members also bind to the endo-plasmic reticulum, where they modify processes such as the unfolded-protein response and autophagy that also cause or modify different types of cell death.

Bcl-2 overexpression was initially described in follicular lymphomas as a consequence of a t(14; 18) translocation, and as a poor prognostic marker in acute myelogenous leukemia (AML) and non-Hodgkin's lymphomas. Overexpression of Bcl-2 was subsequently described in prostate, breast and colon carcinomas, as well as glioblastomas. Overexpression of Mcl-1, another anti-apoptotic, Bcl-2-related protein, was identified in relapsed AML, and was associated with poor prognosis. Other changes in Bcl-2- related protein expression identified in cancer cells include different mutations in the Bax gene, and changes in the proapoptotic to antiapoptotic Bcl-2 protein ratio. The inability of cancer cells to execute an apoptotic program due to defects in the normal apoptotic machinery is thus often associated with an increase in resistance to radiation and/or immunotherapy-induced apoptosis.

Accordingly, the presently disclosed methods may include addition of a radiosensitizer such as a Bcl-2 inhibitor that may act to directly or indirectly induce apoptosis in cancer cells in a manner that is synergistic with the radio-labeled-anti-CD45 antibody. Bcl-2 inhibitors include small molecule and antisense oligonucleotide drugs, such as AT-101 ((−)gossypol), GENASENSE® (G3139 or oblimersen; Bcl-2-targeting antisense oligonucleotide), IPI-194, IPI-565, ABT-737, ABT-263, GX-070 (obatoclax) and the like.

According to preferred aspects, the Bcl-2 inhibitor may be venetoclax, a drug that has been approved for treating chronic lymphocytic leukemia ("CLL"). Venetoclax binds to the BH3-binding groove of BCL-2, displacing pro-apoptotic proteins like BIM to initiate mitochondrial outer membrane permeabilization ("MOMP"), the release of cytochrome c, and caspase activation, ultimately resulting in programmed cancer cell death (i.e., apoptosis). Ideally, by changing the balance between pro-apoptotic and anti-apoptotic stimuli, venetoclax would facilitate programed cell death of cancer cells and thus improve patient outcomes.

According to certain aspects, the presently disclosed radioimmunotherapy (e.g., $^{225}$Ac-BC8), may be used in combination with a BCL-2 inhibitor such as venetoclax to provide a method for treating a subject afflicted with cancer, comprising administering to the subject (i) a BCL-2 inhibitor in conjunction with (ii) the radiolabeled anti-CD45 antibody (e.g., $^{225}$Ac-BC8), wherein the amounts of the BCL-2 inhibitor and radiolabeled anti-CD45 antibody, when administered in conjunction with one another, are therapeutically effective to treat the cancer.

This disclosure also provides a method for treating a human subject afflicted with a hematological disease or disorder, comprising administering to the subject (i) a BCL-2 inhibitor such as venetoclax in conjunction with (ii) $^{225}$Ac-BC8, wherein the amounts of venetoclax and $^{225}$Ac-BC8, when administered in conjunction with one another, are therapeutically effective to treat the acute myeloid leukemia.

As used herein, administering to a subject a BCL-2 inhibitor "in conjunction with" a radiolabeled anti-CD45 antibody such as $^{225}$Ac-BC8 means administering the BCL-2 inhibitor before, during or after administration of the $^{225}$Ac-BC8. This administration includes, without limitation, the following scenarios: (i) the BCL-2 inhibitor is administered first (e.g., orally once per day for 21 days, 28 days, 35 days, 42 days, 49 days, or a longer period during which the cancer being treated does not progress and during which the BCL-2 inhibitor does not cause unacceptable toxicity), and the $^{225}$Ac-BC8 is administered second (e.g., intravenously in a single dose or a plurality of doses over a period of weeks); (ii) the BCL-2 inhibitor is administered concurrently with the $^{225}$Ac-BC8 (e.g., the BCL-2 inhibitor is administered orally once per day for n days, and the $^{225}$Ac-BC8 is administered intravenously in a single dose on one of days 2 through n-1 of the BCL-2 inhibitor regimen); (iii) the BCL-2 inhibitor is administered concurrently with the $^{225}$Ac-BC8 (e.g., the BCL-2 inhibitor is administered orally for a duration of greater than one month (e.g., orally once per day for 35 days, 42 days, 49 days, or a longer period during which the cancer being treated does not progress and during which the BCL-2 inhibitor does not cause unacceptable toxicity), and the $^{225}$Ac-BC8 is administered intravenously in a single dose on a day within the first month of the BCL-2 inhibitor regimen); and (iv) the $^{225}$Ac-BC8 is administered first (e.g., intravenously in a single dose or a plurality of doses over a period of weeks), and the BCL-2 inhibitor is administered second (e.g., orally once per day for 21 days, 28 days, 35 days, 42 days, 49 days, or a longer period during which the cancer being treated does not progress and during which the BCL-2 inhibitor does not cause unacceptable toxicity).

The amount of the radiolabeled anti-CD45 antibody administered may be sufficient to deplete, reversibly immunosuppress, or ablate the hematological stem cells in the patient. In general, the dose of the radiolabeled anti-CD45 antibody is a sub-saturating dose that may reversibly immunosuppress the hematological stem cells.

Additional radiosensitizing agents include, for example, histone deacetylase inhibitors (HDACi) such as vorinostat, belinostat, and romidepsin; metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2, 4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like.

The term "histone deacetylase inhibitor" or "HDACi" refers to histone deacetylase inhibitors that can be grouped in four classes: hydroxamates (panobinostat (LBH-589), trichostatin-A (TSA), vorinostat (SAHA), belinostat (PXD101), NVP-LAQ824 and givinostat (ITF2357)), cyclic peptide (romidepsin (depsipeptide)), aliphatic acids (valproic acid (VPA) and sodium phenylbutyrate) and benzamides (MS-275, MGCD0103). HDACi are characterized as class I-specific HDACs inhibitors (MGCD0103, romidepsin and MS-275) or as pan-HDAC inhibitors, denoting activity against both classes I and II HDACs (TSA, panobinostat, vorinostat and belinostat).

Histone deacetylase inhibitors are recognized to exert multiple cytotoxic actions in cancer cells, often through acetylation of non-histone proteins. Some well-recognized mechanisms of HDACi lethality include, in addition to relaxation of DNA and de-repression of gene transcription, interference with chaperone protein function, free radical generation, induction of DNA damage, up-regulation of endogenous inhibitors of cell cycle progression, and promotion of apoptosis. Intriguingly, this class of agents is relatively selective for transformed cells where they have been found to cause DNA repair to be halted after chemotherapy, and to promote the efficacy of chemotherapy.

According to certain aspects, the presently disclosed radioimmunotherapy (e.g., $^{225}$Ac-BC8), may be used in combination with an HDACi such as vorinostat, belinostat, or romidepsin to provide a method for treating a subject afflicted with cancer, comprising administering to the subject (i) an HDACi in conjunction with (ii) the radiolabeled anti-CD45 antibody (e.g., $^{225}$Ac-BC8), wherein the amounts of the HDACi and radiolabeled anti-CD45 antibody, when administered in conjunction with one another, are therapeutically effective to treat the cancer.

This disclosure also provides a method for treating a human subject afflicted with a hematological disease or disorder, comprising administering to the subject (i) an HDACi such as vorinostat, belinostat, or romidepsin in conjunction with (ii)$^{225}$Ac-BC8, wherein the amounts of the HDACi and $^{225}$Ac-BC8, when administered in conjunction with one another, are therapeutically effective to treat the acute myeloid leukemia.

As with the BCL-2 inhibitors, administering to a subject an HDACi "in conjunction with" a radiolabeled anti-CD45 antibody such as $^{225}$Ac-BC8 means administering the HDACi before, during or after administration of the $^{225}$Ac-BC8. This administration includes, without limitation, the following scenarios: (i) the HDACi is administered first (e.g., orally once per day for 21 days, 28 days, 35 days, 42 days, 49 days, or a longer period during which the cancer being treated does not progress and during which the HDACi does not cause unacceptable toxicity, or intravenously on days 1, 8, 15, of a 28 day cycle), and the $^{225}$Ac-BC8 is administered second (e.g., intravenously in a single dose or a plurality of doses over a period of weeks); (ii) the HDACi is administered concurrently with the $^{225}$Ac-BC8 (e.g., the HDACi is administered orally once per day for n days, or intravenously for n days, and the $^{225}$Ac-BC8 is administered intravenously in a single dose on one of days 2 through n−1 of the HDACi regimen); (iii) the HDACi is administered concurrently with the $^{225}$Ac-BC8 (e.g., the HDACi is administered orally for a duration of greater than one month as described herein, and the $^{225}$Ac-BC8 is administered intravenously in a single dose on a day within the first month of the HDACi regimen); and (iv) the $^{225}$Ac-BC8 is administered first (e.g., intravenously in a single dose or a plurality of doses over a period of weeks), and the HDACi is administered second (as described herein).

Article of Manufacture

The present disclosure further provides an article of manufacture comprising (a) a radiolabeled anti-CD45-immunoglobulin, and (b) a label instructing the user to administer to a subject an amount of the immunoglobulin effective to deplete the subject's hematopoietic stem cells.

According to certain aspects of the subject article, the radiolabeled anti-CD45-immunoglobulin is $^{225}$Ac-BC8, wherein the effective amount can be, for example, from 0.01 μCi/kg to 5.0 μCi/kg, or from 0.01 μCi/kg to 1.0 μCi/kg of the $^{225}$Ac-BC8, or from 1.0 μCi/kg to 3.0 μCi/kg of the $^{225}$Ac-BC8, or from 3.0 μCi/kg to 5.0 μCi/kg of the $^{225}$Ac-BC8, or from 10 μCi to 120 μCi of the $^{225}$Ac-BC8, or from 100 μCi to 250 μCi of the $^{225}$Ac-BC8, or from 200 μCi to 500 μCi of the $^{225}$Ac-BC8, or from 5 μCi to 80 μCi of the $^{225}$Ac-BC8.

According to certain aspects of the subject article, the radiolabeled anti-CD45-immunoglobulin is $^{177}$Lu-BC8, wherein the effective amount can be, for example, from 1 μCi/kg to 500 μCi/kg, or from 1 μCi/kg to 100 μCi/kg of the $^{177}$Lu-BC8, or from 100 μCi/kg to 300 μCi/kg of the $^{177}$Lu-BC8, or from 300 μCi/kg to 500 μCi/kg of the $^{177}$Lu-BC8.

This disclosure will be better understood by reference to the examples which follow, but those skilled in the art will readily appreciate that the specific examples detailed are only illustrative of the disclosure as described more fully in the claims which follow thereafter.

Aspects of the Invention

The following aspects are disclosed in this application:

Aspect 1. A method for depleting a subject's hematopoietic stem cells comprising administering to the subject an effective amount of a radiolabeled anti-CD45-immunoglobulin.

Aspect 2. The method of aspect 1, wherein the effective amount of the radiolabeled anti-CD45-immunoglobulin depletes at least 25% of hematopoietic stem cells of the subject, or 50% of hematopoietic stem cells of the subject, or at least 70% of hematopoietic stem cells of the subject, or at least 80% of hematopoietic stem cells of the subject, or at least 90% of hematopoietic stem cells of the subject, or at least 95% of hematopoietic stem cells of the subject, or not more than 90% of hematopoietic stem cells of the subject, or not more than 95% of hematopoietic stem cells of the subject.

Aspect 3. The method of aspect 1, wherein the effective amount of the radiolabeled anti-CD45-immunoglobulin depletes at least 90% of hematopoietic stem cells of the subject, or at least 95% of hematopoietic stem cells of the subject, or at least 98% of hematopoietic stem cells of the subject, or at least 99% of hematopoietic stem cells of the subject, or not more than 98% of hematopoietic stem cells of the subject, or not more than 99 of hematopoietic stem cells of the subject.

Aspect 4. The method according to any one of aspects 1 to 3, further comprising: administering an effective amount of a second therapeutic agent comprising one or more of an immunotherapeutic agent, a radiosensitizer, or a chemotherapeutic agent.

Aspect 5. The method of aspect 4, wherein the immunotherapeutic agent comprises one or more antibodies against CD33, CD34, CD38, CD119, and CD135.

Aspect 6. The method of aspect 4, wherein the radiosensitizer comprises a Bcl-2 inhibitor, or an HDAC inhibitor (HDACi).

Aspect 7. The method of aspect 1, wherein the effective amount of the radiolabeled anti-CD45-immunoglobulin depletes 100% of hematopoietic stem cells of the subject (i.e., ablates the hematopoietic stem cells).

Aspect 8. A method for depleting a subject's lymphocytes comprising administering to the subject an effective amount of a radiolabeled anti-CD45-immunoglobulin.

Aspect 9. The method of aspect 8, wherein the effective amount of the radiolabeled anti-CD45-immunoglobulin depletes at least 25% of lymphocytes of the subject, or 50% of lymphocytes of the subject, or at least 70% of lymphocytes of the subject, or at least 80% of lymphocytes of the subject, or at least 90% of lymphocytes of the subject, or at least 95% of lymphocytes of the subject, or at least 98% of lymphocytes of the subject, or at least 99% of lymphocytes of the subject, or not more than 90% of lymphocytes of the subject, or not more than 95% of lymphocytes of the subject, or not more than 98% of lymphocytes of the subject, or not more than 99% of lymphocytes of the subject.

Aspect 10. The method of aspect 8, wherein the effective amount of the radiolabeled anti-CD45-immunoglobulin depletes at least 25% of hematopoietic cancer blasts of the subject, or 50% of hematopoietic cancer blasts of the subject, or at least 70% of hematopoietic cancer blasts of the subject, or at least 80% of hematopoietic cancer blasts of the subject, or at least 90% of hematopoietic cancer blasts of the subject, or at least 95% of hematopoietic cancer blasts of the subject, or at least 98% of hematopoietic cancer blasts of the subject, or at least 99% of hematopoietic cancer blasts of the subject, or not more than 90% of hematopoietic cancer blasts of the subject, or not more than 95% of hematopoietic cancer blasts of the subject, or not more than 98% of hematopoietic cancer blasts of the subject, or not more than 99% of hematopoietic cancer blasts of the subject.

Aspect 11. The method of aspect 8, wherein the effective amount of the radiolabeled anti-CD45-immunoglobulin depletes 100% of lymphocytes of the subject (i.e., ablates the lymphocytes), or 100% of the hematopoietic cancer blasts of the subject.

Aspect 12. The method according to any one of aspects 1 to 11, wherein the subject is afflicted with a non-cancerous disorder treatable via genetically edited cell therapy and is about to undergo such therapy to treat the disorder, and the effective amount of the radiolabeled anti-CD4-immunoglobulin is administered as a single dose.

Aspect 13. A method for treating a subject afflicted with a non-cancerous disorder treatable via genetically edited cell therapy comprising (i) administering to the subject an amount of a radiolabeled anti-CD45-immunoglobulin effective to deplete the subject's hematopoietic stem cells, and (ii) after a suitable time period, performing the therapy on the subject to treat the subject's disorder.

Aspect 14. The method according to aspect 12 or 13, wherein the disorder is selected from the group consisting of a hemoglobinopathy, a congenital immunodeficiency, and a viral infection.

Aspect 15. The method according to aspect 14, wherein the disorder is selected from the group consisting of sickle cell disease (SCD), severe combined immunodeficiency disease (SCID), β-thalassemia and Fanconi's anemia.

Aspect 16. The method of aspect 14, wherein the disorder is SCD and the therapy is genetically edited β-globin hematopoietic stem cell therapy.

Aspect 17. The method of aspect 14, wherein the disorder is SCID and the therapy is genetically edited hematopoietic stem cell therapy, wherein the edited gene is selected from the group consisting of the common gamma chain (γc) gene, the adenosine deaminase (ADA) gene and the Janus kinase 3 (JAK3) gene.

Aspect 18. The method according to any one of aspects 1 to 7, wherein the subject is afflicted with a cancerous disorder and is about to undergo a hematopoietic stem cell transplant such as a bone marrow transplant to treat the disorder, and wherein the effective amount of the radiolabeled anti-CD4-immunoglobulin is administered as a single dose.

Aspect 19. The method according to any one of aspects 8 to 11, wherein the subject is afflicted with a cancerous disorder treatable via genetically edited cell therapy and is about to undergo such therapy to treat the disorder, and the effective amount of the radiolabeled anti-CD4-immunoglobulin is administered as a single dose.

Aspect 20: A method for treating a subject afflicted with a cancerous disorder treatable via genetically edited cell therapy comprising (i) administering to the subject an amount of a radiolabeled anti-CD4-immunoglobulin effective to deplete the subject's lymphocytes, and (ii) after a suitable time period, performing the therapy on the subject to treat the subject's disorder.

Aspect 21: The method according to any one of aspects 18 to 20, wherein the cancerous disorder is acute myeloid leukemia, acute lymphoid leukemia, chronic myeloid leukemia, chronic lymphoid leukemia, multiple myeloma, diffuse large B-cell lymphoma, of non-Hodgkin's lymphoma.

Aspect 22: The method according to aspects 19 or 20, wherein the genetically edited cell therapy is an adoptive cell therapy to treat the cancerous disorder.

Aspect 23: The method according to aspect 22, wherein the adoptive cell therapy is CAR T-cell therapy, wherein the CAR T-cell therapy comprises the administration of gene-edited CAR T-cells, and wherein the gene-edited CAR T-cells fail to properly express at least one checkpoint receptor and/or at least one T-cell receptor.

Aspect 24: The method according to aspect 23, wherein the CAR T-cell therapy is autologous cell therapy.

Aspect 25: The method according to aspect 23, wherein the CAR T-cell therapy is allogeneic cell therapy.

Aspect 26: The method according to any one of aspects 1 to 25, wherein the radiolabeled anti-CD45 antibody is $^{225}$Ac-BC8 or $^{177}$Lu-BC8.

Aspect 27. The method according to aspect 26, wherein the effective amount of $^{225}$Ac-BC8 is from 0.01 μCi/kg to 5.0 μCi/kg subject weight, or from 0.01 μCi/kg to 1.0 μCi/kg subject weight, or from 1.0 μCi/kg to 3.0 μCi/kg subject weight, or from 3.0 μCi/kg to 5.0 μCi/kg subject weight; OR wherein the effective amount of $^{225}$Ac-BC8 is from 2 μCi to below 0.5 mCi, or from at least 2 μCi to below 120 μCi, or from 10 μCi to below 120 μCi, or from 50 μCi to below 250 μCi; OR wherein the effective amount of $^{177}$Lu-BC8 is from 1 μCi/kg to 500 μCi/kg subject weight, or from 1 μCi/kg to 100 μCi/kg subject weight, or from 100 μCi/kg to 300 μCi/kg subject weight, or from 300 μCi/kg to 500 μCi/kg subject weight; OR wherein the effective amount of $^{177}$Lu-BC8 is from 10 Ci to 20 mCi, or from 100 μCi to 3 mCi, or from 3 mCi to 20 mCi.

Aspect 28: The method according to any one of aspects 1 to 27, wherein the anti-CD45-immunoglobulin comprises BC8, wherein the BC8 comprises a light chain having the amino acid sequence as set forth in SEQ ID NO:1, or a light chain N-terminal amino acid sequence as set forth in SEQ ID NO: 9.

Aspect 29: The method according to any one of aspects 1 to 28, wherein the anti-CD45-immunoglobulin comprises BC8, wherein the light chain of the BC8 comprises at least one complementarity determining region having the amino acid sequence as set forth in SEQ ID NO:3, SEQ ID NO:4, or SEQ ID NO:5.

Aspect 30: The method according to any one of aspects 1 to 29, wherein the anti-CD45-immunoglobulin comprises BC8, wherein the BC8 comprises a light chain having the amino acid sequence set forth in SEQ ID NO:12 or SEQ ID NO: 13.

Aspect 31: The method according to any one of aspects 1 to 30, wherein the anti-CD45-immunoglobulin comprises BC8, wherein the BC8 comprises a heavy chain having the amino acid sequence set forth in SEQ ID NO:2, or a heaving chain N-terminal amino acid sequence as set forth in SEQ ID NO: 10.

Aspect 32: The method according to any one of aspects 1 to 31, wherein the anti-CD45-immunoglobulin comprises BC8, wherein the heavy chain of the BC8 comprises at least one complementarity determining region having the amino acid sequence as set forth in SEQ ID NO:6, SEQ ID NO:7, or SEQ ID NO:8.

Aspect 33: The method according to any one of aspects 1 to 32, wherein the anti-CD45-immunoglobulin comprises BC8, wherein the BC8 comprises a heavy chain having the amino acid sequence set forth in SEQ ID NO:15 or SEQ ID NO:16.

Aspect 34: The method according to any one of aspects 1 to 33, wherein the anti-CD45-immunoglobulin comprises BC8, and the heavy chain of the BC8 comprises the amino acid ASP or ASN at position 141 (relative to the N-terminal amino acid).

Aspect 35: The method according to aspect 34, wherein a ratio of ASP:ASN in a population of BC8 proteins within the range 1:99 to 99:1, such as 10:90 to 90:10.

Aspect 36: The method according to any one of aspects 1 to 35, wherein the anti-CD45-immunoglobulin comprises BC8 that has been modified to comprise a heavy chain constant region from human IgG1, IgG2, or IgG4, i.e., the amino acid sequence as set forth in one of SEQ ID NOS: 17-19.

Aspect 37: The method according to any one of aspects 1 to 36, wherein the anti-CD45-immunoglobulin comprises BC8 that has been modified to comprise a heavy chain constant region from human IgG4 comprising the mutation S228P, having the amino acid sequence as set forth in SEQ ID NO:20.

Aspect 38: The method according to any one of aspects 1 to 37, wherein the anti-CD45-immunoglobulin comprises BC8 that has been modified to comprise a light chain kappa constant region from human having the amino acid sequence as set forth in SEQ ID NO:21.

Aspect 39. An article of manufacture comprising (a) a radiolabeled anti-CD45 antibody, and (b) a label instructing the user to administer to a subject an amount of the antibody effective to deplete or ablate the subject's hematopoietic stem cells or the subject's lymphocytes.

Aspect 40. The article of aspect 39, wherein the radiolabeled BC8 is $^{225}$Ac-BC8, and the effective amount of $^{225}$Ac-BC8 is from 0.01 μCi/kg to 5.0 μCi/kg, or from 0.01 μCi/kg to 1.0 μCi/kg subject weight, or from 1.0 μCi/kg to 3.0 μCi/kg subject weight, or from 3.0 μCi/kg to 5.0 μCi/kg subject weight; OR wherein the effective amount of $^{225}$Ac-BC8 is from 2 μCi to below 0.5 mCi, or from 2 μCi to 250 μCi, or from 75 μCi to 400 μCi

EXAMPLES

Example 1—Production of the Anti-CD45 Immunoglobulin BC8

The murine anti-CD45 mAb BC8 was prepared from a hybridoma (ATCC No. HB-10507) that was initially developed by fusing mouse myeloma NS1 cells with spleen cells from a BALB/C mouse hyperimmunized with human phytohemagglutinin (PHA)-stimulated mononuclear cells. The original fused cells, after screening for microbial contaminations, were cultured using the JRH-Biosciences EXCell 300 medium supplemented with 1-2% Fetal Bovine Serum (FBS).

The hybridoma cell line was adapted for culture in a serum-free culture medium. Briefly, the cells in culture were slowly and gradually weaned off the serum albumin using the combo medium supplemented with glutamine, cholesterol, insulin and transferrin. The cells were then grown in up to 500 L scale to a density of >1×10$^6$ cells/ml. The medium was harvested and processed for the purification of the anti-CD45 antibody using a combination of cation exchange chromatography, protein-A chromatography, and anion exchange membrane separation. The purified antibody was concentrated by nano-filtration (30 kD cutoff). The concentration of the purified product was measured at 5.2 mg/ml and was stored at 2-8° C.

The purified antibody was characterized by SDS-PAGE, IEF, and SEC-HPLC techniques. A single product peak (99.4%) was recorded with SEC-HPLC with about 0.6% aggregates. The non-reducing SDS-PAGE showed a single band for the antibody. The SDS-PAGE under reduced conditions confirmed the presence of the light and the heavy chains (99.9% together).

Example 2—Sequencing of the Anti-CD45-Immunoglobulin BC8

Total RNA was isolated from the hybridoma cells following the technical manual of Trizol® Reagent. The total RNA was analyzed by agarose gel electrophoresis and was reverse transcribed into cDNA using isotype-specific anti-sense primers or universal primers following the technical manual of PrimeScript™ 1st Strand cDNA Synthesis Kit. The antibody fragments of VH, VL, CH and CL were amplified and were separately cloned into a standard cloning vector using standard molecular cloning procedures. Colony PCR screening was performed to identify clones with inserts of correct sizes. More than five single colonies with inserts of correct sizes were sequenced for each antibody fragment. The complete nucleotide sequence of the light and the heavy chains are shown in FIGS. 4A, 4B, 5A, and 5B.

The anti-CD45-immunoglobulin (i.e., BC8 antibody) was sequenced using the mass spectrometry peptide mapping approach. The BC8 antibody was de-glycosylated, reduced and digested with individual enzymes; trypsin, Lys-C and chymotrypsin. The peptide fragments were then analyzed by the LC-coupled mass spectrometry technique using the MS/MS fragmentation analysis approach. Protein sequencing of the heavy and light chains of the BC8 antibody showed that the actual amino acid sequence differs from that predicted by the DNA sequence by only a single amino acid in the heavy chain. As highlighted in FIGS. 5A and 5B, the codon that codes for the amino acid at position 141 predicts an ASN-141 and not the actual ASP-141 found by protein sequencing. Moreover, sequencing of various batches of the protein indicated differing amounts of the ASP and ASN at position 141, i.e., the protein was found to comprise both ASN-141 and ASP-141 in ratios of from 1:99 to 99:1, such as 10:90 to 90:10 (ASN-141:ASP-141). See Table 1.

TABLE 1

LCMS/MS analysis of peptide fragment 124-151 from two
batches of isolated BC8 mAb showing the presences of both
"N" and "D" at position-141 in difference abundance.

| BC8 mAb Lot | Peptide Fragment Sequence (124-151 fragment) | Observed [M + H]⁺ (Da) | Theoretical [M + H]⁺ (Da) | % Abundance |
|---|---|---|---|---|
| GBI Lot | TTPPSVYPLAPGSAAQTNSM VTLGCLVK | 2860.4663 | 2860.4583 | 84.4% |
| | TTPPSVYPLAPGSAAQTDSM VTLGCLVK | 2861.4470 | 2861.4423 | 15.6% |
| Lot#2014 | TTPPSVYPLAPGSAAQTNSM VTLGCLVK | 2860.4627 | 2860.4583 | 43.6% |
| | TTPPSVYPLAPGSAAQTDSM VTLGCLVK | 2861.4479 | 2861.4423 | 56.4% |

This type of post-translational modification, i.e., deamination, may depend on the cellular environment and, in some cases, has been postulated to be related to protein age (e.g., may provide a signal for protein degradation). The fact that other deaminated amino acids were not identified, however, may be indicative of an important and specific role for ASP-141. At the very least, ASP-141 may be in an exposed or accessible region on the folded protein. That is, ASN-141 may be solvent accessible and reside within a conformationally flexible region of the antibody. The effect of deamination on the biological activity of the BC8 antibody may be determined from the results of human clinical trials.

Example 3—BC8: Labeling and Purification to Form ²²⁵Ac-BC8

Conjugation of BC8 and Irrelevant Control mAb 18B7 (Mouse IgG1) with DOTA

The antibodies against CD45 (i.e., BC8 antibody) and a control (i.e., mouse monoclonal reactive against the fungal polysaccharide glucuronoxylomannan; 2 mg each) were equilibrated with conjugation buffer (Na carbonate buffer with 1 mM EDTA, pH=8.5-9.0) by four ultrafiltration spins using either a Centricon filter with MW cutoff of 50,000, or a Vivaspin ultrafiltration tube with MW cutoff of 50,000; 1.5 milliliters (ml) of conjugation buffer per spin was used. For each spin, the antibodies were spun at 53,000 RPM for 5-20 minutes at 4° C. in a Thermo IEC Centra CL3R centrifuge with a fixed angle rotor to a residual retentate volume of 100-200 microliters (μl). Spin times vary for different antibodies and different protein concentrations. The antibodies were incubated at 4° C. for 30 minutes following the second and third spins to allow time for equilibration.

TABLE 2

| DOTA/Protein Molar Ratio | | |
|---|---|---|
| Initial | Final | Radiolabeling Yield |
| 5 | 1.2 | 70 |
| 5 | 1.2 | 68 |
| 5 | 1.2 | 67 |
| 5 | 1.2 | 75 |
| 7.5 | 1.5 | 82 |
| 7.5 | 1.5 | 83 |
| 7.5 | 1.5 | 81 |
| 7.5 | 1.5 | 83 |
| 15 | 1.4 | 80 |
| 15 | 1.4 | 82 |

TABLE 2-continued

| DOTA/Protein Molar Ratio | | |
|---|---|---|
| Initial | Final | Radiolabeling Yield |
| 15 | 1.4 | 80 |
| 15 | 1.4 | 83 |

For the conjugation, a solution of DOTA-pSCN (MW=678) at 3 mg/ml in 0.15M NH4OAc was prepared by dissolved by vortexing. DOTA-pSCN and the antibodies (at >5 mg/ml) and were mixed together at 5, 7.5 and 15 molar ratios in Eppendorf tubes and incubated for 15 hours at room temperature (see FIG. 9A). For purification of the DOTA-antibody conjugates the unreacted DOTA-pSCN was removed by 7 rounds of ultrafiltration as described above, washing each time with 1.5 ml of 0.15 M NH4OAc buffer, pH=6.5 down a volume of approximately 100 μl. After the final wash, 0.15 M NH4OAc buffer was added to bring each sample to a final concentration of ~1 mg/ml.

The final concentration of the DOTA antibody conjugates was measured by the simplified Lowry method. The number of DOTA molecules conjugated to the antibodies (DOTA to protein molar ratio) was determined as described in Dadachova et al., 1999, Spectrophotometric method for determination of bifunctional macrocyclic ligands in macrocyclic ligand-protein conjugates, Nuclear Medicine & Biology, 26:977-982. The results of the DOTA to protein molar ratio determination are shown in Table 2.

Radiolabeling of DOTA-Antibody Conjugates with $^{225}$Ac

A reaction comprising 15 μl 0.15M NH4OAc buffer, pH=6.5 and 2 μL (10 μg) DOTA-BC8 (5 mg/ml) was mixed in an Eppendorf reaction tube, and 4 μL $^{225}$Ac (10 μCi) in 0.05 M HCl was subsequently added (see FIG. 9B). The contents of the tube were mixed with a pipette tip and the reaction mixture was incubated at 37° C. for 90 min with shaking at 100 rpm. At the end of the incubation period, 3 μL of a 1 mM DTPA solution was added to the reaction mixture and it was incubated at room temperature for 20 min to bind the unreacted $^{225}$Ac into the $^{225}$Ac-DTPA complex.

Instant thin layer chromatography (ITLC) with 10 cm silica gel strip and 10 mM EDTA/normal saline mobile phase was used to determine the radiochemical purity of $^{225}$Ac-DOTA-BC8 through separating $^{225}$Ac-labeled BC8 ($^{225}$Ac-DOTA-BC8) from free $^{225}$Ac ($^{225}$Ac-DTPA). In this system the radiolabeled antibody stays at the point of application and $^{225}$Ac-DTPA moves with the solvent front. The strips were cut in halves and counted in the gamma counter equipped with the multichannel analyzer using channels 72-110 for $^{225}$Ac to exclude its daughters. Select radiolabeling results are presented in Table 2, which demonstrate that the conjugate formed at an initial molar ratio of DOTA to BC8 of 7.5 provided the highest conjugation ratio (DOTA to BC8 protein) and was chosen for all follow-up experiments described below (batch A).

Purification of $^{225}$Ac-DOTA-BC8 and HPLC of the Purified $^{225}$Ac-DOTA-BC8

The $^{225}$Ac-DOTA-BC8 samples were purified either on PD10 columns pre-blocked with 1% HSA or on the Vivaspin centrifugal concentrators with 50 kDa MW cut-off with 2×1.5 mL washes, 3 min per spin. The HPLC analyses of the $^{225}$Ac-DOTA-BC8 after purification were conducted using a Waters HPLC system equipped with flow-through Waters UV and Bioscan Radiation detectors. The injected samples size was 30 μL. The elution was carried out on a TSK3000SW XL column using PBS at pH=7.4 as an eluent and a flow rate of 1 ml/min. Example chromatograms are provided in FIGS. 10A and 10B, which show SEC-HPLC (size exclusion chromatography-HPLC) of $^{225}$Ac-DOTA-BC8, wherein FIG. 10A shows the BC8 standard, and FIG. 10B shows the $^{225}$Ac-DOTA-BC8 (the peak at 13 min is HSA added to stabilize the final formulation).

Example 4—$^{225}$Ac-BC8: Stability $^{225}$Ac-DOTA-BC8 Stability Determination

The DOTA-BC8 (batch A) was used in all immunoreactivity experiments and was radiolabeled with $^{225}$Ac as described in the procedure above at 1 μCi/μg specific activity. For the stability determination, the $^{225}$Ac-DOTA-BC8 was tested either in the original volume of 20 L, or diluted to 40 L or 60 L with the working buffer (0.15 M NH4OAc) and incubated at room temperature (rt) for 48 hours or at 4° C. for 96 hours and tested by ITLC. All samples were analyzed in duplicate and the experiment was performed three times.

The results shown in FIG. 11 demonstrate that the actinium-225 labeled BC8 ($^{225}$Ac-DOTA-BC8) was stable at 4° C. for up to 96 hours.

Example 5—$^{225}$Ac-BC8: Immunoreactivity $^{225}$Ac-DOTA-BC8 Immunoreactivity (IR) Determination Using Cell Lines The DOTA-BC8 (batch A) was used in all immunoreactivity experiments and was radiolabeled with $^{225}$Ac as described in the procedure above at 1 μCi/μg specific activity. The Ramos CD45 positive cells and control CD45 negative EL4 cells were used in the amounts of 1.0-7.5 million cells per sample, in duplicate. The experiment was performed twice. The results presented in FIG. 12 demonstrate that $^{225}$Ac-DOTA-BC8 bound specifically to Ramos cells with 50% of the radiolabeled antibody binding to these cells versus only around 10% binding to control EL4 cells. However, continuously growing two cell lines in the laboratory for QC is not cost effective, and simpler assays were desired for IR determination. As controls the following conditions were used: Ramos cells pre-blocked with 1% BSA; EL4 cells; EL4 cells pre-blocked with 1% BSA.

$^{225}$Ac-DOTA-BC8 Immunoreactivity (IR) Determination Using Cytotrol Cells

Cytotrol cells (Beckman Coulter) were initially used to determine the binding of naïve BC8 antibody to those cells versus control 18B7 antibody (nonspecific control antibody against the fungal polysaccharide glucuronoxylomannan) by flow cytometry (FIG. 13A). The cells were taken up in RPMI medium, and the secondary antibody was PE labeled rat anti-mouse IgG1 from Biolegend. CytoTrol cells are lyophilized human lymphocytes isolated from peripheral blood that exhibit CD45 surface antigen and were selected based on their commercial availability (Beckman Coulter) and consistency.

The binding of naïve BC8 to Cytotrol cells was compared to that of DOTA-BC8 (FIG. 13B). Naïve BC8 showed strong binding to Cytotrol cells, while control 18B7 mAb bound only at the background level (FIG. 13B). The attachment of DOTA to BC8 reduced its IR to approximately 70% of the naïve BC8 IR (FIG. 13B).

TABLE 3

| | IR determination using Cytotrol cells for six samples of 225Ac-DOTA-BC8. | | | | | |
|---|---|---|---|---|---|---|
| Counts in the washes and bound to the cells | BC8 1 | BC8 2 | BC8 3 | BC8 4 | BC8 5 | BC8 6 |
| S1 | 6,456 | 6,000 | 6,234 | 7,011 | 7,534 | 6,589 |
| S2 | 2,443 | 1,830 | 1,900 | 1,300 | 890 | 1,711 |

TABLE 3-continued

IR determination using Cytotrol cells
for six samples of 225Ac-DOTA-BC8.

| Counts in the washes and bound to the cells | BC8 1 | BC8 2 | BC8 3 | BC8 4 | BC8 5 | BC8 6 |
|---|---|---|---|---|---|---|
| S3 | 780 | 650 | 521 | 543 | 499 | 623 |
| cells | 15,354 | 17,023 | 16,743 | 16,985 | 15,999 | 15,235 |
| % bound | 61.3 | 66.5 | 65.9 | 65.7 | 66.4 | 63.01 |
| Mean ± SD for 6 samples | | | 64.8 ± 2.14% | | | |

Subsequently we performed the IR determination for 225Ac-DOTA-BC8. To measure binding of the radiolabeled antibodies to the Cytotrol cells, we used 3 tubes of Cytotrol cells (lot 729154) for each sample, and measured binding for duplicate samples. Using 0.5 ml reconstitution buffer, washed from vial to vial, we pooled the cells. The vials were washed with two more aliquots of 0.5 ml, and the washes were pooled. The cells were collected by centrifugation for 4 minutes at 4000 rpm, blocked with 1 ml of RPMI containing 1% Bovine Serum Albumin (BSA), respun, and resuspended in 0.5 ml RPMI/BSA. Around 25,000 CPM of labeled antibody were added/vial. The vials were incubated for 1-hour at 37° C., shaking at 150 RPM, spun 4 minutes at 4000 RPM, collect three washes, count washes and cells. Table 3 shows the IR determination for 6 samples of 225Ac-DOTA-BC8. The mean IR was 64.8±2.14%.

Finally, we performed the side by side comparison of the binding of DOTA-BC8 sample to Cytotrol cells by flow cytometry (FIG. 14B), followed by immediate radiolabeling of the same sample with $^{225}$Ac and binding of the radiolabeled sample to Cytotrol cells (FIG. 14A). The binding of the DOTA-BC8 to the cells by flow cytometry (around 60% of the naïve BC8 binding) matched that of radiolabeled $^{225}$Ac-DOTA-BC8 to Cytotrol cells. Accordingly, the Cytotrol assay was found to be a convenient and cost-effective way to evaluate the IR of $^{225}$Ac-DOTA-BC8 which routinely binds to the cells at 64.8±2.14%.

Example 6—$^{225}$Ac-BC8: Radioimmunotherapy for Multiple Myeloma

Evaluation of the Suitability of Human H929 and U266 Multiple Myeloma Cells as Model Cell Lines for Radioimmunotherapy (RIT) of Multiple Myeloma with $^{225}$Ac-DOTA-Bc8

The multiple myeloma (MM) cell lines H929 and U266 were purchased from the American Type Tissue Collection ATTC and grown according to the ATCC instructions. Binding of the unlabeled DOTA-BC8 to both cell lines was measured by flow cytometry (FIG. 15A), followed by the binding of $^{225}$Ac-DOTA-BC8 to the cells (FIG. 15B).

Subsequently, the H929 and U266 cells were used for an in vitro killing assay with $^{225}$Ac-DOTA-BC8. Two doses of $^{225}$Ac-DOTA-BC8 (20 µCi/ml and 250 µCi/ml) were used. The incubation of the cells with the radiolabeled antibodies was done in 96 well plates in a 200 ul total volume. The same two doses of the control antibody $^{225}$Ac-DOTA-18B7 were used. The cells were washed from unbound radioactivity at 4- and 12-hour time points, and their survival was evaluated with a Trypan blue assay 3 days later (Table 4). The killing of both cell lines was antibody-specific and dose dependent. That is, both cell lines expressed a sufficient amount of CD45 on their surface for specific targeting by $^{225}$Ac-DOTA-BC8 and could be used for the subsequent in vivo experiments.

TABLE 4

Combined data for two experiments on treatment
of H929 and U266 cells with
$^{225}$Ac-DOTA-BC8 and tested for survival 3 days later

| Treatment group | Surviving cells, % | |
|---|---|---|
| | 4 hours | 12 hours |
| U266, untreated | 92 ± 10 | 83 ± 8 |
| U266, $^{225}$AcBC8, 20 pCi/mL | 24 ± 7 | 14 ± 2 |
| U266, $^{225}$AcBC8, 250 pCi/ML | 2 ± 1 | 5 ± 1 |
| U266, $^{225}$Ac18B7, 20 pCi/ML | 75 ± 8 | 78 ± 10 |
| U266, $^{225}$Ac18B7, 250 pCi/ML | 50 ± 9 | 57 ± 7 |
| H929, untreated | 97 ± 12 | 92 ± 10 |
| H929, $^{225}$AcBC8, 20 pCi/mL | 33 ± 7 | 22 ± 6 |
| H929, $^{225}$AcBC8, 250 pCi/mL | 12 ± 3 | 6 ± 1 |
| H929, $^{225}$Ac18B7, 20 pCi/mL | 72 ± 12 | 80 ± 13 |
| H929, $^{225}$Ac18B7, 250 pCi/mL | 60 ± 11 | 55 ± 14 |

Example 7—$^{225}$Ac-BC8: Biodistribution

Biodistribution of $^{225}$Ac-DOTA-BC8 in a Naïve Mouse Model

The purpose of this study was to evaluate the pharmokinetic biodistribution of $^{225}$Ac-DOTA-BC8 versus a control $^{225}$Ac-DOTA-18B7 antibody in a naïve mouse model to ascertain baseline biodistribution and clearance in the absence of disease. The DOTA conjugated BC8 antibody (batch A) and 18B7 antibody (produced at the same molar ratio as batch A; 7.5 moles DOTA to Ab) were radiolabeled with $^{225}$Ac as detailed above. The antibodies were radiolabeled with the specific activity of 0.4 µCi/µg. The $^{225}$Ac-DOTA-BC8 immunoreactivity was tested with the Cytotrol cells and demonstrated 55% binding, thus meeting the 50% minimal binding requirement.

Fifty (50) healthy CD-1 mice female mice were randomly assigned to two groups and injected intraperitoneally with either $^{225}$Ac-DOTA-BC8 or control $^{225}$Ac-DOTA-18B7. Each mouse received 5 µg (2 µCi) of the radiolabeled antibody in 100 µl of 0.15 M NH$_4$OAc buffer with ascorbic acid. The intraperitoneal route is preferential to tail vein injections in the case of the long-lived radionuclides such as $^{225}$Ac to avoid contamination of the personnel, animals, and the facility (i.e., due to the possible back pressure splash from the tails). According to our own and other groups data, intraperitoneally injected antibodies completely leave peritoneum within one-hour post injection. The mice were euthanized at 1, 4, 24, 48, and 96 hours (n=5 mice per construct per time-point). Tissue samples (brain, muscle, bone (femur with the bone marrow), heart, lung, liver, spleen, kidneys, stomach, intestine, and blood) were collected from each mouse, weighed, and the accumulated activity per tissue counted in the gamma counter using $^{225}$Ac energy window.

The percentages of injected dose per gram (ID/g, %) are shown in FIGS. 16A and 16B. The results show that the patterns of the biodistribution and pharmokinetic clearance of the two antibodies were very close to each other, which attests to the overall stability of the one-step labeled antibodies in vivo. The clearance from the blood and blood-rich organs and uptake of the control $^{225}$Ac-DOTA-18B7 was somewhat lower, which is explained by the lack of homology between murine proteins and the 18B7 antigen (the fungal polysaccharide glucuronoxylomannan).

We also performed calculations to determine the $^{225}$Ac-DOTA-BC8 and $^{225}$Ac-DOTA-18B7 antibody half-lives in the blood and blood-rich organs (lungs and heart) using the data in FIGS. 16A and 16B, and Prizm 5.0 software (Graph-Pad, San Diego, CA). The results are presented in Table 5, which show the half-life of $^{225}$Ac-DOTA-BC8 to be around 100 hours (4.2 days), which is typical for a full-size murine IgG1 to a mammalian antigen, and the half-life of $^{225}$Ac-DOTA-18B7 (also a murine IgG1) to be only 30 hours (1.25 days), likely because of the foreign nature of its respective antigen (the fungal polysaccharide). Thus, it appears that the radiolabeled antibodies are stable in vivo, clear fast from the blood and blood rich organs, and are suitable for use in subsequent pharmokinetic experiments in CD45-positive tumor-bearing mice.

TABLE 5

| $^{225}$Ac-DOTA-BC8 and $^{225}$Ac-DOTA-18B7 half-lives in the blood and blood-rich organs | | |
|---|---|---|
| | Half-life, hours | |
| Organ | $^{225}$Ac-BC8 | $^{225}$Ac-18B7 |
| blood | 100 ± 5 | 30 ± 3 |
| lungs | 90 ± 3 | 20 ± 2 |
| heart | 104 ± 4 | 22 ± 4 |

Biodistribution of $^{225}$Ac-DOTA-BC8 mAb in Myeloma Tumor-Bearing SCID Mice

The purpose of this study was to understand the biodistribution of $^{225}$Ac-DOTA-BC8 versus a control $^{225}$Ac-DOTA-18B7 antibody in a multiple myeloma SCID mouse model. The DOTA-conjugated BC8 (batch A) and 18B7 (as above) were radiolabeled with $^{225}$Ac as above with the specific activity of 0.4 μCi/μg. Their immunoreactivity was tested with the Cytotrol cells and demonstrated 61% binding, thus meeting the 50% minimal binding requirement.

Fifty (50) SCID-NOD (severe combined immunodeficiency non-obese diabetic) female 4-5 weeks old mice (Charles River Laboratories) were injected subcutaneously with $10^7$ human multiple myeloma H929 cells (ATCC) into the right flank and with $10^7$ human multiple myeloma U266 cells (ATCC) into the left flank. In approximately 20 days, when the tumors reached 3-4 mm in diameter, the mice were randomized into two 2 groups of 25 mice and injected intraorbitally with either $^{225}$Ac-DOTA-BC8 or control $^{225}$Ac-DOTA-18B7 mAb. Each mouse then received 0.4 μCi (1 μg) of the radiolabeled antibody in 50 μl of 0.15M NH$_4$OAc buffer with ascorbic acid. As indicated above, the intraorbital route is preferential to tail vein injections to avoid possible back pressure splash from the tails. The mice were euthanized at 1, 4, 24, 48, and 96 hours (n=5 mice per construct per time-point). The tumors and tissue samples (brain, muscle, femur, bone marrow, heart, lung, liver, spleen, kidneys, stomach, intestine, and blood were collected from each mouse, weighed, and the accumulated activity per tissue counted in the gamma counter using $^{225}$Ac energy window.

The results are presented in FIGS. 17A and 17B as a percentages of injected dose per gram (ID/g, %). The uptake of $^{225}$Ac-DOTA-BC8 in the H929 and U266 tumors was significantly (P=0.01) higher than that of $^{225}$Ac-DOTA-18B7. Both antibodies cleared quickly from the blood and blood rich organs. Importantly, there was no uptake of $^{225}$Ac-DOTA-BC8 in bone marrow, attesting to the lack of any homology to human CD45 in mouse bone marrow. These results show that $^{225}$Ac-DOTA-BC8 localizes specifically in H929 and U266 tumors and thus could be used for further radioimmunotherapy (RIT) experiments.

Example 8—$^{225}$Ac-BC8: Radioimmunotherapy of Tumors in Mice

Radioimmunotherapy (RIT) of H929 and U266 Tumors in SCID-NOD Mice with 225Ac-DOTA-BC8

The therapeutic potential of $^{225}$Ac-DOTA-BC8 for the treatment of multiple myeloma xenografts in a mouse model was evaluated using forty (40) SCID-NOD female 4-5 weeks old mice. The mice were injected subcutaneously with $10^7$ H929 (right flank) and U266 (left flank) human multiple myeloma cells as in the biodistribution experiments. In approximately 19 days, when the tumors reached 3-4 mm in diameter, the mice were randomized into the groups of 8 and treated intraorbitally with: 0.3 μCi $^{225}$Ac-DOTA-BC8; 0.3 μCi $^{225}$Ac-DOTA-18B7 control mAb; a matching amount of unlabeled BC8; or left untreated. The size of the tumors was measured on the day of treatment and every three days thereafter with the electronic calipers. The mice were monitored for their tumor size and well-being for 30 days.

The results of the RIT study are shown in FIGS. 18A and 18B. There was a pronounced therapeutic effect of $^{225}$Ac-DOTA-BC8 on both H929 and U266 tumors. The matching activity of the control $^{225}$Ac-DOTA-18B7 had some effect on the tumor size, however, it was significantly (P=0.02) less than that of $^{225}$Ac-DOTA-BC8. Thus, it is clear that the RIT of mice bearing multiple myeloma xenografts was effective in almost completely abrogating the tumor growth and not having any undesirable side effects.

Histological Analysis of the Tumors Post RIT

At the completion of the RIT experiment, the mice were sacrificed, their tumors excised, placed in ethanol followed by buffered formaline, paraffinized, cut into 5 μm sections and stained with H&E. FIGS. 19A-19D show the H929 and U266 tumors from the untreated and $^{225}$Ac-DOTA-BC8 treated mice. The untreated tumors are much more coherent than the RIT treated tumors which show lack of coherence and necrosis.

Example 9—$^{225}$Ac-30F11: Marrow Ablative Effect of Anti-CD45 Surrogate

In this study we have evaluated the tolerability and myeloablative effects of $^{225}$Ac-labelled anti-mouse pan-CD45 antibody clone 30F11 in mice for targeted conditioning prior to BMT. Thus, the dose-dependent myeloablative effects of $^{225}$Ac-anti-CD45 antibody (30F111) on B6-Ly5$^a$ mice was evaluated. Further, the study evaluated the extent of engraftment and donor chimerism following congenic bone marrow transplant with B6-Ly5$^b$(CD45 allotype difference for monitoring chimerism).

Experimental Methods (1) Conjugation and Labeling of 30F11.

The anti-CD45 antibody 30F11 was conjugated with the chelator DOTA as described above. To test if the DOTA-conjugated 30F11 retains immunoreactivity, cells shown to be CD45 positive were incubated with naked 30F11 and DOTA-30F11 and the amount of bound Ab was determined by flow cytometry using anti-ratIgG2b$^{PE}$ to detect bound antibodies.

The DOTA-30F11 was radiolabeled with $^{111}$In or $^{225}$Ac as described hereinabove to a specific activity of 5 μCi/1 μg (1:1) or 1 μCi/1 μg (1:1) antibody, respectively, and radiochemical purity of 99±1.

(1) Biodistribution of Anti-CD45 Antibody 30F11 in C57Bl/6 Mice.

C57Bl/6 mice were injected i.v. with 60 μg $^{111}$In-30F11 with a specific activity of 5 μCi/μg. From 1 to 240 h after injection, the spleen was found to have the highest uptake of $^{111}$In-labeled-30F11, followed by bone marrow and liver. Kidneys, ovaries, lungs and blood showed minimal uptake. The biodistribution for each organ was fitted to a time-activity curve to calculate the accumulated activity for each organ. The equilibrium dose constants of $^{225}$Ac was then applied to obtain the dose to organ per administered activity, reported in Table 6.

TABLE 6

| $^{225}$Ac-CD45 antibody Absorbed dose to Organs | |
|---|---|
| Organ | cGy/uCi |
| Blood | 24.3 |
| Spleen | 8691.8 |
| Liver | 2310.6 |
| Ovary | 97.5 |
| Kidnet | 578.0 |
| Lung | 140.8 |
| Bone Marrow | 3963.5 |

(2) Dose Dependent Tolerability of $^{225}$Ac-30F11 in B6-Ly5$^a$ Mice.

In order to determine tolerability of $^{225}$Ac-CD45 antibody radio-conjugate, C57Bl/6 (5 per cohort) were treated with escalating doses of $^{225}$Ac-30F11 on day zero. Three ascending dose levels (100 nCi, 250 nCi, and 500 nCi) were administered in a total of 10 ug (ca. 0.5 mg/kg) of 30F11 antibody (volume 100 to 200 ul) injected into the tail vein (IV). Five untreated mice served as control for this study. Immediately prior to conditioning, pre-treatment blood samples were drawn from the control mice for baseline blood cell count measurements. Each of RBC and WBC were measured at weeks 1 and 2, and the mice euthanize at week 4. Blood was collected from euthanized mice & analyzed for liver & kidney toxicity i.e., blood urea nitrogen (BUN), creatine, alanine transaminase (ALT), and aspartate aminotransferase (AST) measured. A Kaplan-Meier graph showed that each of the 100 nCi and 250 nCi doses were well tolerated, while the 500 nCi dose showed a decreased probability of survival after 1 week.

(3) Safety Profile of $^{225}$Ac-30F11 in B6-Ly5$^a$ Mice.

In order to determine the safety profile of 225Ac-CD45 bone marrow engraftment, C57Bl/6 mice were treated with $^{225}$Ac-30F11 and reconstituted with donor bone marrow (CD45.1) as follows: 100 nCi or 250 nCi of $^{225}$Ac-30F11 was injected on Day 0 (as above). Four days after conditioning, half of the cohorts received congenic bone marrow (BMT) harvested from C57Bl/6-Ly5$^b$ mice at a target density of marrow of 10$^7$ nucleated cells injected via tail vein. Mice were regularly monitored for body weight and overt signs of changes in health and behavior.

Engraftment and donor chimerism was evaluated by blood collection, and mice were euthanized at 12 weeks.

Engraftment was assessed by total WBC, RBC, HSC, neutrophil, and platelet counts, and BUN, creatinine, ALT, and AST.

Results: 500 nCi $^{225}$Ac-30F11 was found to be a maximum tolerated dose for this myeloablation modality. Mice treated with 250 and 100 nCi of $^{225}$Ac-30F11 demonstrated effective myeloablative conditioning and donor BM engraftment in a dose dependent manner without any long-term hematological toxicity.

Conclusion: The pan-CD45-targeting antibody 30F11 armed with $^{225}$Ac appears to be a safe and potent targeted conditioning approach for BMT. This data supports the development of CD45 targeted ablation prior to BMT using $^{225}$Ac-armed antibodies.

Example 10—Lymphodepletion with $^{177}$Lu-Anti-CD45 and $^{131}$I-Anti-CD45

Prior to a patient receiving a dose of an adoptive cell transfer such as engineered autologous or allogeneic CAR-T cells, it is common to perform a lymphodepletion step often using high dose chemotherapy. This process is considered important to create sufficient space in the immune microenvironment, e.g. bone marrow, to allow the transferred cells to engraft. Further, it appears to elicit a favorable cytokine profile for establishment and proliferation of the donor lymphocytes. In this study, use of the beta emitter $^{177}$Lu (6.6 day half-life; 1.5 mm path length) for mediating effective lymphodepletion in mouse models is tested. Preclinical studies using a $^{177}$Lu-labeled and $^{131}$I-labeled surrogate anti-mouse pan-CD45 antibody (30F11) were performed to investigate in a mouse model the response of targeted RIT lymphodepletion on particular immune cell types and resulting changes in immune cytokine expression.

Following single dose administration of non-myeloablative doses of $^{177}$Lu-CD45-RIT, peripheral blood, bone marrow and spleen samples were collected from 8-12 week C57Bl/6 mice at 96 hours and 10 days post-treatment for immunophenotyping to evaluate lymphoid and myeloid subsets for lymphodepletion, and serum for cytokine profiling. $^{177}$Lu-CD45-RIT was shown to effectively lymphodeplete both lymphocyte and myeloid cells, inclusive of immune suppressive T regs and MDSCs. Studies evaluating this targeted lymphodepletion regimen in E.G7 lymphoma tumor bearing mice prior to adoptive cell transfer with OVA-specific CD8+ T cells will also be presented.

Methods and Materials

The anti-mouse pan-CD45 antibody 30F11 was labeled with Lutetium-177 ($^{177}$Lu-CD45) and Iodine-131 ($^{131}$I-CD45) and used as a surrogate for radiolabeled pan-human BC8 to perform targeted lymphodepletion in mice. Immunoreactivity was confirmed in CD45+ cell-based binding assay to be >95%.

For lymphodepletion studies in mice: Female adolescent C57Bl/6 mice were treated with 20 ug of 30F11 labelled with 20 or 40 μCi of $^{177}$Lu or 50 or 100 μCi of $^{131}$I to determine the ability to selectively deplete immune cell subsets. Immune cell subset quantitation was measured by flow cytometry.

For lymphodepletion studies in OT I mouse model: Female adolescent C57Bl/6 CD45.1 mice were injected subcutaneously with OVA expressing CD45+E.G7-OVA lymphoma tumor cells until 100 mm3 tumor volume reached. Approximately 7 days post-tumor cell injection, mice were treated with $^{177}$Lu-CD45 (40 μCi), $^{131}$ICD45

(100 µCi), or received no lymphodepletion treatment. Four days post-lymphodepletion, isolated CD8+ T cells isolated from CD45.2 OT I mice were administered to mice. Tumor volume and body weight were monitored, and mice were sacrificed when tumor volume exceeded 4000 mm³ or became necrotic.

Results

Anti-CD45 antibody was conjugated to DOTA at a ratio 20:1 and then labeled with $^{111}$In at a ratio of 5:1. C57Bl/6 mice were injected i.p. with 60 µg $^{111}$In-labeled anti-CD45 antibody with a specific activity of 5 µCi/µg and antibody distribution was monitored by microSPECT/CT at indicated time points. CD45 antibody homed to immune system organs: lymph nodes, spleen, and bone marrow (see FIG. 20).

The radiolabeled anti-CD45 antibodies [177]Lu-CD45 and [131]I-CD45 were found to transiently deplete CD45+ immune cell subsets without affecting platelets, red blood cells, or bone marrow cells. As shown in FIG. 21, treatment of non-tumor bearing C57B/6 mice with (A) 20 or 40 µCi [177]Lu-CD45 or (B) 50 or 100 µCi [131]-I CD45 antibody was similarly effective in transiently lymphodepleting various immune cell populations without affecting bone marrow cells, red blood cells, or platelets.

Moreover, the $^{177}$Lu radiolabeled anti-CD45 antibodies were found to transiently deplete CD45-expressing immune cell subsets in the spleen. As shown in FIG. 22, treatment of non-tumor bearing C57B/6 mice with 40 µCi [177]Lu-CD45 antibody was effective in transiently depleting various immune populations in the spleen including regulatory T cells (T-regs). This lymphodepletion enabled tumor control in an OT 1 adoptive cell therapy model.

As shown in FIG. 23, Following E.G7 tumor engraftment, mice either received no conditioning (Untreated and OT I) or were conditioned with 40 µCi 177Lu-CD45 or 100 µCi of 131I-CD45 on Day 0 and then received 1×10⁶ OT I CD8+ CD45.2 OVA reactive T cells on day 4. Panel A shows results from [177]Lu-CD45 and [131]I-CD45-mediated targeted conditioning prior to adoptively transferred OT I T cells enabled control of EG.7 tumor growth. Panel B shows the tumor size for individual mice in each group. The OT1 T cell persistence and expansion was confirmed in mice at the time of sacrifice. Panel C shows the overall survival of control mice (i.e., received no conditioning or OT I T cells), mice who received OT 1 T cells, and those that also received the [177]Lu-CD45 and [131]I-CD45-mediated targeted conditioning.

CONCLUSIONS

These studies demonstrate the feasibility of using a low dose of [177]Lu-CD45 or [131]I-CD45 radioimmunotherapy as a transient non-myeloablative targeted lymphodepletion regimen prior to adoptive cell therapy. [111]In-CD45 imaging demonstrated that CD45 targeting delivers radiation selectively to immune privileged tissues. Studies determined that 40 µCi [177]Lu-CD45 or 100 µCi [131]I-CD45 could effectively deplete various immune cell subsets in mice but spare bone marrow cells, red blood cells, and platelets. In a model of adoptive cell therapy using CD45.1 OT1 mice bearing EG.7-OVA tumors, mice that received RIT-mediated lymphodepletion demonstrated enhanced tumor control over mice that did not receive lymphodepletion. This data supports CD45 targeted lymphodepletion prior to adoptive cell therapy using a non-myeloablative dose of [131]I-CD45 or [177]Lu-CD45 RIT.

Example 11—[225]Ac-BC8: Sickle Cell Disease (SCD)

This example describes HSC ablation (i.e., 100% depletion) preceding transplant with gene-edited HSCs in patients with SCD.

SCD is the most common hemoglobinopathy worldwide. The incidence of SCD among African Americans is approximately 1 in 500. It is estimated that 100,000 individuals are afflicted in the United States. SCD is caused by a single nucleotide mutation in the β-globin gene that produces sickle hemoglobin. SCD patients may exhibit anemia, vaso-occlusive crises (VOCs), hemolysis, chronic organ dysfunction, and early mortality. The mortality rate among children with SCD is 0.5 per 100,000. However, the mortality rate in adults is more than 2.5 per 100,000, and median life expectancy is less than 50 years of age for both men and women with SCD.

Currently, the only curative treatment for SCD is a hematopoietic stem cell transplant (HSCT). Unfortunately, HSCTs for SCD are not without problems. According to the Center for International Blood and Marrow Transplant Research, only 1,089 patients with SCD underwent HSCTs from 1991 to April 2017. Risks associated with HSCTs include complications (such as graft-versus-host disease) arising from the use of allogeneic donor stem cells.

With the advent of gene editing technologies, there is now an opportunity to cure SCD patients using autologous stem cells in which the mutation in the β-globin gene responsible for SCD has been corrected. ZFN, TALEN, CRISPR/cas9 and other nuclease-mediated editing approaches could be used to repair, or remove and replace, stem cells from an SCD patient. For example, Sun and Zhao (Biotech. And Bioeng., 2014, 111(5)) demonstrated the successful repair of the human β-globin gene mutation in patient pleuripotent HSCs using TALENs. In addition, Dever, et al., (Nature, 2016, 539:384-389) demonstrated efficient repair of the Glu6Val mutation responsible for SCD in patient HSCs using CRISPR/cas9. Clinical trials using this approach for SCD are now starting.

Unfortunately, standard myeloablative conditioning regimens (i.e., 100% HSC-depleting regimens) using high dose chemotherapy or total body irradiation are currently used for transplants, including for autologous gene-edited cell transplants. There is a need for a safer and more effective conditioning method for these patients. Radiolabeled BC8 (e.g., [225]Ac-BC8) would be more sparing of a patient's normal tissues. Notably, older patients with SCD may already have organ damage as a result of their disease, and exposure to non-specific radiation or chemotherapy as a myeloablative conditioning regimen could make performing a stem cell transplant even riskier. A radiolabeled BC8 approach presents a better option for these patients.

Further, due to the hereditary nature of the disease, correcting the disease through transplantation of gene-edited HSCs is preferred as early in life as possible, as complications of the disease may be irreversible and have a negative impact on long-term survival for the patient. As such, treating infants or young children afflicted with SCD using gene-edited HSCs is envisioned. To this end, radiolabeled BC8, particularly BC8 labeled with an alpha-emitting radionuclide such as [225]Ac, would be ideal. The use of an alpha-emitting radionuclide such as [225]Ac, with its very short, high energy radiation path length, would focus the radiation on CD45-positive cells and allow for effective myeloablation without the need to isolate treated patients (as would be required for conditioning with a myeloablative dose of a $^{131}$I-BC8).

Example 12—$^{225}$Ac-BC8: Severe Combined Immunodeficiency (SCID)

This example describes HSC ablation preceding transplantation with gene-edited HSCs in patients with Severe combined immunodeficiency (SCID).

SCID is a germline genetic disorder in which afflicted patients present with severe T cell defects, with or without accompanying B cell defects. SCID involves a defective adaptive immune response that prevents patients from mounting an effective antibody response to pathogens. SCID is the most severe form of primary immunodeficiencies, and there are at least nine different known genes where mutations lead to SCID. Because SCID patients are incapable of mounting an adaptive immune response, they are susceptible to infection, and early mortality is high. SCID is also known as the "bubble boy" disease because patients must be kept in a sterile environment to avoid life-threatening infections.

The most frequent genetic defect in SCID is in the common gamma chain (γc), which is a protein that is shared by the receptors for interleukins IL-2, IL-4, IL-7, IL-9, IL-15 and IL-21. Other mutated genes that can lead to SCID are ADA and JAK3. As with SCD, only treatment with a stem cell transplant is potentially curative for SCID. However, delayed immune recovery and GVHD are significant risks for these patients. Also, as with SCD patients, SCID patients are young and therefore need effective and safe methods for treatment, including a better conditioning regimen prior to transplant.

Gene editing technology may precisely repair the defect in a SCID patient's own HSCs. Once returned to the body, these engineered HSCs can produce normal lymphocytes and establish a working adaptive immune response to protect against infection. Recently, Chang et al (Cell Reports, 2015, 12:1668-1677) reported effectively restoring normal lymphocyte development via CRISPR/cas9-mediated repair of a mutation in the JAK3 gene in mice. Further Alzubi, et al., (Nature, Scientific Reports, 2017, 7:12475) recently demonstrated using TALEN technology to precisely repair in mice a genetic defect in the IL2RG (common gamma chain), the gene responsible for X-SCID.

It is important that safer and more effective methods for conditioning human SCID patients are developed. Alpha-emitter CD45 radioimmunotherapy, such as with $^{225}$Ac-BC8, is needed to safely condition these predominantly young patients.

Example 13—$^{225}$Ac-BC8: Treatment Synopsis for Non-Malignant Disorders

Table 7 summarizes selected treatment regimens using gene-edited stem cell administration preceded by HSC depletion via administration of an actinium radiolabeled BC8 antibody (i.e., conditioning agent; $^{225}$Ac-BC8).

TABLE 7

| Disease | Therapy with Gene-edited HSCs or Pleuripotent Stem Cells Genes repaired include: |
|---|---|
| SCD | b-globin (HBB) |
| SCID | JAK3, Janus Family Kinase, ADA, adenosine deaminase, IL2RG, common gamma chain gene |
| β-Thalassemia | b-globin (HBB), BCL11A |
| Fanconi's Anemia | FANCC |
| Wiskott-Aldrich Syndrome | WAS |
| AIDS | CCR5 and CXCR4 |

What is claimed is:

1. A method for treating a hemoglobinopathy or a hematological disease or disorder comprising:

administering a composition comprising an effective amount of a population of anti-CD45 antibodies comprising light chain complementarity determining regions having the amino acid sequences set forth in SEQ ID NO:3, SEQ ID NO:4, and SEQ ID NO:5, and heavy chain complementarity determining regions having the amino acid sequence set forth in SEQ ID NO:6, SEQ ID NO:7, and SEQ ID NO:8, wherein the population of anti-CD45 antibodies comprises antibodies wherein the amino acid at position 141 of the heavy chain (relative to the N-terminal amino acid) is ASP and antibodies wherein the amino acid at position 141 of the heavy chain (relative to the N-terminal amino acid) is ASN, wherein a fraction of the population of anti-CD45 antibodies is radiolabeled with actinium-225 and the remaining fraction is not radiolabeled, wherein the fraction of the population of anti-CD45 antibodies radiolabeled with actinium-225 consists essentially of the conjugate of anti-CD45 monoclonal antibody with p-SCN-Bn-DOTA comprising chelated actinium-225, and wherein the effective amount is administered as a single dose.

2. The method of claim 1, wherein the anti-CD45 antibodies of the population have a light chain with the amino acid sequence set forth in SEQ ID NO: 13.

3. The method of claim 1, wherein the population of anti-CD45 antibodies comprises $^{225}$Ac-BC8 having a heavy chain with the amino acid sequence set forth in SEQ ID NO:2.

4. The method of claim 1, wherein the population of anti-CD45 antibodies consists essentially of BC8 antibodies wherein the amino acid at position 141 (relative to the N-terminal amino acid of the heavy chain) is ASP or ASN.

5. The method of claim 4, wherein the ratio of ASP:ASN at position 141 in the population of anti-CD45 antibodies consisting essentially of BC8 antibodies is 1:99 to 99:1.

6. The method of claim 1, further comprising:

administering an effective amount of a secondary agent.

7. The method of claim 6, wherein the secondary agent comprises a radiosensitizer comprises selected from a Bcl-2 inhibitor, an HDAC inhibitor, or any combination thereof.

8. The method of claim 1, wherein said administration of the composition depletes at least 50% of lymphocytes of the subject but does not induce myeloablation in the subject.

9. The method of claim 8, wherein said administration of the composition depletes circulating tumor cells of hematopoietic origin.

10. The method of claim 8, wherein said administration of composition provides a radiation dose of 2 Gy or less to the bone marrow.

11. The method of claim 8, wherein the effective amount comprises a radiation dose of 0.1 µCi/kg 1.0 µCi/kg or a dose of 10 µCi-150 µCi.

12. The method according to claim 8, wherein said administration of the composition depletes CD45+ circulating tumor cells but does not induce myeloablation in the subject.

13. The method of claim 10, further comprising: administering to the subject an effective amount of a population of cells expressing a chimeric antigen receptor or a T-cell receptor (CAR/TCR) 6, 7, or 8 days after administration of the composition in preparation of administering the population of cells.

14. The method of claim 1, wherein the subject is afflicted with a non-cancerous disorder treatable via genetically edited cell therapy and is about to undergo such said therapy to treat the disorder, and the is administered as a single dose in preparation of the subject undergoing said therapy, wherein the disorder is selected from the group consisting of a hemoglobinopathy, a congenital immunodeficiency, and a viral infection, or wherein the disorder is selected from the group consisting of sickle cell disease (SCD), severe combined immunodeficiency disease (SCID), β-thalassemia and Fanconi's anemia.

15. The method of claim 14, wherein the disorder is SCD and the therapy is genetically edited β-globin hematopoietic stem cell therapy.

16. The method of claim 14, wherein the disorder is SCID and the therapy is genetically edited hematopoietic stem cell therapy, wherein the edited gene is selected from the group consisting of the common gamma chain (ye) gene, the adenosine deaminase (ADA) gene and the Janus kinase 3 (JAK3) gene.

17. The method of claim 1, wherein the hemoglobinopathy or hematological disease or disorder is a hematological disease selected from myelodysplastic syndrome (MDS), multiple myeloma (MM), acute myeloid leukemia (AML), myeloproliferative neoplasm, or any combination thereof.

18. The method of claim 11, further comprising:

administering to the subject an effective amount of a population of cells expressing a chimeric antigen receptor or a T-cell receptor (CAR/TCR) 6, 7, or 8 days after administration of the composition.

19. The method of claim 1, wherein the population of anti-CD45 antibodies consists essentially of humanized BC8 antibodies comprising the light chain CDR sequences set forth in SEQ ID NO:3, SEQ ID NO:4, and SEQ ID NO:5 and the heavy chain CDR sequences set forth in SEQ ID NO:6, SEQ ID NO:7, and SEQ ID NO: 8.

20. The method of claim 5, wherein the ratio of ASP:ASN at position 141 of the heavy chain in the population of anti-CD45 antibodies is 10:90 to 90:10.

21. The method of claim 1, wherein the ratio of ASP:ASN at position 141 of the heavy chain in the population of anti-CD45 antibodies is 1:99 to 99:1.

22. The method of claim 21, wherein the ratio of ASP: ASN at position 141 of the heavy chain in the population of anti-CD45 antibodies is 10:90 to 90:10.

23. The method of claim 1, wherein the minority of the anti-CD45 antibodies in the population of antibodies are radiolabeled.

* * * * *